US011499177B2

(12) United States Patent
Kobayashi et al.

(10) Patent No.: US 11,499,177 B2
(45) Date of Patent: Nov. 15, 2022

(54) HORSESHOE CRAB FACTOR B VARIANT

(71) Applicant: SEIKAGAKU CORPORATION, Tokyo (JP)

(72) Inventors: Yuki Kobayashi, Tokyo (JP); Hikaru Mizumura, Tokyo (JP); Toshio Oda, Tokyo (JP); Shun-Ichiro Kawabata, Fukuoka (JP)

(73) Assignee: SEIKAGAKU CORPORATION, Tokyo (JP)

( * ) Notice: Subject to any disclaimer, the term of this patent is extended or adjusted under 35 U.S.C. 154(b) by 120 days.

(21) Appl. No.: 16/490,100

(22) PCT Filed: Mar. 1, 2018

(86) PCT No.: PCT/JP2018/007840
§ 371 (c)(1),
(2) Date: Aug. 30, 2019

(87) PCT Pub. No.: WO2018/159771
PCT Pub. Date: Sep. 7, 2018

(65) Prior Publication Data
US 2021/0363564 A1 Nov. 25, 2021

(30) Foreign Application Priority Data

Mar. 1, 2017 (JP) .............................. JP2017-038692

(51) Int. Cl.
*C12Q 1/37* (2006.01)
*C12N 9/50* (2006.01)
(52) U.S. Cl.
CPC ......... *C12Q 1/37* (2013.01); *C12N 9/50* (2013.01)
(58) Field of Classification Search
CPC ................................... C12Q 1/37; C12N 9/50
USPC ....................................................... 435/230
See application file for complete search history.

(56) References Cited

U.S. PATENT DOCUMENTS

2015/0307864 A1  10/2015  Mizumura et al.

OTHER PUBLICATIONS

Muta et al., Horseshoe Crab Coagulation Factor B. J Biol Chem . Oct. 5, 1993;268(28):21384-8.*
Ogino et al, Role of Intermolecular Disulfide Bonds of the Organic Solvent-Stable PST-01 Protease in Its Organic Solvent Stability. Applied and Environmental Microbiology, Feb. 2001, p. 942-947.*
Varalyay et al, The Role of Disulfide Bond C191-0220 in Trypsin and Chymotrypsin. Biochemical and Biophysical Research Communications 230, 592-596 (1997).*
Takagi, Functional Improvement of Subtilisin E, a Protease of Bacillus subtilis by Protein Engmeering . Nippon Nogeikagaku Kalshi, vol. 71, No. 10, pp. 995-1002, 1997. Partial English Translation.*
NCBI Acc#Q27081.1 from Muta et al., Horseshoe crab coagulation factor B. A unique serine protease zymogen activated by cleavage of an Ile-Ile bond. J Biol Chm 268 (28), 21384-21388 (1993)(of record). Alignment with SID10.*
Muta et al., "Horseshoe Crab Coagulation Factor B", The Journal of Biological Chemistry, vol. 268, No. 28, Oct. 5, 1993, pp. 21384-21388.
Nakamura et al., "Purification and Properties of Intracellular Clotting Factor, Factor B, from Horseshoe Crab (*Tachypleus tridentatus*) Hemocytes", The Journal of Biochemistry, vol. 99, No. 3, 1986, pp. 847-857.
Ogino et al., "Role of Intermolecular Disulfide Bonds of the Organic Solvent-Stable PST-01 Protease in Its Organic Sol vent Stabuility", Applied and Environmental Microbiology, vol. 67, No. 2, Feb. 2001, pp. 942-947.
Takagi, "Functional Improvement of Substilisin E, a Protease of Bacillus subtilis by Protein Engineering", Nippon Nogeikagaku Kaishi, vol. 71, No. 10, 1997, pp. 995-1002 (with partial English translation).
Varallyay et al., "The Role of Disulfide Bond C191-C220 in Trypsin and Chymotrypsin", Biochemical and Biophysical Research Communications, vol. 230, 1997, pp. 592-596.
International Search Report issued in International Pat. Appl. No. PCT/JP2018/007840, dated May 1, 2018.
International Preliminary Report on Patentability issued in International Pat. Appl. No. PCT/JP2018/007840, dated Sep. 3, 2019.
Ogino et al., "Role of Intermolecular Disulfide Bonds of the Organic Solvent-Stable PST-01 Protease in Its Organic Solvent Stability", Applied and Environmental Microbiology, vol. 67, No. 2, Feb. 2001, pp. 942-947.
Takagi, "Functional Improvement of Subtilisin E, a Protease of Bacillus subtilis by Protein Engineering", Nippon Nogeikagaku Kaishi, vol. 71, No. 10, 1997, pp. 995-1002 (with partial English translation).
Extended European Search Report issued in corresponding EP Application No. 18761685.9, dated Sep. 7, 2020.
Schwarz et al., "A0A023F4D5" Jun. 2014, URL:https://www.uniprot.org/uniprot/A0A023F4D5.txt.
Mizumura et al., "Genetic engineering approach to develop next-generation reagents for endotoxin quantification," *Innate Immunity*, vol. 23, No. 2, Feb. 2017, 136-146.
Search Report & Written Opinion issued in corresponding SG Application No. 11201907866S, dated Sep. 8, 2020.

* cited by examiner

*Primary Examiner* — Sheridan Swope
(74) *Attorney, Agent, or Firm* — Greenblum & Bernstein, P.L.C.

(57) ABSTRACT

Provided is a technology related to a horseshoe crab factor B variant, and also provided is means for performing endotoxin measurement with high sensitivity. A polypeptide having an amino acid sequence in which the amino acid residue at the 193-position in an amino acid sequence of a polypeptide of horseshoe crab factor B is substituted with a cysteine (Cys) residue, is produced. Endotoxin measurement can be carried out with high sensitivity by configuring a *Limulus* reagent by combining this polypeptide with horseshoe crab factor C.

9 Claims, 1 Drawing Sheet
Specification includes a Sequence Listing.

HORSESHOE CRAB FACTOR B VARIANT

SEQUENCE LISTING

The instant application contains a Sequence Listing which has been submitted electronically in ASCII format and is hereby incorporated by reference in its entirety. Said ASCII copy, created on Mar. 3, 2021, is named P58373_SL.txt and is 77,871 bytes in size.

TECHNICAL FIELD

The present invention relates to a horseshoe crab factor B variant.

BACKGROUND ART

A means for detecting a microorganism-derived substance in the hygiene management of medicines and food products or in the diagnosis of animals including human beings, and measuring the extent of microorganism contamination, is important. Regarding the means for measuring the extent of microorganism contamination, *Limulus* test is popularly used. The *Limulus* test is a technology for measuring the extent of microorganism contamination by using an endotoxin (LPS) or (1→3)-β-D-glucan as an object substance for measurement, and is a measurement method of utilizing the property that a protease precursor carried by horseshoe crabs is activated by these object substances for measurement.

Regarding the *Limulus* test, a method of using a horseshoe crab hemocyte extract (horseshoe crab amebocyte lysate; hereinafter, simply referred to as "lysate") is widely used. This method is a method of utilizing a cascade reaction that proceeds when serine protease precursors (factor C, factor B, and proclotting enzyme) come into contact with an endotoxin, or when serine protease precursors (factor G and proclotting enzyme) come into contact with (1→3)-β-D-glucan, the serine protease precursors are sequentially activated.

Non Patent Literature 1 discloses *Tachypleus tridentatus* factor B isolated from the lysate. Furthermore, Non Patent Literature 2 discloses an amino acid sequence of a polypeptide of *Tachypleus tridentatus* factor B. However, a factor B variant having enzyme characteristics that are superior to the factor B itself, is not disclosed in any of these literatures.

CITATION LIST

Non Patent Literature

Non Patent Literature 1: Nakamura, T., Horiuchi, T., Morita, T., Iwanaga, S (1986) J. Biochem. 99, 847-57 Non Patent Literature 2: Muta, T., Oda, T., Iwanaga, S. (1993) J. Biol. Chem. 268, 21384-8

SUMMARY OF INVENTION

Technical Problem

An object of the present invention is to provide a technology relating to a horseshoe crab factor B variant. Particularly, it is an object of the present invention to provide a polypeptide of a horseshoe crab factor B variant; a nucleic acid encoding the polypeptide; a vector retaining the nucleic acid; a cell retaining the nucleic acid and/or the vector; a method for producing the polypeptide; a method for measuring an endotoxin by using the polypeptide; a reagent for endotoxin measurement including the polypeptide as a constituent component; and a kit for endotoxin measurement including the polypeptide or the reagent as a component part.

Solution to Problem

The inventors of the present invention conducted a thorough investigation in order to solve the problems described above, and as a result, the inventors found that when an amino acid residue at a particular site in the amino acid sequence of a polypeptide of horseshoe crab factor B is modified, a horseshoe crab factor B variant having protease activity superior to that of the factor B itself may be obtained. Furthermore, the present inventors also found that a horseshoe crab factor B variant having thermal stability that is superior to that of the factor B itself may be obtained by the finding as described above. Thus, the present inventors completed the present invention based on these findings.

The problems described above can be solved by the present invention including the following embodiments.

[1]

A polypeptide having an amino acid sequence in which the amino acid residue at the 193-position in an amino acid sequence of a polypeptide of horseshoe crab factor B is substituted with a cysteine (Cys) residue.

[2]

A polypeptide represented by any one of the following (A) to (D):

(A) a polypeptide having an amino acid sequence represented by the following (A1) or (A2):

(A1) an amino acid sequence represented by amino acid numbers 1 to 400 of SEQ ID NO: 7; and (A2) an amino acid sequence represented by amino acid numbers 24 to 400 of SEQ ID NO: 7, (B) a polypeptide having an amino acid sequence represented by the following (B1) or (B2):

(B1) an amino acid sequence represented by amino acid numbers 1 to 400 of SEQ ID NO: 10; and (B2) an amino acid sequence represented by amino acid numbers 24 to 400 of SEQ ID NO: 10, (C) a polypeptide having an amino acid sequence including substitution, deletion, insertion, and/or addition of one amino acid residue or a plurality of amino acid residues in the amino acid sequence of the polypeptide represented by the item (A) or (B) described above (provided that the cysteine (Cys) residue at the 193-position is neither substituted nor deleted), the polypeptide having the function of horseshoe crab factor B, and (D) a polypeptide having an amino acid sequence of a fusion polypeptide in which a peptide tag is added to the polypeptide represented by any one of the items (A) to (C) described above, the polypeptide having the function of horseshoe crab factor B.

[3]

A nucleic acid encoding the polypeptide according to [1] or [2].

[4]

A DNA represented by any one of the following (a) to (d):

(a) a DNA having a base sequence represented by any one of the following (a1) to (a4):

(a1) a base sequence represented by base numbers 1 to 1200 of SEQ ID NO: 5;

(a2) a base sequence represented by base numbers 70 to 1200 of SEQ ID NO: 5;

(a3) a base sequence represented by base numbers 1 to 1200 of SEQ ID NO: 6; and (a4) a base sequence represented by base numbers 70 to 1200 of SEQ ID NO: 6, (b) a DNA having a base sequence represented by any one of the following (b1) to (b4):

(b1) a base sequence represented by base numbers 1 to 1200 of SEQ ID NO: 8;

(b2) a base sequence represented by base numbers 70 to 1200 of SEQ ID NO: 8;

(b3) a base sequence represented by base numbers 1 to 1200 of SEQ ID NO: 9; and (b4) a base sequence represented by base numbers 70 to 1200 of SEQ ID NO: 9, (c) a DNA hybridizing with a DNA including a base sequence complementary to the DNA represented by the item (a) or (b) described above under stringent conditions (provided that the bases represented by base numbers 577 to 579 are conserved), the DNA encoding a polypeptide having the function of horseshoe crab factor B, and (d) a DNA having a base sequence of a fusion DNA in which a peptide tag-encoding DNA is added to the DNA represented by any one of the items (a) to (c) described above, the DNA encoding a polypeptide having the function of horseshoe crab factor B.

[5]

A vector retaining the nucleic acid according to the item [3] and/or the DNA according to the item [4].

[6]

A cell retaining the nucleic acid according to the item [3], the DNA according to the item [4], and/or the vector according to the item [5].

[7]

A method for producing a polypeptide, the method including a step of producing a polypeptide having the function of horseshoe crab factor B using the cell according to the item [6].

[8]

A polypeptide obtained by the method according to the item [7].

[9]

A method for measuring an endotoxin, the method including steps of the following (1) and (2):

(1) a step of mixing the polypeptide according to the item [1], [2], or [8] with horseshoe crab factor C and a test sample; and (2) a step of measuring protease activity of the polypeptide.

[10]

A reagent for endotoxin measurement, including the polypeptide according to the item [1], [2], or [8] as a constituent component.

[11]

A kit for endotoxin measurement, including the polypeptide according to the item [1], [2] or [8], or the reagent according to the item [10], as a component part.

Advantageous Effects of Invention

According to the present invention, a horseshoe crab factor B variant having protease activity superior to that of the factor B itself can be provided. Furthermore, according to the present invention, a horseshoe crab factor B variant having thermal stability superior to that of the factor B itself.

DESCRIPTION OF EMBODIMENTS

Figure 1:
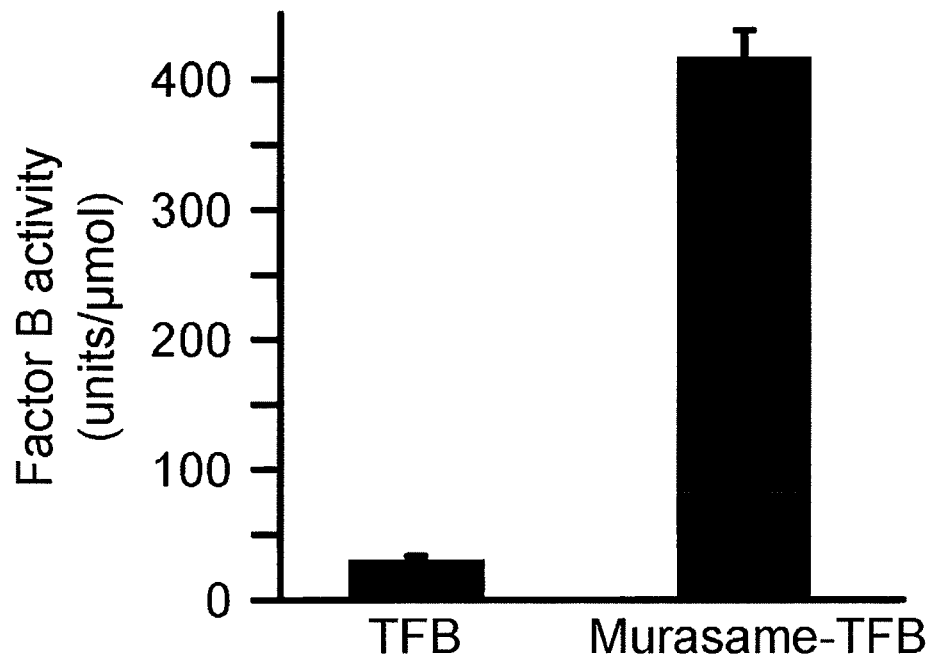
FIG. 1 is a diagram showing the specific activity (units/μmol) of *Tachypleus tridentatus* factor B (TFB) and a *Tachypleus tridentatus* factor B variant (Murasame-TFB).

The term "*Limulus* factor" as used for the present invention refers individually or collectively to factor C, factor B, and proclotting enzyme. Furthermore, the term "*Limulus* reagent" as used for the present invention refers to a reagent that includes any arbitrary *Limulus* factor as a constituent component and is used in a *Limulus* test.

According to the present invention, a series of reactions by which factor C that has come into contact with an endotoxin is autocatalytically changed to an activated form (activated factor C), and factor B is cleaved by the protease activity of the activated factor C and is thereby changed to activated factor B, may be referred to as "cascade reaction". Furthermore, according to the present invention, a series of reactions by which also includes, in addition to these series of reactions, a reaction by which proclotting enzyme is cleaved by the protease activity of the activated factor B and is thereby changed to a clotting enzyme, may also be referred to as "cascade reaction".

<1> Polypeptide of Present Invention

The polypeptide of the present invention is a polypeptide in which an amino acid residue at a particular site in the amino acid sequence of a polypeptide of horseshoe crab factor B is modified. The polypeptide of the present invention is specifically a polypeptide having an amino acid sequence in which the amino acid residue at the 193-position in the amino acid sequence of a polypeptide of horseshoe crab factor B is substituted with a cysteine (Cys) residue.

It is known that a sequence of twenty-three residues at the N-terminal in the amino acid sequence of a polypeptide of horseshoe crab factor B function as a signal sequence (Non Patent Literature 2). Therefore, in regard to the polypeptide of the present invention, those ordinarily skilled in the art can understand that in addition to a polypeptide in an embodiment of having the signal sequence, a polypeptide in an embodiment of not having the signal sequence (polypeptide in an embodiment of not having the twenty-three residues at the N-terminal) and a polypeptide in an embodiment of having another signal sequence (signal sequence other than the signal sequence inherently possessed by horseshoe crabs) also constitute one embodiment of the polypeptide of the present invention.

In the present invention, the type of horseshoe crab is not particularly limited. Regarding horseshoe crab, four kinds, namely, *Tachypleus tridentatus, Limulus polyphemus, Carcinoscorpius rotundicauda*, and *Tachypleus gigas*, are known, and these horseshoe crabs may be mentioned as examples of the horseshoe crab according to the present invention. The polypeptide of the present invention is, for example, a polypeptide having an amino acid sequence in which the amino acid residue at the 193-position in the amino acid sequence of a polypeptide of factor B for such a horseshoe crab is substituted with a cysteine (Cys) residue.

According to the present invention, it is preferable that the horseshoe crab is *Tachypleus tridentatus, Limulus polyphemus*, or *Carcinoscorpius rotundicauda*, and it is more preferable that the horseshoe crab is *Tachypleus tridentatus* or *Limulus polyphemus*.

The polypeptide of the present invention is specifically exemplified by a polypeptide represented by any one of the following (A) to (D).

(A) a polypeptide having an amino acid sequence represented by the following (A1) or (A2):

(A1) an amino acid sequence represented by amino acid numbers 1 to 400 of SEQ ID NO: 7; and (A2) an amino acid sequence represented by amino acid numbers 24 to 400 of SEQ ID NO: 7, (B) a polypeptide having an amino acid sequence represented by the following (B1) or (B2):

(B1) an amino acid sequence represented by amino acid numbers 1 to 400 of SEQ ID NO: 10; and (B2) an amino acid sequence represented by amino acid numbers 24 to 400 of SEQ ID NO: 10, (C) a polypeptide having an amino acid sequence including substitution, deletion, insertion, and/or addition of one amino acid residue or a plurality of amino acid residues in the amino acid sequence of the polypeptide represented by the item (A) or (B) (provided that the cysteine (Cys) residue at the 193-position is neither substituted nor deleted), the polypeptide having the function of horseshoe crab factor B, and (D) a polypeptide having an amino acid sequence of a fusion polypeptide in which a peptide tag is added to the polypeptide represented by any one of the items (A) to (C), the polypeptide having the function of horseshoe crab factor B.

The "polypeptide having an amino acid sequence" as used for the present invention includes the "polypeptide consisting of the amino acid sequence" as an embodiment.

The amino acid sequence set forth in SEQ ID NO: 7 for the item (A) is an amino acid sequence including substitution of the amino acid residue at the 193-position in the amino acid sequence of a polypeptide of *Tachypleus tridentatus* factor B (SEQ ID NO: 2) with a cysteine (Cys) residue.

The amino acid sequence set forth in SEQ ID NO: 10 for the item (B) is an amino acid sequence including substitution of the amino acid residue at the 193-position in the amino acid sequence of a polypeptide of *Limulus polyphemus* factor B (SEQ ID NO: 4) with a cysteine (Cys) residue.

The amino acid sequence of the polypeptide shown in the item (C) is an amino acid sequence including substitution, deletion, insertion, and/or addition of one amino acid residue or a plurality of amino acid residues in the amino acid sequence of the polypeptide shown in the item (A) or (B), with the cysteine (Cys) residue at the 193-position being neither substituted nor deleted (the Cys residue at the 193-position is conserved). Meanwhile, the cysteine (Cys) residue at the 193-position represents the position of the cysteine (Cys) residue to be conserved in the amino acid sequence set forth in SEQ ID NO: 7 or SEQ ID NO: 10. Therefore, the cysteine (Cys) residue that is conserved in an amino acid sequence including substitution, deletion, insertion, and/or addition of one amino acid residue or a plurality of amino acid residues in the amino acid sequence of the polypeptide represented by the item (A) or (B) (that is, the amino acid sequence represented by the item (C)) is a cysteine (Cys) residue at a position corresponding to the cysteine (Cys) residue at the 193-position in the alignment of the amino acid sequence with the original amino acid sequence (amino acid sequence of the polypeptide represented by the item (A) or (B)).

The term "a plurality" as used for the item (C) means the number (total number) of amino acid residues to the extent that even if the polypeptide is subjected to substitution, deletion, insertion, and/or addition, the polypeptide does not lose the function of horseshoe crab factor B. The term "a plurality" may be, for example, a number of preferably 10% or less, more preferably 5% or less, even more preferably 2% or less, and particularly preferably 1% or less, with respect to the total number of amino acid residues that constitute the polypeptide.

Therefore, in the case of the amino acid sequence of the polypeptide represented by the item (A1) or (B1), since the total number of amino acid residues is 400, "a plurality" may be preferably 2 to 40, more preferably 2 to 20, even more preferably 2 to 8, and particularly preferably 2 to 4. Furthermore, in the case of the amino acid sequence of the polypeptide represented by the item (A2) or (B2), since the total number of amino acid residues is 377, "a plurality" may be preferably 2 to 37, more preferably 2 to 18, even more preferably 2 to 7, and particularly preferably 2 to 3. The term "a plurality" as used for the item (C) may be, as the number of specific individuals, an integer such as two, three, four, five, six, seven, or eight.

The terms "substitution, deletion, insertion, and/or addition" as used for the item (C) are, for example, conservative mutations. A representative example of conservative mutation is conservative substitution. Conservative mutation is a mutation resulting from the following: in a case in which the site of substitution is an aromatic amino acid, substitution occurs between Phe, Trp, and Tyr; in a case in which the site of substitution is a hydrophobic amino acid, substitution occurs between Leu, Ile, and Val; in a case in which the site of substitution is a polar amino acid, substitution occurs between Gln and Asn; in a case in which the site of substitution is a basic amino acid, substitution occurs between Lys, Arg, and His; in a case in which the site of substitution is an acid amino acid, substitution occurs between Asp and Glu; and in a case in which the site of substitution is an amino acid having a hydroxyl group, substitution occurs between Ser and Thr. Specific examples of a substitution that is regarded as conservative substitution include substitution of Ala with Ser or Thr; substitution of Arg with Gln, His, or Lys; substitution of Asn with Glu, Gln, Lys, His, or Asp; substitution of Asp with Asn, Glu, or Gln; substitution of Cys with Ser or Ala; substitution of Gln with Asn, Glu, Lys, His, Asp, or Arg; substitution of Glu with Gly, Asn, Gln, Lys, or Asp; substitution of Gly with Pro; substitution of His with Asn, Lys, Gln, Arg, or Tyr; substitution of Ile with Leu, Met, Val, or Phe; substitution of Leu with Ile, Met, Val, or Phe; substitution of Lys with Asn, Glu, Gln, His, or Arg; substitution of Met with Ile, Leu, Val, or Phe; substitution of Phe with Trp, Tyr, Met, Ile, or Leu; substitution of Ser with Thr or Ala; substitution of Thr with Ser or Ala; substitution of Trp with Phe or Tyr; substitution of Tyr with His, Phe, or Trp; and substitution of Val with Met, Ile, or Leu.

The polypeptide represented by the item (C) may be, for example, a polypeptide having a similarity of preferably 90% or higher, more preferably 95% or higher, even more preferably 98% or higher, and particularly preferably 99% or higher, to the amino acid sequence of the polypeptide represented by the item (A) or (B), the polypeptide having the function of horseshoe crab factor B (provided that the cysteine (Cys) residue at the 193-position may be conserved). Meanwhile, since the term "similarity" as used herein is a concept including "identity", similarity may be replaced with identity and can be applied to suitable embodiments of the polypeptide.

The polypeptide represented by the item (C) may have any arbitrary amino acid residue substituted or deleted in the amino acid sequence of the polypeptide represented by the item (A) or (B) as long as the cysteine (Cys) residue at the 193-position is neither substituted nor deleted (Cys residue at the 193-position is conserved). However, it is preferable that other Cys residues that are conserved (exist at the same position) between the amino acid sequence of a polypeptide of *Tachypleus tridentatus* factor B (SEQ ID NO: 2) and the amino acid sequence of a polypeptide of *Limulus polyphemus* factor B (SEQ ID NO: 4) are also conserved (neither substituted nor deleted). Specifically, it is preferable for the polypeptide represented by the item (C) that the Cys residues at the 112-position, 177-position, 193-position, 260-position, 307-position, 329-position, 340-position, and 368-position in the amino acid sequence of the polypeptide represented by the item (A) or (B) are conserved (neither substituted nor deleted).

The "peptide tag" as used for the item (D) means a peptide that is added to the polypeptide in order to facilitate detection or purification. The length and amino acid sequence of the "peptide tag" are not particularly limited as long as a fusion polypeptide in which a peptide tag is added to the polypeptide represented by any one of the items (A) to (C) has the function of horseshoe crab factor B. Examples of such a peptide tag include 6×His peptide (His tag), FLAG peptide (FLAG tag), c-myc peptide (myc tag), protein A, maltose-binding protein (MBP), and glutathione-S-transferase (GST).

The peptide tag may be added directly to the polypeptide represented by any one of the items (A) to (C), or may be added to the polypeptide through any arbitrary linker. The "linker" as used herein may be any peptide linker including an arbitrary amino acid sequence. The length and amino acid sequence of the "peptide linker" as used herein are not particularly limited, similarly to the case of the peptide tag, as long as the fusion polypeptide in which a peptide tag is added to the polypeptide represented by any one of the items (A) to (C) has the function of horseshoe crab factor B.

The peptide tag may be added to, for example, the N-terminal and/or the C-terminal of the polypeptide. The peptide tag may be added to the N-terminal side of the polypeptide only, may be added to the C-terminal side only, or may be added to both of the terminals. One kind of peptide tag may be added to the polypeptide, or two or more kinds of peptide tags may also be added. Furthermore, regarding the various kinds of peptide tags to be added to the polypeptide, one peptide tag from each kind may be independently added, or two or more peptide tags from each kind may be independently added.

The "function of horseshoe crab factor B" according to the present invention means the function as a protease precursor possessed by horseshoe crab factor B. The "function of horseshoe crab factor B" specifically means the function of coming into contact with activated factor C to be changed to an activated form (activated factor B) and exhibiting the protease activity.

The function of horseshoe crab factor B is, for example, a function of coming into contact with activated factor C to be changed to an activated form (activated factor B), cleaving a proclotting enzyme, and thereby changing the proclotting enzyme to a clotting enzyme. Furthermore, the function of horseshoe crab factor B is, for example, a function of coming into contact with activated factor C to be changed to an activated form (activated factor B), cleaving a substrate for detection, which serves as a substrate for the activated factor B, and thereby releasing a marker substance. In regard to the factor C, proclotting enzyme, and substrate for detection as used herein, for example, embodiments described in connection with the measurement method of the present invention that will be described below can be suitably used.

Whether a polypeptide has the function of horseshoe crab factor B can be determined by, for example, evaluating whether the polypeptide exhibits protease activity when brought into contact with activated factor C. Specifically, whether a polypeptide has the function of horseshoe crab factor B can be determined by, for example, the method described in <Example 2> or <Example 5> that will be described below.

Furthermore, whether a polypeptide has the function of horseshoe crab factor B can also be determined by, for example, evaluating, in a case in which a *Limulus* reagent configured to include the polypeptide in combination with factor C is used, whether a cascade reaction proceeds when the *Limulus* reagent is allowed to co-exist with an endotoxin.

Furthermore, whether a polypeptide has the function of horseshoe crab factor B can be determined by, for example, evaluating, in a case in which a *Limulus* reagent configured to include the polypeptide in combination with factor C and a proclotting enzyme is used, whether a cascade reaction proceeds when the *Limulus* reagent is allowed to co-exist with an endotoxin.

Therefore, the polypeptide represented by the item (C) can be obtained by, for example, employing the function of horseshoe crab factor B as a marker, and selecting a site where substitution, deletion, insertion, and/or addition of one amino acid residue or a plurality of amino acid residues can be carried out without losing the function of horseshoe crab factor B, from the amino acid sequence represented by the item (A) or (B). Furthermore, the polypeptide represented by the item (D) can be obtained by, for example, employing the function of horseshoe crab factor B as a marker and selecting a polypeptide to which a peptide tag can be added without losing the function of horseshoe crab factor B, from the polypeptides represented by any of the items (A) to (C).

An embodiment of the polypeptide of the present invention is a polypeptide that exhibits protease activity that is superior to that of horseshoe crab factor B itself. Horseshoe crab factor B itself is specifically a polypeptide including the same amino acid sequence as that of naturally occurring horseshoe crab factor B. Horseshoe crab factor B itself is more specifically, for example, a polypeptide including an amino acid sequence in which the amino acid residue at the 193-position in the amino acid sequence represented by the item (A) or (B) is substituted with an alanine (Ala) residue (polypeptide including the amino acid sequence set forth in SEQ ID NO: 2 or SEQ ID NO: 4). The polypeptide of the present invention may be a polypeptide characterized in that, for example, the protease activity (specific activity) exhibited when the polypeptide comes into contact with activated factor C to be changed to an activated form (activated factor B) is two times or more, preferably 5 times or more, and more preferably 10 times or more, compared to horseshoe crab factor B itself. Furthermore, the polypeptide of the present invention may be a polypeptide characterized in that, for example, the protease activity (specific activity) exhibited when the polypeptide comes into contact with activated factor C to be changed to an activated form (activated factor B) is 80 units/μmol or higher, preferably 200 units/μmol or higher, more preferably 300 units/μμmol or higher, and particularly preferably 400 units/mol or higher. Here, 1 unit corresponds to the protease activity capable of cleaving 1 μmol of a substrate (substrate for detection) for 1 minute at 37° C. The measurement conditions for the enzyme activity (units/μmol) may be, for example, the conditions described in <Example 2> or <Example 5>.

An embodiment of the polypeptide of the present invention is a polypeptide having thermal stability superior to that of horseshoe crab factor B itself. The polypeptide of the present invention may be, for example, a polypeptide characterized in that the protease activity (specific activity) exhibited when the polypeptide that has been heated for 2 minutes at 50° C. is brought into contact with activated factor C to be changed to an activated form (activated factor B) is 50% or higher, preferably 70% or higher, and more preferably 80% or higher, compared to the activity of the polypeptide that has not been heated. Furthermore, the polypeptide of the present invention may be, for example, a polypeptide characterized in that even after being heated for 2 minutes at 60° C., 70° C., 80° C., or 90° C., the polypeptide does not lose the function of horseshoe crab factor B.

The polypeptide of the present invention may be, for example, a polypeptide characterized in that the protease activity (specific activity) exhibited when the polypeptide that has been heated for 2 minutes at 60° C. is brought into contact with activated factor C to be changed to an activated form (activated factor B) is 30% or higher, preferably 50% or higher, and more preferably 70% or higher, compared to the activity of the polypeptide that has not been heated. Furthermore, the polypeptide of the present invention may be, for example, a polypeptide characterized in that the protease activity (specific activity) exhibited when the polypeptide that has been heated for 2 minutes at 90° C. is brought into contact with activated factor C to be changed to an activated form (activated factor B) is 20% or higher, preferably 30% or higher, and more preferably 40% or higher, compared to the activity of the polypeptide that has not been heated.

The protease activity of the activated factor B can be measured by, for example, the method described in <Example 2> or <Example 5> that will be described below, by which the protease activity of factor B (activated factor B) that has been activated by being brought into contact with activated factor C is measured.

Here, the amino acid sequence of the polypeptide is homologous to the *Limulus* factor of horseshoe crab, and high similarity is found between species. The similarity of amino acid sequences can be calculated using well-known computer software programs, and for example, the similarity can be calculated using the algorithm BLAST (Karlin, S., Altschul, SF. (1993) Proc. Natl. Acad. Sci. U.S.A., 90, 5873-7) or the algorithm FASTA (Pearson, W R. (1990) Methods. Enzymol. 183, 63-98). Specifically, the similarity of amino acid sequences can be calculated using, for example, GENETYX (manufactured by Genetyx Corporation).

For example, the polypeptide of *Tachypleus tridentatus* factor B (SEQ ID NO: 2, NCBI Accession No.: BAA03528.1) and the polypeptide of *Limulus polyphemus* factor B (SEQ ID NO: 4, NCBI Accession No.: XP_013784210.1) have a similarity of 98.5%.

Furthermore, for example, the polypeptide of *Tachypleus tridentatus* factor C (SEQ ID NO: 12, NCBI Accession No.: BAA14315.1) and the polypeptide of *Limulus polyphemus* factor C (SEQ ID NO: 14) have a similarity of 99.5%. The polypeptide of *Tachypleus tridentatus* factor C and the polypeptide of *Carcinoscorpius rotundicauda* factor C (SEQ ID NO: 16, NCBI Accession No. AAB34361.1) have a similarity of 99.8%. The polypeptide of *Limulus polyphemus* factor C and the polypeptide of *Carcinoscorpius rotundicauda* factor C have a similarity of 99.4%.

Furthermore, for example, the polypeptide of *Tachypleus tridentatus* proclotting enzyme (SEQ ID NO: 18, NCBI Accession No.: AAA30094.1) and the polypeptide of *Limulus polyphemus* proclotting enzyme (SEQ ID NO: 20, NCBI Accession No.: XP 013783518.1) have a similarity of 96.0%.

Therefore, the technology of the present invention is verified by modification of the respective polypeptides of *Tachypleus tridentatus* factor B and *Limulus polyphemus* factor B in the Examples described below; however, a person ordinarily skilled in the art can understand that the technology of the present invention is also applicable to the polypeptides of other horseshoe crab factors B. For example, the amino acid sequences of the respective polypeptides of *Carcinoscorpius rotundicauda* factor B and *Tachypleus gigas* factor B, and the base sequences encoding the polypeptides are still not known; however, those ordinarily skilled in the art can understand that the technology of the present invention is also applicable to the polypeptides of these factors B.

The polypeptide of the present invention may be an embodiment composed of the polypeptide of the present invention or may be an embodiment including other components. The "other components" as used herein are not particularly limited as long as they are not components that cause the polypeptide of the present invention to lose the function. Examples of the "other components" include a buffer agent, an alkali metal salt, an alkaline earth metal salt, and a surfactant. Examples of the "other components" also include components other than the polypeptide of the present invention (a nucleic acid, a protein, a carbohydrate, a lipid, and the like), the components being derived from cells that produce the polypeptide of the present invention.

The polypeptide of the present invention may have any arbitrary form. The polypeptide of the present invention may be, for example, in a solid form such as a freeze-dried product, or may be in a liquid form in a state of being dissolved in an arbitrary solvent such as an aqueous solvent.

The weight concentration occupied by the polypeptide of the present invention in the polypeptide of the present invention may be, for example, 0.001% or more, 0.01% or more, 0.1% or more, 1% or more, 5% or more, 10% or more, 25% or more, or 50% or more. Furthermore, the weight concentration occupied by the polypeptide of the present invention in the polypeptide of the present invention may be, for example, 100% or less, 75% or less, 50% or less, 25% or less, 10% or less, 5% or less, or 1% or less.

The polypeptide of the present invention can be produced by any known technique based on the description of the present specification. The polypeptide of the present invention can be produced by, for example, a genetic engineering technique. Specifically, the polypeptide of the present invention can be produced by, for example, the production method of the present invention that will be described below. The polypeptide of the present invention may be the culture fluid itself obtainable by culturing cells according to the production method of the present invention, or may be a fraction obtained by purifying this culture fluid to a desired extent.

<2> Nucleic Acid of Present Invention

The nucleic acid of the present invention is a nucleic acid encoding the polypeptide of the present invention. The nucleic acid of the present invention is not particularly limited as long as it is a nucleic acid encoding the polypeptide of the present invention. The nucleic acid of the present invention includes all nucleic acids having base sequences that vary due to degeneracy (degeneration) of genetic codes (codons) but encode the same polypeptide, as long as the nucleic acids are nucleic acids encoding the polypeptide of the present invention. The term "nucleic acid" as used herein includes DNA and RNA.

The nucleic acid of the present invention may be a double-stranded nucleic acid or a single-stranded nucleic acid. In a case in which the nucleic acid of the present invention is a double-stranded nucleic acid, the nucleic acid may also be a hybrid strand formed from a DNA and an RNA. Furthermore, since the nucleic acid of the present invention is a nucleic acid encoding the polypeptide of the present invention, the nucleic acid of the present invention may be a nucleic acid having a sequence of an intron within the region encoding the polypeptide of the present invention, or may be a nucleic acid that does not have a sequence of an intron in that region. Furthermore, the nucleic acid of the present invention may be an mRNA (mRNA precursor or a mature mRNA) or may be a DNA (cDNA) synthesized by a reverse transcription reaction from an mRNA. The nucleic acid of the present invention may be an isolated nucleic acid.

The nucleic acid of the present invention is, for example, a DNA having a base sequence in which the base of base number 577 in a base sequence of a cDNA encoding a polypeptide of horseshoe crab factor B is substituted with thymine (T), the base of base number 578 is substituted with guanine (G), and the base of base number 579 is substituted with thymine (T) or cytosine (C), the nucleic acid being a DNA encoding a polypeptide having the function of horseshoe crab factor B. Specifically, the nucleic acid of the present invention may be, for example, a DNA represented by any one of the following (a) to (d).

(a) a DNA having a base sequence represented by any one of the following (a1) to (a4): (a1) a base sequence represented by base numbers 1 to 1200 of SEQ ID NO: 5;

(a2) a base sequence represented by base numbers 70 to 1200 of SEQ ID NO: 5;

(a3) a base sequence represented by base numbers 1 to 1200 of SEQ ID NO: 6; and (a4) a base sequence represented by base numbers 70 to 1200 of SEQ ID NO: 6, (b) a DNA having a base sequence represented by any one of the following (b1) to (b4):

(b1) a base sequence represented by base numbers 1 to 1200 of SEQ ID NO: 8;

(b2) a base sequence represented by base numbers 70 to 1200 of SEQ ID NO: 8;

(b3) a base sequence represented by base numbers 1 to 1200 of SEQ ID NO: 9; and (b4) a base sequence represented by base numbers 70 to 1200 of SEQ ID NO: 9, (c) a DNA hybridizing with a DNA including a base sequence complementary to the DNA represented by the item (a) or (b) under stringent conditions (provided that the bases represented by base numbers 577 to 579 are conserved), the DNA encoding a polypeptide having the function of horseshoe crab factor B, and (d) a DNA having a base sequence of a fusion DNA in which a peptide tag-encoding DNA is added to the DNA represented by any one of the items (a) to (c), the DNA encoding a polypeptide having the function of horseshoe crab factor B.

The "nucleic acid having a base sequence" as used for the present invention includes this "nucleic acid consisting of a base sequence" as an embodiment. Therefore, the "DNA having a base sequence" as used for the present invention includes this "DNA consisting of a base sequence" as an embodiment.

The base sequence represented by SEQ ID NO: 5 for the item (a) is a base sequence in which, in a DNA (SEQ ID NO: 1) encoding a polypeptide of *Tachypleus tridentatus* factor B, the base of base number 577 is substituted with thymine (T), the base of base number 578 is substituted with guanine (G), and the base of base number 579 is substituted with thymine (T).

The base sequence represented by SEQ ID NO: 6 for the item (a) is a base sequence in which, in the base sequence of a DNA (SEQ ID NO: 1) encoding a polypeptide of *Tachypleus tridentatus* factor B, the base of base number 577 is substituted with thymine (T), and the base of base number 578 is substituted with guanine (G).

The base sequence represented by SEQ ID NO: 8 for the item (b) is a base sequence in which, in the base sequence of a DNA (SEQ ID NO: 3) encoding a polypeptide of *Limulus polyphemus* factor B, the base of base number 577 is substituted with thymine (T), and the base of base number 578 is substituted with guanine (G).

The base sequence represented by SEQ ID NO: 9 for the item (b) is a base sequence in which, in the base sequence of a DNA (SEQ ID NO: 3) encoding a polypeptide of *Limulus polyphemus* factor B, the base of base number 577 is substituted with thymine (T), the base of base number 578 is substituted with guanine (G), and the base of base number 579 is substituted with cytosine (C).

The "stringent conditions" employed for the item (c) mean conditions in which a specific hybrid is formed while a non-specific hybrid is not formed. Therefore, the "stringent conditions" as used herein mean, for example, conditions in which a specific hybrid is formed for a DNA including a base sequence that is complementary to the DNA represented by the item (a) or (b). An example of the stringent conditions is conditions in which DNAs having high similarity, for example, DNAs having a similarity of 80% or higher, preferably 90% or higher, more preferably 95% or higher, even more preferably 98% or higher, and particularly preferably 99% or higher, hybridize with each other, and DNAs having a similarity lower than that do not hybridize with each other. An example of such conditions is, for example, conditions in which DNAs are washed once, preferably two or three times, at a salt concentration and a temperature corresponding to 60° C., 1×SSC, 0.1% SDS; preferably 60° C., 0.1×SSC, 0.1% SDS; and more preferably 68° C., 0.1×SSC, 0.1% SDS, which are conditions for washing in conventional Southern hybridization. Furthermore, another example of such conditions is conditions in which DNAs are hybridized at 42° C. in a solution including 50% formamide, 4×SSC, 50 mM HEPES-NaOH (pH 7.0), 10×Denhardt's solution, and 100 µg/mL salmon sperm DNA, the hybrid is washed at room temperature with a solution including 2×SSC and 0.1% SDS, and the hybrid is further washed at 50° C. with a solution including 0.1×SSC and 0.1% SDS (Sambrook J, et al., Molecular Cloning: A Laboratory Manual, Second Edition, Cold Spring Harbor Laboratory Press (1989)).

The DNA represented by the item (c) can be produced by, for example, performing substitution, deletion, insertion, and/or addition of a nucleic acid residue (hereinafter, collectively referred to as "introduction of mutation") for the DNA represented by the item (a) or (b), in a region other than base numbers 577 to 579 of the same base sequence. The "introduction of mutation" as used herein can be carried out by, for example, any known method.

Regarding the method of performing the "introduction of mutation", a method of using a restriction enzyme and T4DNA ligase may be mentioned as an example. That is, a DNA having a mutation introduced therein can be obtained by subjecting the two terminals of a DNA fragment having a mutation introduced therein, to limited digestion using a restriction enzyme; mixing the resultant with a vector into which a DNA represented by the item (a) or (b) has been subcloned, the DNA having been subjected to limited digestion using the same restriction enzyme; and then subjecting the two to ligation using T4DNA ligase. The "DNA fragment having a mutation introduced therein" can be obtained by, for example, a PCR reaction using oligonucleotides into which such a mutation has been introduced, as primers.

Furthermore, another example of the method for implementing the "introduction of mutation" is a site-specific mutation introduction method. Examples of the site-specific mutation introduction method include methods of using a PCR reaction (Higuchi, R. (1989) in PCR technology (Erlich, H. A., ed.) Stockton Press, New York, pp. 61-70; Carter, P. (1987) Methods Enzymol., 154, 382-403), and methods of using phages (Kramer, W., Fritz, H. J. (1987) Methods Enzymol., 154, 350-67; Kunkel, T. A., Roberts, J. D., Zakour, R. A. (1987) Methods Enzymol., 154, 367-82). Specifically, the site-specific mutation introduction method can be carried out by utilizing, for example, KOD-Plus-Mutagenesis Kit (manufactured by Toyobo Co., Ltd.).

The DNA represented by the item (c) may have a mutation introduced into any arbitrary site in the base sequence of a DNA represented by the item (a) or (b) as long as no mutation is introduced into the sites represented by base numbers 577 to 579 (bases represented by base numbers 577 to 579 are conserved); however, it is preferable that the DNA represented by the item (c) is a DNA encoding a polypeptide in which other Cys residues that are conserved (exist at the same positions) between the amino acid sequence of a polypeptide of *Tachypleus tridentatus* factor B (SEQ ID NO: 2) and the amino acid sequence of a polypeptide of *Limulus polyphemus* factor B (SEQ ID NO: 4) are also conserved. (neither substituted nor deleted). In regard to the DNA represented by the item (c), specifically, it is preferable that base sequences (codons) represented by base numbers 334 to 336, base numbers 529 to 531, base numbers 577 to 579, base numbers 778 to 780, base numbers 919 to 921, base numbers 985 to 987, base numbers 1018 to 1020, and base numbers 1102 to 1104 are conserved (TGT or TGC).

The embodiment of the "peptide tag" for the item (d) is the same as the embodiment concerning the "<1> Polypeptide of present invention" described above. Therefore, as long as a polypeptide encoded by a DNA has the function of horseshoe crab factor B, a fusion DNA in which a peptide tag-encoding DNA is added to a DNA represented by the item (a), (b), or (c), is also included as an example of the nucleic acid of the present invention.

Such a "fusion DNA in which a peptide tag-encoding DNA is added" can be produced by, for example, a method of using a restriction enzyme and T4DNA ligase. That is, the fusion DNA can be obtained by subjecting the two terminals of a DNA fragment that encodes a peptide tag, to limited digestion using a restriction enzyme; mixing the resultant with a vector into which a DNA represented by any one of the items (a) to (c) has been subcloned, the DNA having been subjected to limited digestion using the same restriction enzyme; and then subjecting the two to ligation using T4DNA ligase.

Furthermore, such a "fusion DNA in which a peptide-tag encoding DNA is added" can also be obtained by, for example, a PCR reaction that uses oligonucleotides having the base sequence of the peptide tag-encoding DNA as primers, and uses the DNA represented by any one of the items (a) to (c) as a template.

The polypeptide encoded by the nucleic acid of the present invention can be produced by, for example, the production method of the present invention that will be described below. Regarding the production method of the present invention, specifically, a method of using a mammalian cell as described in <Example 1> or <Example 4> that will be described below may be mentioned as an example.

The polypeptide encoded by the nucleic acid of the present invention is a polypeptide having the function of horseshoe crab factor B. The definition for the "function of horseshoe crab factor B" as used herein is as described in connection with the above section "<1> Polypeptide of present invention". Therefore, by determining whether the polypeptide encoded by the nucleic acid has the function of horseshoe crab factor B according to the method described in the section "<1> Polypeptide of present invention", the DNA represented by the item (c) or (d) can be selected.

The nucleic acid of the present invention can be produced by any known technique, based on the description of the present specification. The nucleic acid of the present invention can be produced by a genetic engineering technique. Specifically, the nucleic acid of the present invention can be produced by, for example, the PCR reaction described in <Example 1> or <Example 4> that will be described below. Furthermore, the nucleic acid of the present invention can also be produced by, for example, chemical total synthesis of the base sequence.

<3> Vector of Present Invention

The vector of the present invention is a vector retaining the nucleic acid of the present invention. The type or number of the nucleic acid of the present invention retained by the vector of the present invention is not particularly limited. One kind of the nucleic acid of the present invention may be retained by the vector of the present invention, or two or more kinds of the nucleic acids of the present invention may be retained. Furthermore, regarding various kinds of the nucleic acids of the present invention to be retained by the vector of the present invention, one nucleic acid (one copy) from each kind may be independently retained, or two or more nucleic acids (two copies) from each kind may be independently retained.

The "vector" as used herein means a nucleic acid molecule used for the amplification of the nucleic acid of the present invention and/or the expression of the polypeptide encoded by the nucleic acid of the present invention. According to the present invention, the vector is not particularly limited as long as the vector enables amplification of the nucleic acid of the present invention or the vector, or expression of the polypeptide that is encoded by the nucleic acid of the present invention in a cell into which this vector is introduced. Examples of such a vector include a phage, a plasmid, and a virus.

The vector can be appropriately selected according to various conditions such as the kind of cell into which this vector is introduced, and the desired amount of expression of the polypeptide encoded by the nucleic acid of the present invention. For example, in a case in which a prokaryotic cell such as a bacterial cell is utilized as the cell, a phage or a plasmid can be suitably utilized as the vector. Furthermore, in a case in which a eukaryotic cell such as an insect cell or a mammalian cell is utilized as the cell, a plasmid or a virus can be suitably utilized as the vector.

Examples of the plasmid that can be utilized in mammalian cells include pCA7 (Takeda, M., Ohno, S., Seki, F., Nakatsu, Y., Tahara, M., Yanagi, Y. (2005) J. Virol. 79, 14346-54) and pCI-neo (manufactured by Promega Corporation). Examples of the plasmid that can be utilized in insect cells include pIZ-V5 (manufactured by Life Technologies Corp.). Examples of the plasmid that can be utilized in bacterial cells include pBlue Script II SK(+) (manufactured by Agilent Technologies, Inc.) and pET (manufactured by Takara Bio, Inc.).

Examples of the virus that can be utilized in mammalian cells include animal viruses. Examples of the animal viruses include Sendai virus. Examples of the virus that can be utilized in insect cells include baculovirus. Examples of the baculovirus include nuclear polyhedrosis virus (NPV).

Examples of the phage that can be utilized in bacterial cells include bacteriophage. Examples of the bacteriophage include Lambda phage (X phage) and T4 phage.

The vector of the present invention can be obtained by, for example, introducing the nucleic acid of the present invention into a vector. Introduction of the nucleic acid of the present invention into a vector can be carried out by a conventional method.

An example of a method for introducing the nucleic acid of the present invention into a vector may be a method of utilizing a multiple cloning site carried by the vector. The vector of the present invention can be obtained by, for example, selecting any two restriction enzyme sites from the restriction enzyme sites existing in a multiple cloning site carried by the vector, and subjecting the vector and the nucleic acid of the present invention to limited digestion using these restriction enzymes and then to ligation. Regarding the nucleic acid of the present invention for this use application, for example, a DNA obtainable by a PCR reaction that uses oligonucleotides having a restriction enzyme site added to the 5'-terminal-side as primers, and uses the nucleic acid of the present invention as a template, can be used. Furthermore, for example, the vector of the present invention can also be obtained by performing the introduction of a mutation such that the amino acid residue at the 193-position in the amino acid sequence of a polypeptide of horseshoe crab factor B is changed to a cysteine (Cys) residue, by an inverse PCR reaction using, as a template, a vector in which a DNA encoding the polypeptide of horseshoe crab factor B has been inserted. Specifically, an example of the method for producing the vector of the present invention is the method described in <Example 1> or <Example 4> that will be described below.

<4> Cell of Present Invention

The cell of the present invention is a cell that retains the nucleic acid of the present invention and/or the vector of the present invention (hereinafter, collectively referred to as "vector or the like of the present invention"). Since the vector of the present invention is a vector having the nucleic acid of the present invention, the cell that retains the vector of the present invention also corresponds to a cell that retains the nucleic acid of the present invention.

The cell of the present invention can be obtained by, for example, introducing the vector or the like of the present invention into a cell. Therefore, the cell of the present invention can be obtained by, for example, transforming (transducing) a cell using the vector or the like of the present invention. The cell according to the present invention is not particularly limited as long as the cell is capable of having the vector or the like of the present invention introduced therein, or capable of being transformed using this. It is preferable that the cell according to the present invention is an isolated cell.

The type or number of the vector or the like of the present invention retained by the cell of the present invention is not particularly limited. One kind of the vector or the like of the present invention may be retained by the cell of the present invention, or two or more kinds of the vectors or the like of the present invention may be retained by the cell. Furthermore, regarding various kinds of the vectors of the present invention to be retained by the cell of the present invention, one vector (one copy) from each kind may be independently retained, or two or more vectors (two copies) from each kind may be independently retained.

The cell of the present invention may retain the vector or the like of the present invention intrachromosomally, may retain the vector or the like of the present invention extrachromosomally, or may retain the vector or the like of the present invention both intrachromosomally and extrachromosomally. Specifically, the cell of the present invention may be a cell having the vector or the like of the present invention introduced therein, or a cell transformed using this.

In regard to the cell of the present invention, the "cell" is, for example, a host cell. The "host cell" as used herein means a cell used as a host for amplifying the vector or the like of the present invention, and/or as a host for expressing the polypeptide of the present invention encoded by the vector or the like of the present invention.

The cell according to the present invention can be selected as appropriate according to the purpose of using the vector or the like of the present invention.

For example, in a case in which amplification of the vector or the like of the present invention is purported, the cell is preferably a prokaryotic cell, and specifically, the cell is preferably a bacterial cell. Above all, it is preferable that the cell is *Escherichia coli* cell. Examples of *Escherichia coli* include strain JM109 and strain DH5a.

Furthermore, for example, in a case in which expression of the polypeptide encoded by the vector or the like of the present invention is purported, for example, a cell that is usually used in order to express a polypeptide that is not inherently possessed by the cell can be used as the cell. Such a cell is, for example, preferably a eukaryotic cell, and it is preferable that the cell is specifically a mammalian cell, an insect cell, a plant cell, or a yeast cell. The eukaryotic cell is preferably a mammalian cell or an insect cell, and more preferably a mammalian cell.

It is preferable that the mammalian cell is a cell of a primate or a cell of a rodent. Examples of the primate include human being, monkey, and chimpanzee. An example of the cell of a primate is a human cell. A specific example of the human cell is a human embryonic kidney cell-derived cell strain (HEK cell). An example of the HEK cell is a HEK293 cell. An example of the HEK293 cell is a HEK293S cell. An example of the HEK293S cell is HEK293S GnTI⁻ cell. Furthermore, examples of the rodent include hamster, mouse, rat, and guinea pig. An example of the cell of a rodent is a hamster cell. An example of the hamster is a Chinese hamster cell. An example of the Chinese hamster cell is a CHO cell. Examples of the CHO cell include CHO DG44 cell, CHO-K1 cell, and CHO—S cell.

Introduction of a nucleic acid into a cell can be carried out by a conventional method. The method for introducing a nucleic acid into a cell in the present invention is not particularly limited as long as it is a method capable of introducing the vector or the like of the present invention into a cell. Specific examples of the method for introducing a nucleic acid into a cell include a calcium phosphate method, a lipofection method, a DEAE dextran method, an electroporation method, and a microinjection method. Transformation of the cell can be carried out by, for example, the method described in <Example 1> or <Example 4> that will be described below.

<5> Production Method of Present Invention

The production method of the present invention is a method for producing the polypeptide of the present invention using the cell of the present invention. The production method of the present invention is specifically a method for producing a polypeptide, the method including a step of producing the polypeptide of the present invention by using the cell of the present invention (hereinafter, referred to as "production step"). The production step is, for example, a step of expressing the polypeptide of the present invention by culturing the cell of the present invention.

The conditions for culturing the cell of the present invention in the production method of the present invention (hereinafter, simply referred to as "culture conditions") are not particularly limited as long as the conditions are conditions capable of exhibiting the polypeptide of the present invention in a cell. The culture conditions can be selected as appropriate according to various conditions such as the type of the cell and the desired amount of expression of the polypeptide of the present invention encoded by the vector or the like of the present invention. Culture of cells can be carried out by, for example, using a medium that is usually used for the culture of the relevant cell. Regarding the culture conditions, specifically, the conditions described in <Example 1> or <Example 4> that will be described below may be mentioned as an example.

The production method of the present invention may further include another step as long as the method includes the production step. The "other step" as used herein is, for example, a step of collecting the polypeptide of the present invention produced in the production step (hereinafter, referred to as "collection step"). The "collection step" as used herein is a step of obtaining a fraction including the polypeptide of the present invention from the culture fluid of the cell.

For example, in a case in which the polypeptide of the present invention is expressed in a form of being secreted extracellularly, the collection step may be a step of collecting the culture fluid itself, the supernatant obtained after centrifugation, or a fraction obtainable after purifying these by subjecting to a column or the like, as the polypeptide of the present invention.

Furthermore, for example, in a case in which the polypeptide of the present invention is expressed in a form of being accumulated in the cell, the collection step may be a step of collecting the cell itself, a crushed product (cell debris) obtainable by crushing the cell or an extract, or a fraction obtainable after purifying these by subjecting to a column or the like, as the polypeptide of the present invention.

The term "crushing" in the above description can be carried out by a method selected as appropriate according to the type of the cell. Examples of the method of crushing include a method of performing homogenization, a method performing an ultrasonic treatment, a method of performing freezing and thawing, and a method of adding a surfactant. These techniques used for crushing can be used in combination as appropriate.

The term "purification" in the above description can be carried out by a technique that is usually used for the purification of polypeptides. Examples of such a method include ammonium sulfate precipitation, gel permeation chromatography, ion exchange chromatography, hydrophobic interaction chromatography, hydroxyapatite chromatography, and affinity chromatography. These techniques can be used in combination as appropriate.

Whether the polypeptide of the present invention is included in the fraction thus collected can be determined by, for example, measuring the presence or absence of a polypeptide having the function of horseshoe crab factor B according to the method described in the section "<1> Polypeptide of present invention". Furthermore, whether the polypeptide of the present invention is included in the fraction thus collected can be determined by, for example, a method of using an antibody that binds to the polypeptide of the present invention.

<6> Measurement Method of Present Invention

The measurement method of the present invention is a method of performing the measurement of an endotoxin using the polypeptide of the present invention. According to the present invention, the term measurement is used as a collective name for detection, sensing, and quantitative determination. Therefore, the measurement method of the present invention may also be, for example, a method for detecting an endotoxin, a method for sensing an endotoxin, or a method for quantitatively determining an endotoxin.

The measurement method of the present invention is, for example, a method for measuring an endotoxin, the method including the following steps (1) and (2):

(1) a step of mixing the polypeptide of the present invention with horseshoe crab factor C and a test sample; and (2) a step of measuring protease activity of the polypeptide.

The step of the item (1) is a step of mixing the polypeptide of the present invention with horseshoe factor C and a test sample. In a case in which the test sample is a sample containing an endotoxin, a cascade reaction proceeds, in which factor C that has come into contact with the endotoxin is changed to activated factor C, and subsequently factor B is changed to activated factor B.

In the step of the item (1) may further include an operation of mixing another substance, as long as the step includes the operation of mixing the polypeptide of the present invention with factor C and a test sample. Examples of the "other substance" as used herein include a proclotting enzyme, a buffer agent, an alkali metal salt, an alkaline earth metal salt, a surfactant, and a substrate for detection. In a case in which the step of the item (1) is a step of mixing the polypeptide of the present invention with factor C, a proclotting enzyme, and a test sample, and the test sample is a sample containing an endotoxin, a cascade reaction proceeds, in which factor C that has come into contact with the endotoxin is changed to activated factor C, factor B is changed to activated factor B, and the proclotting enzyme is changed to a clotting enzyme.

The "factor C" used for the present invention is not particularly limited as long as it is factor C having the function of horseshoe crab factor C. The definition for the "horseshoe crab" used herein is as described in the section "<1> Polypeptide of present invention". The "function of horseshoe crab factor C" means the function as a protease precursor possessed by horseshoe crab factor C. The "function of horseshoe crab factor C" means specifically the function of being changed to an activated form (activated factor C) in the co-presence of an endotoxin and exhibiting the protease activity. The function of horseshoe crab factor C is, for example, the function of being changed to an activated form (activated factor C) in the co-presence of an endotoxin, cleaving factor B, and thereby changing the factor B into an activated form (activated factor B).

The "proclotting enzyme" according to the present invention is not particularly limited as long as it is a proclotting enzyme having the function of a horseshoe crab proclotting enzyme. The definition for the "horseshoe crab" use herein is as described in the section "<1> Polypeptide of present invention". The "function of a horseshoe crab proclotting enzyme" means the function as a protease precursor possessed by a horseshoe crab proclotting enzyme. The "function of a horseshoe crab proclotting enzyme" means specifically the function of being changed to an activated form (clotting enzyme) in the co-presence of activated factor B and exhibiting protease activity. The function of a horseshoe crab proclotting enzyme is, for example, the function of being changed to an activated form (clotting enzyme) in the co-presence of activated factor B, cleaving coagulogen, and thereby forming coagulin gel. Furthermore, the function of a horseshoe crab proclotting enzyme is, for example, the function of being changed to an activated form (clotting enzyme) in the co-presence of activated factor B, cleaving a substrate for detection, which serves as a substrate for a clotting enzyme, and thereby releasing a marker substance.

Factor C and the proclotting enzyme according to the present invention may be each independently a naturally occurring *Limulus* factor obtainable from horseshoe crab, may be a recombinant *Limulus* factor produced according to a genetic engineering technique, or may be a mixture including a naturally occurring *Limulus* factor and a recombinant *Limulus* factor at any arbitrary proportions.

The naturally occurring *Limulus* factor may be a *Limulus* factor obtained by using hemocyte of horseshoe crab as a raw material, purifying as appropriate a lysate obtained by a conventional method, and preparatively separating the *Limulus* factor. Preparative separation of a *Limulus* factor can be carried out by, for example, referring to a method described in the literature (Nakamura, T., Horiuchi, T., Morita T., and Iwanaga, S. (1986) J. Biochem. 99, 847-57).

A recombinant *Limulus* factor can be obtained by introducing a nucleic acid encoding a polypeptide of a *Limulus* factor into a cell and producing the *Limulus* factor in the cell. The base sequence of a nucleic acid encoding a *Limulus* factor can be obtained from a known database such as NCBI (worldwide web: ncbi.nlm.nih.gov).

The production of a *Limulus* factor using a cell can be carried out using a known technique. Regarding the production of a *Limulus* factor using a cell, a method of using a mammalian cell as described in <Example 1> or <Example 4> that will be described below may be mentioned as an example. Furthermore, the production of a *Limulus* factor using a cell can also be carried out by, for example, referring to a method described in the literature (WO 2012/118226 or WO 2014/092079). Furthermore, the production of a *Limulus* factor using a cell can also be carried out, for example, by applying the method described in the section "<5> Production method of present invention" mutatis mutandis.

Specific embodiments of the factor C and the proclotting enzyme according to the present invention can be presented by applying the description in the section "<1> Polypeptide of present invention" mutatis mutandis. For example, it is preferable that the *Limulus* factor according to the present invention is a recombinant. Furthermore, for example, the cell used for the production of the *Limulus* factor according to the present invention is preferably a mammalian cell or an insect cell, and more preferably a mammalian cell.

Regarding the factor C according to the present invention, specifically, a polypeptide represented by any one of the following (1) to (5) may be mentioned as an example.

(1) A polypeptide having an amino acid sequence represented by SEQ ID NO: 12;

(2) a polypeptide having an amino acid sequence represented by SEQ ID NO: 14;

(3) a polypeptide having an amino acid sequence represented by SEQ ID NO: 16;

(4) a polypeptide having an amino acid sequence including substitution, deletion, insertion, and/or addition of one amino acid residue or a plurality of amino acid residues in the amino acid sequence represented by any one of the items (1) to (3), the polypeptide having the function of horseshoe crab factor C; and (5) a polypeptide having the amino acid sequence of a fusion polypeptide in which a peptide tag is added to the polypeptide represented by any one of the items (1) to (4), the polypeptide having the function of horseshoe crab factor C.

Regarding the proclotting enzyme according to the present invention, specifically, a polypeptide represented by any one of the following (6) to (9) may be mentioned as an example.

(6) A polypeptide having an amino acid sequence set forth in SEQ ID NO: 18;

(7) a polypeptide having an amino acid sequence set forth in SEQ ID NO: 20;

(8) a polypeptide having an amino acid sequence including substitution, deletion, insertion, and/or addition of one amino acid residue or a plurality of amino acid residues in the amino acid sequence represented by the item (6) or (7), the polypeptide having the function of a horseshoe crab proclotting enzyme; and (9) a polypeptide having the amino acid sequence of a fusion polypeptide in which a peptide tag is added to the polypeptide represented by any one of the items (6) to (8), the polypeptide having the function of a horseshoe crab proclotting enzyme.

The amino acid sequence set forth in SEQ ID NO: 12 for the item (1) is the amino acid sequence of a polypeptide of *Tachypleus tridentatus* factor C.

The amino acid sequence set forth in SEQ ID NO: 14 for the item (2) is the amino acid sequence of a polypeptide of *Limulus polyphemus* factor C.

The amino acid sequence set forth in SEQ ID NO: 16 for the item (3) is the amino acid sequence of a polypeptide of *Carcinoscopius rotundicauda* factor C.

The amino acid sequence set forth in SEQ ID NO: 18 for the item (6) is the amino acid sequence of a polypeptide of *Tachypleus tridentatus* proclotting enzyme.

The amino acid sequence set forth in SEQ ID NO: 20 for the item (7) is the amino acid sequence of a polypeptide of *Limulus polyphemus* proclotting enzyme.

Embodiments of the term "a plurality" and "substitution, deletion, insertion, and/or addition" as used for the items (4) and (8) are the same as the embodiments for the section "<1> Polypeptide of present invention".

The polypeptide represented by the item (4) may be, for example, a polypeptide having a similarity of preferably 90% or higher, more preferably 95% or higher, even more preferably 98% or higher, and particularly preferably 99% or higher, with respect to the entire amino acid sequence represented by any one of the items (1) to (3), the polypeptide having the function of horseshoe crab factor C. Furthermore, the polypeptide represented by the item (8) may be, for example, a polypeptide having a similarity of preferably 90% or higher, more preferably 95% or higher, even more preferably 98% or higher, and particularly preferably 99% or higher, with respect to the entire amino acid sequence represented by the item (6) or (7), the polypeptide having the function of a horseshoe crab proclotting enzyme. In addition, the "similarity" as used for these is a concept including the term "identity", and therefore, the term similarity can be replaced with the term identity and applied to suitable embodiments of the polypeptide.

The embodiments of the "peptide tag" for the item (4) and (8) are the same as the embodiments for the section "<1> Polypeptide of present invention".

The "substrate for detection" according to the present invention is a substrate used for measuring the presence or absence of an activated *Limulus* factor, the amount of the activated *Limulus* factor, or the progress of the cascade reaction. The substrate for detection may be a substrate for measuring activated factor B, or may be a substrate for measuring a clotting enzyme. The substrate for detection is not particularly limited as long as it is a substrate that serves as a substrate for an activated *Limulus* factor. The substrate for detection may be, for example, a protein, a peptide, or a derivative of any one of these.

The protein may be a naturally occurring protein, or may be a recombinant protein. An example of the protein is coagulogen, which is a substrate for a clotting enzyme. For example, naturally occurring coagulogen can be produced by preparatively separating the substance from a lysate. Furthermore, for example, a recombinant coagulogen can be produced by referring to a method described in the literature (Miyata, et al., Tanpakushitsu Kakusan Koso Bessatsu (Proteins, Nucleic acids, and Enzymes: Extra Issue) No. 29; p. 30-43; 1986).

The peptide may be, for example, a synthetic substrate that is chemically synthesized. The synthetic substrate is not particularly limited as long as it is a substrate suitable for measuring the presence or absence of an activated *Limulus* factor, the amount of the activated *Limulus* factor, or the progress of the cascade reaction. The synthetic substrate is preferably a derivative of a peptide.

An example of the synthetic substrate is a substrate represented by general formula: Y—X—Z (wherein Y may or may not exist; in a case in which Y exists, Y represents a protective group; X represents a peptide; and Z represents a marker substance). It is desirable that such a synthetic substrate has a property by which the covalent bond between X and Z is cleaved by an activated *Limulus* factor, and a marker substance Z is released. In regard to the general formula described above, it is preferable that the protective group (Y) is a protective group for an amino group at the N-terminal of a peptide. In regard to the general formula, it is preferable that the bond between Y and X is an amide bond formed between a carboxy group of the protective group and an α-amino group at the N-terminal of a peptide. Furthermore, in regard to the general formula, it is preferable that the bond between X and Z is an amide bond formed between a carboxy group at the C-terminal of a peptide and an amino group of the marker substance Z.

The protective group (Y) is not particularly limited, and any known protective group that is applicable to the protection of a peptide can be used. Examples of the protective group (Y) include a tert-butoxycarbonyl group (Boc), a benzyloxycarbonyl group (Cbz), a benzyl group (Bzl), a benzoyl group (Bz), and an acetyl group (Ac).

The peptide (X) is not particularly limited as long as it is a peptide having an amino acid sequence that serves as a substrate for an activated *Limulus* factor. It is preferable that the peptide is a substrate suitable for the measurement of a serine protease, and it is preferable that the peptide is a peptide having an Arg (R) residue at the C-terminal.

In a case in which the *Limulus* factor is factor B, it is preferable that the peptide is a peptide having an amino acid sequence represented by general formula: X-Thr-Arg (wherein X represents any arbitrary amino acid). Specifically, in a case in which the *Limulus* factor is factor B, it is preferable that the peptide is a peptide having an amino acid sequence represented by Leu-Thr-Arg (LTR) or Met-Thr-Arg (MTR).

In a case in which the *Limulus* factor is a proclotting enzyme, it is preferable that the peptide is a peptide having an amino acid sequence represented by general formula: X-Gly-Arg (wherein X represents any arbitrary amino acid). Specifically, in a case in which the *Limulus* factor is a proclotting enzyme, it is preferable that the peptide is a peptide having an amino acids sequence represented by Leu-Gly-Arg (LGR) or Glu-Gly-Arg (EGR).

The marker substance (Z) is not particularly limited, and any known marker substance that can be applied to the measurement of protease activity can be used. Regarding the marker substance, for example, a marker substance that becomes, when released from a peptide, detectable through color development or fluorescence, can be used. Examples of such a marker substance include para-nitroaniline (pNA), 7-methoxycoumarin-4-acetic acid (MCA), and 2,4-dinitroaniline (DNP). Furthermore, regarding the marker substance, for example, a marker substance that becomes, when released from a peptide, detectable according to an electrochemical measurement method (voltammetry, amperometry, or the like), can be used. Examples of such a marker substance include p-aminophenol (pAP), p-methoxyaniline (pMA), N-methyl-p-phenylenediamine (MPDD), and N,N'-dimethyl-p-phenylenediamine (DMPD).

In the step of (1) in the measurement method of the present invention as described above, the polypeptide of the present invention, a *Limulus* factor, a test sample, a substrate for detection, and other substances (a buffer agent and the like) may be added in an arbitrary order and mixed. For example, in the step of (1), the test sample may be added to a mixture of the polypeptide of the present invention, a *Limulus* factor, a substrate for detection, and other substances, and mixed with the mixture. Furthermore, for example, in the step of (1), the test sample may have a mixture of the polypeptide of the present invention, a *Limulus* factor, a substrate for detection, and other substances added thereto and mixed. In the step of (1), mixing may be carried out, for example, in the inside (in a container) of a container having an opening at one end (a test tube, a vial, or the like). The test sample is not particularly limited, and examples include water for injection, a pharmaceutical product, an infusion liquid, a blood preparation, a medical instrument (medical tool), a quasi-drug, a cosmetic, as well as a food product, a beverage, an environmental sample collected from air, river, soil, or the like; a naturally occurring protein, a recombinant protein, a nucleic acid, an enzyme, a carbohydrate, an electrolyte; and a biological component such as blood, a body fluid, or a tissue.

The step of (2) is a step of measuring the protease activity of the polypeptide of the present invention. This step is, for example, a step of measuring a marker substance released from a substrate for detection. In this step, since a marker substance in an amount (mole number) corresponding to the protease activity (total activity) of the polypeptide of the present invention is released from a substrate for detection, the protease activity of the polypeptide of the present invention can be measured by measuring a marker substance released from the substrate for detection. A marker substance released from the substrate for detection can be measured using, for example, an optical instrument such as a spectrophotometer or a fluorophotometer. Furthermore, a marker substance released from a substrate for detection can be measured using, for example, an electrochemical measuring instrument such as a voltammeter or an amperometer. For example, the presence or absence of an endotoxin in a test sample can be determined by comparing the measured value shown in that step with a blank value (measured value obtained in a case in which an endotoxin-free test sample as an object of measurement).

The measurement method of the present invention may further include another step in addition to the steps of (1) and (2). The measurement method of the present invention may include, for example, a step of determining the presence or absence of an endotoxin in a test sample by comparing the measurement obtainable in the step of (2) with a blank value. Furthermore, the measurement method of the present invention may also include, for example, a step of determining the presence or absence of an endotoxin in a test sample by determining the presence or absence of gelation of a mixed liquid. Furthermore, the measurement method of the present invention may include, for example, a step of converting the measured value obtainable in the step of (2) into another value. Regarding the step of converting a measured value into another value, for example, a step of calculating the amount of an endotoxin based on the measured value may be mentioned as an example. Such a step is specifically, for example, a step of converting the measured value obtainable when a test sample is measured, into the amount of an endotoxin based on the relation (standard curve) between the measured value obtainable when a test sample is substituted with a standard substance at a known concentration, and the concentration of the standard substance.

In regard to the measurement method of the present invention, it is preferable that the *Limulus* reaction is carried out in water or an aqueous solvent such as a buffer solution.

<7> Reagent of Present Invention

The reagent of the present invention is a reagent for endotoxin measurement, including the polypeptide of the present invention as a constituent component. The reagent of the present invention can be suitably used in order to carry out the measurement method of the present invention.

The reagent of the present invention may further include another constituent component as long as the reagent includes the polypeptide of the present invention as a constituent component. Regarding the other constituent component as used herein, for example, horseshoe crab factor C, a horseshoe crab proclotting enzyme, a substrate for detection, a buffer agent, an alkali metal salt, an alkaline earth metal salt, and a surfactant.

It is preferable that the reagent of the present invention includes horseshoe crab factor C as a constituent component in addition to the polypeptide of the present invention, and it is more preferable that the reagent of the present invention further includes a horseshoe crab proclotting enzyme as a constituent component. Furthermore, it is preferable that the reagent of the present invention is supplied as a freeze-dried product.

<8> Kit of Present Invention

The kit of the present invention is a kit for endotoxin measurement, including the polypeptide of the present invention or the reagent of the present invention as a component part. The kit of the present invention can be suitably used in order to carry out the measurement method of the present invention.

As long as the kit of the present invention includes the polypeptide of the present invention or the reagent of the present invention as a component part, the kit of the present invention may further include another component part. Examples of the other component part as used herein include horseshoe crab factor C, a horseshoe crab proclotting enzyme, a substrate for detection, a buffer solution, distilled water, an endotoxin standard product, a microplate, and an attached document with product information described therein.

The kit of the present invention may include various component parts individually separately, or may include various component parts as a mixture formed by arbitrarily combining the component parts. The kit of the present invention may include, for example, various *Limulus* factors separately, or as an embodiment of having the various *Limulus* factors mixed in advance, or as an embodiment of further having a substrate for detection mixed with the various *Limulus* factors in advance.

EXAMPLES

Hereinafter, an embodiment of the present invention will be described specifically by way of Examples; however, the technical scope of the present invention is not intended to be limited to these Examples only.

In the Examples of the present invention, the following abbreviations may be used.

(a) TFC: *Tachypleus tridentatus* factor C
(b) TFB: *Tachypleus tridentatus* factor B
(c) Murasame-TFB: *Tachypleus tridentatus* factor B variant
(d) LFC: *Limulus polyphemus* factor C
(e) LFB: *Limulus polyphemus* factor B
(f) Murasame-LFB: *Limulus polyphemus* factor B variant In the Examples of the present invention, production of an expression vector, production of a *Limulus* factor, and measurement of the activity of a *Limulus* factor can be carried out by referring to the methods described in the literature (Kobayashi, Y., Takahashi, T., Shibata, T., Ikeda, S., Koshiba, T., Mizumura, H., Oda, T., Kawabata, S. (2015) J. Biol. Chem. 290, 19379-86).

In the Examples of the present invention, unless particularly stated otherwise, a PCR reaction was carried out by using Phusion High-Fidelity DNA Polymerase (manufactured by New England Biolabs) and performing the operation according to the attached protocol.

Purification of a DNA from a PCR reaction liquid in the Examples of the present invention, was carried out by using Wizard SV Gel and PCR Clean-Up System (manufactured by Promega Corporation) and performing the operation according to the attached protocol.

Preparative separation of a DNA in the Examples of the present invention was carried out by subjecting a sample including a DNA to agarose gel electrophoresis, cutting out a desired DNA fragment with a scalpel, collecting the DNA fragment, and then performing the operation using Wizard SV Gel and PCR Clean-Up System (manufactured by Promega Corporation) according to the attached protocol.

In the Examples of the present invention, unless particularly stated otherwise, the ligation reaction was carried out using T4DNA ligase (manufactured by New England Biolabs) and performing the operation according to the attached protocol.

Amplification and purification of a vector in the Examples of the present invention were carried out by culturing *Escherichia coli* that had been transformed using a vector, and then performing the operations using Wizard Plus SV Minipreps DNA Purification System (manufactured by Promega Corporation) according to the attached protocol. Specifically, *Escherichia coli* DH5a strain that had been transformed using a vector was applied on a plate of ampicillin-containing LB (LB/Amp) agar medium, the bacterial cells were subjected to static culture overnight, single colonies thus obtained were inoculated into ampicillin-containing LB medium, the bacterial cells were subjected to shaking culture overnight at 37° C. to perform amplification of the vector, and the vector was purified from the bacterial cells of *Escherichia coli* in the culture fluid.

Dephosphorylation of a DNA in the Examples of the present invention was carried out using Alkaline Phosphatase (*E. coli* C75) (manufactured by Takara Bio, Inc.) by performing the operation according to the attached protocol.

Measurement of the protein concentration in the Examples of the present invention was carried out using Micro BCA Protein Assay Kit (manufactured by Thermo Fisher Scientific) by performing the operation according to the attached protocol. Furthermore, the molar concentration of a *Limulus* factor in the Examples of the present invention was calculated by dividing the protein concentration obtainable by the above-mentioned measurement by the molecular weight of the *Limulus* factor.

<Reference Example 1> Production of TFC (1) Production of TFC Expression Vector

An expression vector for *Tachypleus tridentatus* factor C (TFC) was produced according to the following procedure.

A DNA encoding full-length TFC excluding the signal sequence of the N-terminal (DNA having a base sequence represented by base numbers 76 to 3057 of SEQ ID NO: 11) was produced by a PCR reaction. As a template for the PCR reaction, a vector produced by inserting the TFC-encoding DNA into pSecTag2A vector (manufactured by Invitrogen) (Koshiba, T., Hashii, T., Kawabata, S. (2007) J. Biol. Chem. 282, 3962-7) was used. As primers for the PCR reaction, Primer 1 (SEQ ID NO: 21) and BGH reverse primer (SEQ ID NO: 28) were used.

The DNA obtained by the PCR reaction was purified, and the DNA was subjected to limited digestion using restriction enzymes (Age I and Kpn I) and preparative separation. pHLsec vector (Aricescu, A R., Lu, W., Jones, E Y. (2006) Acta Crystallogr. D Biol. Crystallogr. 62, 1243-50) was subjected to limited digestion using restriction enzymes and preparative separation in the same manner as described above, and then a ligation reaction between the vector and the above-mentioned DNA was carried out.

*Escherichia coli* was transformed by using the ligation reaction liquid, and then amplification and purification of the vector were carried out. The vector was subjected to limited digestion using a restriction enzyme (EcoR I) and preparative separation, and DNA fragment 1 (DNA having a base sequence encoding the amino acid sequence of a pHLsec vector-derived secretion signal, and a base sequence represented by base numbers 76-2298 of SEQ ID NO: 11, the DNA having the sticky ends of EcoR I at the 5'-terminal and the 3'-terminal) was obtained. Furthermore, the vector was subjected to limited digestion using restriction enzymes (EcoR I and Xho I) and preparative separation, and DNA fragment 2 (DNA having a base sequence represented by base numbers 2299 to 2545 of SEQ ID NO: 11, the DNA having the sticky end of EcoR I at the 5'-terminal and the sticky end of Xho I at the 3'-terminal) and DNA fragment 3 (DNA having a base sequence represented by base numbers 2546 to 3057 of SEQ ID NO: 11 and a base sequence encoding the amino acid sequence of a pHLsec vector-derived His tag, the DNA having the sticky ends of Xho I at the 5'-terminal and the 3'-terminal) were obtained.

pCA7 vector (Takeda, M., Ohno, S., Seki, F., Nakatsu, Y., Tahara, M., Yanagi, Y. (2005) J. Virol. 79, 14346-54) was subjected to limited digestion using restriction enzymes (EcoR I and Xho I) and preparative separation, and then a ligation reaction between the vector and the DNA fragment 2 was carried out.

*Escherichia coli* was transformed using the above-mentioned ligation reaction liquid, and then amplification and purification of the vector were carried out. The vector was subjected to limited digestion using a restriction enzyme (Xho I), dephosphorylation, and preparative separation, and then a ligation reaction between the vector and the DNA fragment 3 was carried out.

*Escherichia coli* was transformed using the above-mentioned ligation reaction liquid, and then amplification and purification of the vector were carried out. The vector was subjected to limited digestion using a restriction enzyme (EcoR I), dephosphorylation, and preparative separation, and then a ligation reaction between the vector and the DNA fragment 1 was carried out.

*Escherichia coli* was transformed using the above-mentioned ligation reaction liquid, and then amplification and purification of the vector were carried out. In this manner, a vector encoding a TFC having a His tag at the C-terminal was obtained.

A PCR reaction was carried out using the above-mentioned vector as a template and using Primer 8 (SEQ ID NO: 29) and Primer 2 (SEQ ID NO: 22), and the DNA thus amplified was purified. The DNA was subjected to limited digestion using a restriction enzyme (EcoR I) and preparative separation, and DNA fragment 1 was obtained. Furthermore, The DNA was subjected to limited digestion using restriction enzymes (EcoR I and Xho I) and preparative separation, and DNA fragment 2 and DNA fragment 4 (DNA having a base sequence represented by base numbers 2546 to 3057 of SEQ ID NO: 11, the DNA having the sticky ends of Xho I at the 5'-terminal and the 3'-terminal) were obtained.

pCA7 vector was subjected to limited digestion using restriction enzymes (EcoR I and Xho I) and preparative separation, and then a ligation reaction between the pCA7 vector and the DNA fragment 2 was carried out.

*Escherichia coli* was transformed using the above-mentioned ligation reaction liquid, and then amplification and purification of the vector were carried out. The vector was subjected to limited digestion using a restriction enzyme (Xho I), dephosphorylation, and preparative separation, and then a ligation reaction between the vector and the DNA fragment 4 was carried out.

*Escherichia coli* was transformed using the above-mentioned ligation reaction liquid, and then amplification and purification of the vector were carried out. The vector was subjected to limited digestion using a restriction enzyme (EcoR I), dephosphorylation, and preparative separation, and then a ligation reaction between the vector and the DNA fragment 1 was carried out.

*Escherichia coli* was transformed using the above-mentioned ligation reaction liquid, and then amplification and purification of the vector were carried out. In this manner, a vector encoding a TFC that did not have a His tag at the C-terminal was obtained.

The vector was subjected to limited digestion using a restriction enzyme (EcoR I), dephosphorylation, and preparative separation, and DNA fragment 5 (DNA having a base sequence represented by base numbers 2299 to 3057 of SEQ ID NO: 11 and the base sequence of pCA7 vector, the DNA having the sticky ends of EcoR I at the 5'-terminal and the 3'-terminal) was obtained.

A PCR reaction was carried out using a vector produced by inserting a DNA encoding full-length TFC including the signal sequence of the N-terminal (DNA having a base sequence represented by base numbers 1 to 3057 of SEQ ID NO: 11) into pPSC8 vector (manufactured by Protein Sciences Corporation), as a template, and using Primer 3 (SEQ ID NO: 23) and Primer 2 (SEQ ID NO: 22), and thus the DNA thus amplified was purified. The DNA was subjected to limited digestion using a restriction enzyme (EcoR I) and preparative separation, and DNA fragment 6 (DNA having a base sequence represented by base numbers 1 to 2298 of SEQ ID NO: 11, the DNA having the sticky ends of EcoR I at the 5'-terminal and the 3'-terminal) was obtained. Subsequently, a ligation reaction between the DNA fragment 6 and the DNA fragment 5 was carried out.

Escherichia coli was transformed using the above-mentioned ligation reaction liquid, and then amplification and purification of the vector were carried out. In this manner, a vector encoding full-length TFC including the signal sequence of the N-terminal was obtained.

An inverse PCR reaction was carried out using the above-mentioned vector as a template and phosphorylated primers (Primer 4 (SEQ ID NO: 24) and Primer 5 (SEQ ID NO: 25)). The inverse PCR reaction was carried out by using Q5 High-Fidelity DNA Polymerase (manufactured by New England Biolabs) and performing the operation according to the attached protocol. A restriction enzyme (Dpn I) was added to the PCR reaction liquid to degrade the template, and preparative separation of the DNA was carried out by performing phenol/chloroform extraction and ethanol precipitation. Subsequently, a ligation reaction (self-ligation) was carried out by using DNA Ligation Kit <Mighty Mix> (manufactured by Takara Bio, Inc.) and performing the operation according to the attached protocol.

Escherichia coli was transformed using the above-mentioned ligation reaction liquid, and the amplification and purification of the vector were carried out. In this manner, a vector encoding a TFC having the 6×His tags and the amino acid sequence of factor Xa cleavage sequence (IEGR) inserted therein immediately after a signal sequence, was obtained.

A PCR reaction was carried out using the above-mentioned vector as a template and using Primer 6 (SEQ ID NO: 26) and Primer 7 (SEQ ID NO: 27), and the DNA thus amplified was purified. The PCR reaction was carried out by using Q5 High-Fidelity DNA Polymerase and performing the operation according to the attached protocol. The DNA was subjected to limited digestion using restriction enzymes (Age I and Nhe I) and preparative separation, and DNA fragment 7 (DNA having a base sequence encoding the 6×His tag, a base sequence encoding IEGR, and a base sequence represented by base numbers 76 to 2236 of SEQ ID NO: 11, the DNA having the sticky end of Age I at the 5'-terminal and the sticky end of Nhe I at the 3'-terminal) was obtained.

The vector encoding a TFC that did not have a His tag at the C-terminal was subjected to limited digestion using restriction enzymes (Age I and Nhe I), dephosphorylation, and preparative separation, and DNA fragment 8 (DNA having a base sequence represented by base numbers 2237 to 3057 of SEQ ID NO: 11 and the base sequence of pCA7 vector, the DNA having the sticky end of Nhe I at the 5'-terminal and the sticky end of Age I at the 3'-terminal) was obtained. Subsequently, a ligation reaction between the DNA fragment 8 and the DNA fragment 7 was carried out.

Escherichia coli was transformed using the above-mentioned ligation reaction liquid, and then amplification and purification of the vector were carried out. The base sequence of the vector was subjected to a sequence analysis, and it was confirmed that there was no introduction of mutation caused by PCR error. In this manner, an expression vector for a polypeptide having the 6×His tag and the factor Xa cleavage sequence (IEGR) on the N-terminal side of a TFC sequence excluding the signal sequence of the N-terminal (hereinafter, referred to as "TFC/pCA7") was obtained.

(2) Production of TFC

Tachypleus tridentatus factor C (TFC) was produced by a mammalian cell expression system according to the following procedure. Cell culture was carried out under the conditions of 37° C. and 5% $CO_2$.

HEK293S GnTI⁻ cells (ATCC: CRL-3022) were transformed using the expression vector for TFC (TFC/pCA7) obtained in the section (1). Specifically, to the cells that had reached a confluence of 80% to 90%, a transformation medium (DMEM medium including TFC/pCA7 (1.8 µg/mL), polyethyleneimine (2.7 µg/mL), a 1% penicillin-streptomycin-L-glutamine solution (manufactured by Wako Pure Chemical Industries, Ltd.), and 2% bovine fetal serum) was added to a concentration of 0.22 mL/cm², and benzamidine was added to the cell to a final concentration of 2 mM. The mixture was subjected to static culture for 120 hours. In this manner, a culture fluid including TFC that had been secreted from the cells was obtained.

The culture fluid was centrifuged at 6,000×g for 30 minutes, and the supernatant was collected. The supernatant and a buffer solution (0.5 M $NaH_2PO_4$—NaOH (pH 8.0), 1.5 M NaCl, and 0.1 M imidazole) in a 0.1-fold amount were mixed, and then the mixture was applied to a nickel column (nickel-nitrilotriacetic acid agarose column, inner diameter: 1.0 cm×length: 5.0 cm). The column was washed with a washing solution (50 mM $NaH_2PO_4$—NaOH (pH 8.0), 150 mM NaCl, and 10 mM imidazole), and then TFC was eluted using an elution solution (50 mM $NaH_2PO_4$—NaOH (pH 8.0), 150 mM NaCl, and 20 to 200 mM imidazole). The eluted fraction of TFC was checked by gel electrophoresis (SDS-PAGE).

The eluted fraction of TFC was collected, and the solution was replaced with a reaction solution (20 mM Tris-HCl (pH 8.0), 150 mM NaCl, and 10 mM $CaCl_2$) by ultrafiltration. Subsequently, factor Xa was added to the solution to a concentration of 3.3 µg/mL, and the mixture was left to stand for 16 hours at 37° C. Thus, the His tag was released from the N-terminal of TFC.

The above-mentioned reaction solution was applied to a sepharose column (benzamidine-Sepharose column, inner diameter: 0.25 cm×length: 1.5 cm), and factor Xa was eliminated by adsorbing factor Xa to the column. Subsequently, a flow-through fraction (flow-through) of the column was applied to a nickel column (nickel-nitrilotriacetic acid-agarose column, inner diameter: 0.25 cm×length: 1.5 cm), and the His tag released from TFC was eliminated by adsorbing the His tag to the column. The flow-through fraction of the column was used as TFC in the subsequent test.

<Reference Example 2> Production of TFB (1) Production of TFB Expression Vector

An expression vector for *Tachypleus tridentatus* factor B (TFB) was produced by the following procedure.

A DNA encoding full-length TFB excluding the signal sequence of the N-terminal (DNA having a base sequence represented by base numbers 70 to 1200 of SEQ ID NO: 1) was produced by a PCR reaction. As a template for the PCR reaction, a vector produced by inserting a DNA encoding TFB into pPSC8 vector was used. Furthermore, as primers for the PCR reaction, Primer 9 (SEQ ID NO: 30) and Primer 10 (SEQ ID NO: 31) were used.

The DNA obtained by the PCR reaction was purified, and the DNA was subjected to limited digestion using restriction enzymes (Age I and Xho I) and preparative separation were carried out. pCA7 vector was subjected to limited digestion using restriction enzymes (Age I and Xho I) and preparative separation, and then a ligation reaction between the pCA7 vector and the above-mentioned DNA was carried out. *Escherichia coli* was transformed using the above-mentioned ligation reaction liquid, and then amplification and purification of the vector were carried out. The base sequence of the vector was subjected to a sequence analysis, and it was confirmed that there was no introduction of mutation caused by PCR error. In this manner, an expression vector for TFB excluding the signal sequence of the N-terminal (TFB/pCA7) was obtained.

(2) Production of TFB

*Tachypleus tridentatus* factor B (TFB) was produced by a mammalian cell expression system by the following procedure. Cell culture was carried out under the conditions of 37° C. and 5% $CO_2$.

The same operation as that employed in "(2) Production of TFC" in <Reference Example 1> was carried out, except that the expression vector for TFB obtained in the section (1) (TFB/pCA7) was used instead of the expression vector for TFC (TFC/pCA7), and benzamidine was not added. Thus, a culture fluid including TFB that had been secreted from the cells was obtained.

The culture fluid was centrifuged at 6,000×g for 30 minutes, and the supernatant was collected. 50 mM $NaH_2PO_4$—NaOH (pH 6.8) was added to the supernatant to dilute the supernatant by five times, and then the dilution was applied to an SP column (SP-Sepharose column, inner diameter: 1.0 cm×length: 10 cm). The column was washed with 50 mM $NaH_2PO_4$—NaOH (pH 6.8), and then TFB was eluted using an elution solution (50 mM $NaH_2PO_4$—NaOH (pH 6.8), and 50 to 500 mM NaCl). The elution fraction of TFB was checked by gel electrophoresis (SDS-PAGE).

The eluted fraction of TFB was collected, and the solution was replaced with 20 mM Tris-HCl (pH 8.0) by ultrafiltration. The solution was applied to a DEAE column (DEAE-Sepharose column, inner diameter: 1.0 cm×length: 1.0 cm), and then TFB was eluted using an elution solution (20 mM Tris-HCl (pH 8.0), and 10 to 200 mM NaCl). The eluted fraction of TFB was checked by gel electrophoresis (SDS-PAGE). The eluted fraction of TFB was used as TFB in the subsequent test.

<Example 1> Production of Murasame-TFB

An expression vector for *Tachypleus tridentatus* factor B variant (Murasame-TFB) was produced by the following procedure.

(1) Production of Murasame-TFB Expression Vector

An inverse PCR reaction was carried out using the TFB/pCA7 as a template and using phosphorylated primers (Primer 11 (SEQ ID NO: 32) and Primer 12 (SEQ ID NO: 33)). The inverse PCR reaction was carried out by using Tks Gflex DNA polymerase (manufactured by Takara Bio, Inc.) and performing the operation according to the attached protocol. A restriction enzyme (Dpn I) was added to the PCR reaction liquid, and the template was degraded. Preparative separation of the DNA was carried out by performing phenol/chloroform extraction and ethanol precipitation, and then a ligation reaction (self-ligation) was carried out using DNA Ligation Kit <Mighty Mix> and performing the operation according to the attached protocol.

*Escherichia coli* was transformed using the above-mentioned ligation reaction liquid, and then amplification and purification of the vector were carried out. The base sequence of the vector was subjected to a sequence analysis, and it was confirmed that there was no introduction of mutation caused by PCR error. In this manner, an expression vector for Murasame-TFB (Murasame-TFB/pCA7) was obtained.

(2) Production of Murasame-TFB

The *Tachypleus tridentatus* factor B variant (Murasame-TFB) was produced by a mammalian cell expression system according to the following procedure. Cell culture was carried out under the conditions of 37° C. and 5% $CO_2$.

The same operation as that employed in "(2) Production of TFC" in the section <Reference Example 1> was carried out, except that the expression vector for Murasame-TFB (Murasame-TFB/pCA7) obtained in the section (1) was used instead of the expression vector for TFC (TFC/pCA7), and benzamidine was not added. Thus, a culture fluid including Murasame-TFB that had been secreted from the cells was obtained.

The same operation as that employed in "(2) Production of TFB" in <Reference Example 2> was carried out, and an eluted fraction including Murasame-TFB was obtained. The eluted fraction of Murasame-TFB was used as Murasame-TFB in the subsequent test.

<Reference Example 3> Measurement of Protease Activity (Specific Activity) of TFB A solution of 160 nM TFC, 3.2 µM LPS (derived from *Salmonella minnesota* R595, weight average molecular weight 1,700 Da, manufactured by List Biological Laboratories, Inc.), 20 mM Tris-HCl (pH 8.0), and 150 mM NaCl was produced, and the solution was left to stand at 37° C. for 20 minutes. Thus, TFC was activated. Hereinafter, activated TFC will be referred to as "α-TFC".

20 µL of a solution including 50 nM TFB, 0.2 nM α-TFC, 20 mM Tris-HCl (pH 8.0), 150 mM NaCl, and 100 µg/mL BSA was produced, and the solution was left to stand for one hour at 37° C. To this solution, 5 µL of 2 mM Boc-Leu-Thr-Arg-MCA (manufactured by Peptide Institute, Inc.) dissolved in 20% DMF was added, and the mixture was left to stand for 5 minutes at 37° C. 0.6 M Acetic acid (75 µL) was added to the mixture to complete the enzyme reaction, and then the amount of MCA released from the peptide (properly proportional to the protease activity (total activity) of activated TFB) was measured with a fluorescence detector. The detection was carried out under the conditions of an excitation wavelength of 380 nm and a fluorescence wavelength of 440 nm.

As a result, the protease activity (specific activity) of TFB was 31.07±2.50 units/μmol.

<Example 2> Measurement of Protease Activity (Specific Activity) of Murasame-TFB The same operation as that employed in <Reference Example 3> was carried out using Murasame-TFB instead of TFB, and the protease activity of Murasame-TFB was measured.

As a result of the test, the protease activity (specific activity) of Murasame-TFB was 416.87±20.50 units/μmol.

The results of <Reference Example 3> and <Example 2> are presented in FIG. 1. From the results of the above-described test, it was found that Murasame-TFB has a protease activity (specific activity) that is 13.4 times the protease activity of TFB.

<Reference Example 4> Evaluation of Thermal Stability of TFB

10 μL of a solution of 100 nM TFB, 20 mM Tris-HCl (pH 8.0), 150 mM NaCl, and 100 μg/mL BSA was produced, and the solution was left to stand for 2 minutes at a predetermined temperature (40° C., 50° C., 60° C., 70° C., 80° C., or 90° C.). Subsequently, to this solution, 10 μL of a solution of 0.4 nM α-TFC, 20 mM Tris-HCl (pH 8.0), 150 mM NaCl, and 100 μg/mL BSA was added, and the mixture was left to stand for one hour at 37° C. Subsequently, the protease activity of TFB was measured by performing the same operation as that employed in <Reference Example 3>. The results of the above-described test are presented in Table 1.

TABLE 1

| Temperature | Relative activity |
|---|---|
| 40° C. | 103.60% |
| 50° C. | 40.00% |
| 60° C. | 0.0% |
| 70° C. | 0.0% |
| 80° C. | 0.0% |
| 90° C. | 0.0% |

In Table 1, the "relative activity" is a numerical value (%) expressing, in percentage, a value obtained by dividing the protease activity (specific activity) of TFB that had been left to stand for 2 minutes at each of the various temperatures, by the protease activity (specific activity) of TFB shown in <Reference Example 3>.

<Example 3> Evaluation of Thermal Stability of Murasame-TFB

The thermal stability of Murasame-TFB was evaluated by performing the same operation as that employed in <Reference Example 4> using Murasame-TFB instead of TFB. The results of the test are presented in Table 2.

TABLE 2

| Temperature | Relative activity |
|---|---|
| 40° C. | 99.64% |
| 50° C. | 85.17% |
| 60° C. | 72.63% |
| 70° C. | 57.64% |
| 80° C. | 50.12% |
| 90° C. | 42.92% |

In Table 2, the relative activity is a numerical value (%) expressing, in percentage, a value obtained by dividing the protease activity (specific activity) of Murasame-TFB that had been left to stand for 2 minutes at each of the various temperatures, by the protease activity (specific activity) of Murasame-TFB shown in <Example 2>.

Figure 2:
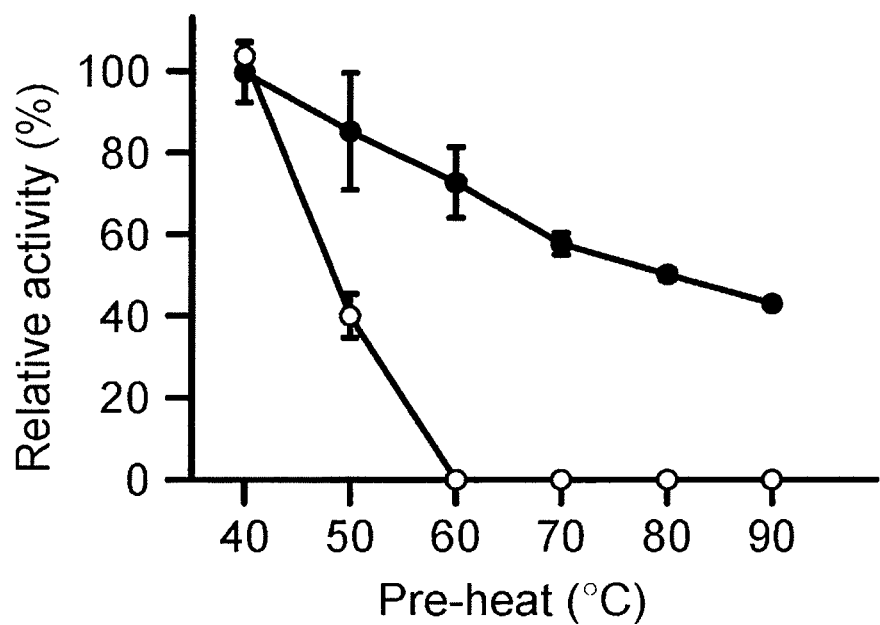
FIG. 2 is a diagram showing the thermal stability of *Tachypleus tridentatus* factor B (TFB) (graph represented by ○) and *Tachypleus tridentatus* factor B variant (Murasame-TFB) (graph represented by ●).

The results of <Reference Example 4> and <Example 3> are presented in FIG. 2. From the results of the above-described test, it was found that TFB completely loses its protease activity (deactivated) when heated for 2 minutes at or above 60° C. Meanwhile, it was found that Murasame-TFB maintains 40% or more of its protease activity even when heated for 2 minutes at 90° C., and thus Murasame-TFB has higher thermal stability than TFB.

<Reference Example 5> Production of LFC (1) Production of LFC Expression Vector

An expression vector for *Limulus polyphemus* factor C (LFC) was produced according to the following procedure.

A DNA encoding full-length LFC excluding the signal sequence of the N-terminal (DNA having a base sequence represented by base numbers 76 to 3060 of SEQ ID NO: 13) was produced by a PCR reaction using Tks Gflex DNA polymerase (manufactured by Takara Bio, Inc.). As a template for the PCR reaction, a vector obtained by inserting a DNA encoding LFC into pBluescript II SK(+) (manufactured by Agilent Technologies, Inc.) was used. As primers for the PCR reaction, Primer 13 (SEQ ID NO: 34) and Primer 14 (SEQ ID NO: 35) were used.

The DNA obtained by the above-described PCR was collected by performing phenol/chloroform extraction, and the DNA was subjected to limited digestion using restriction enzymes (Age I and Xho I) and preparative separation. TFC/pCA7 was subjected to limited digestion using restriction enzymes and preparative separation in the same manner as described above, and then a ligation reaction between the DNA and TFC/pCA7 was carried out.

*Escherichia coli* was transformed using the above-mentioned ligation reaction liquid, and then amplification and purification of the vector were carried out. The base sequence of the vector was subjected to a sequence analysis, and it was checked that there was no introduction of mutation caused by PCR error. In this manner, an expression vector for a polypeptide having the 6×His tag and factor Xa cleavage sequence (IEGR) on the N-terminal side of the LFC sequence excluding the signal sequence of the N-terminal (hereinafter, referred to as "LFC/pCA7") was obtained.

(2) Production of LFC

*Limulus polyphemus* factor C (LFC) was produced by a mammalian cell expression system according to the following procedure. Cell culture was carried out under the conditions of 37° C. and 5% $CO_2$.

HEK293S GnTI⁻ cells (ATCC: CRL-3022) were transformed using the expression vector for LFC (LFC/pCA7) obtained in the section (1). Specifically, to the above-mentioned cells that had reached a confluence of 80% to 90%, a transformation medium (DMEM medium including LFC/pCA7 (1.8 μg/mL), polyethyleneimine (2.7 μg/mL), a 1% penicillin-streptomycin-L-glutamine solution (manufactured by Wako Pure Chemical Industries, Ltd.), and 2% bovine fetal serum) was added to a concentration of 0.22 mL/cm², and benzamidine was added to the cell to a final concentration of 2 mM. The mixture was subjected to static culture for 120 hours. In this manner, a culture fluid including LFC that had been secreted from the cells was obtained.

The culture fluid was centrifuged at 6,000×g for 30 minutes, and the supernatant was collected. The supernatant and a buffer solution (0.5 M $NaH_2PO_4$—NaOH (pH 8.0), 1.5 M NaCl, and 0.1 M imidazole) in a 0.1-fold amount were mixed, and then the mixture was applied to a nickel column (nickel-nitrilotriacetic acid agarose column, inner diameter: 1.0 cm×length: 2.0 cm). The column was washed with a washing solution (50 mM $NaH_2PO_4$—NaOH (pH 8.0), 150 mM NaCl, and 10 mM imidazole), and then LFC was eluted using an elution solution (50 mM $NaH_2PO_4$—NaOH (pH 8.0), 150 mM NaCl, and 20 to 200 mM imidazole). The eluted fraction of LFC was checked by gel electrophoresis (SDS-PAGE).

The eluted fraction of LFC was collected, and the solution was replaced with a reaction solution (20 mM Tris-HCl (pH 8.0), 150 mM NaCl, and 10 mM $CaCl_2$) by ultrafiltration. Subsequently, factor Xa was added to the solution to a concentration of 3.3 μg/mL, and the mixture was left to stand for two days at room temperature. Thus, the His tag was released from the N-terminal of LFC.

The above-mentioned reaction solution was applied to a sepharose column (benzamidine-Sepharose column, inner diameter: 0.25 cm×length: 1.5 cm), and factor Xa was eliminated by adsorbing factor Xa to the column. Subsequently, a flow-through fraction (flow-through) of the column was applied to a nickel column (nickel-nitrilotriacetic acid-agarose column, inner diameter: 0.25 cm×length: 1.5 cm), and the His tag released from LFC was eliminated by adsorbing the His tag to the column. The flow-through fraction of the column was used as LFC in the subsequent test.

<Reference Example 6> Production of LFB (1) Production of LFB Expression Vector

An expression vector for *Limulus polyphemus* factor B (LFB) was produced according to the following procedure.

A DNA encoding the full-length sequence of LFB (DNA having a base sequence represented by base numbers 1 to 1200 of SEQ ID NO: 3) was produced by a PCR reaction using Tks Gflex DNA polymerase. As a template for the PCR reaction, a vector obtained by inserting a DNA encoding LFB into pBluescript II SK(+) was used. Furthermore, as primers for the PCR reaction, Primer 15 (SEQ ID NO: 36) and Primer 18 (SEQ ID NO: 39) were used.

The DNA obtained by the above-described PCR reaction was purified, and the DNA was subjected to limited digestion using restriction enzymes (EcoR I and Xho I) and preparative separation. pCA7 vector was subjected to limited digestion using restriction enzymes (EcoR I and Xho I) and preparative separation, and then a ligation reaction between the DNA and the pCA7 vector was carried out. *Escherichia coli* was transformed using the above-mentioned ligation reaction liquid, and then amplification and purification of the vector were carried out. The base sequence of the vector was subjected to a sequence analysis, and it was confirmed that there was no introduction of mutation caused by PCR error. In this manner, an expression vector for the polypeptide having the full-length sequence of LFB was obtained.

A PCR reaction was carried out using the above-mentioned vector as a template and using Primer 15 (SEQ ID NO: 36) and Primer 19 (SEQ ID NO: 40), and the DNA thus amplified was purified. The DNA was subjected to limited digestion using restriction enzymes (EcoR I and Xho I) and preparative separation, and thus a DNA fragment (DNA having a base sequence represented by base numbers 1 to 1200 of SEQ ID NO: 3 and a base sequence encoding the 6×His tag, the DNA having the sticky end of EcoR I at the 5'-terminal and the sticky end of Xho I at the 3'-terminal) was obtained.

The pCA7 vector was subjected to limited digestion using restriction enzymes (EcoR I and Xho I) and preparative separation, and then a ligation reaction between the pCA7 vector and the DNA was carried out. *Escherichia coli* was transformed using the above-mentioned ligation reaction, and amplification and purification of the vector were carried out. The base sequence of the vector was subjected to a sequence analysis, and it was confirmed that there was no introduction of mutation caused by PCR error. In this manner, an expression vector for a polypeptide having the 6×His tag on the C-terminal side of the full-length sequence of LFB was obtained.

A PCR reaction was carried out using the above-mentioned vector as a template and using Primer 20 (SEQ ID NO: 41) and Primer 21 (SEQ ID NO: 42), and an amplified DNA was purified. The DNA was subjected to limited digestion using restriction enzymes (Age I and Xho I) and preparative separation, and a DNA fragment (DNA having a base sequence represented by base numbers 70 to 1200 of SEQ ID NO: 3 and a base sequence encoding the 6×His tag, the DNA having the sticky end of Age I at the 5'-terminal and the sticky end of Xho I at the 3'-terminal) was obtained.

The pCA7 vector was subjected to limited digestion using restriction enzymes (Age I and Xho I) and preparative separation, and then a ligation reaction between the pCA7 vector and the DNA was carried out. *Escherichia coli* was transformed using the above-mentioned ligation reaction liquid, and then amplification and purification of the vector were carried out. The base sequence of the vector was subjected to a sequence analysis, and it was confirmed that there was no introduction of mutation caused by PCR error. In this manner, an expression vector for a polypeptide having the 6×His tag on the C-terminal side of the LFB sequence excluding the signal sequence of the N-terminal (LFB/pCA7) was obtained.

(2) Production of LFB

*Limulus polyphemus* factor B (LFB) was produced by a mammalian cell expression system according to the following procedure. Cell culture was carried out under the conditions of 37° C. and 5% $CO_2$.

The same operation as that employed in "(2) Production of LFC" in <Reference Example 5> was carried out, except that the expression vector for LFB (LFB/pCA7) obtained in the section (1) was used instead of the expression vector for LFC (LFC/pCA7), and benzamidine was not added. Thus, a culture fluid including LFB secreted from cells was obtained.

The culture fluid was applied to a nickel column (nickel-nitrilotriacetic acid-agarose column, inner diameter: 1.0 cm×length: 1.5 cm), and an eluted fraction of LFB was obtained. Column purification was carried out according to the procedure described in "(2) Production of LFC") in <Reference Example 5>.

An eluted fraction of LFB was collected, and the solution was substituted with a reaction solution (20 mM Tris-HCl (pH 8.0) and 300 mM NaCl) by ultrafiltration. The LFB thus obtained was used in the subsequent test.

<Example 4> Production of Murasame-LFB

An expression vector for a *Limulus polyphemus* factor B variant (Murasame-LFB) was produced according to the following procedure.

A DNA encoding the N-terminal side of Murasame-LFB (DNA having a base sequence represented by base numbers 1 to 594 of SEQ ID NO: 9; hereinafter, referred to as "DNA fragment 9") was produced by a PCR reaction using Tks Gflex DNA polymerase. As a template for the PCR reaction, a vector obtained by inserting a DNA encoding LFB into pCA7 was used. As primers for the PCR reaction, Primer 15 (SEQ ID NO: 36) and Primer 16 (SEQ ID NO: 37) were used.

A DNA encoding the C-terminal side of Murasame-LFB (DNA having a base sequence represented by base numbers 562 to 1200 of SEQ ID NO: 9; hereinafter, referred to as "DNA fragment 10") was produced by a PCR reaction in the same manner as described above. As primers for the PCR reaction, Primer 17 (SEQ ID NO: 38) and Primer 18 (SEQ ID NO: 39) were used.

The DNA obtained by the PCR reaction was purified, and DNA fragment 9 and DNA fragment 10 were obtained.

A DNA encoding the full-length sequence of Murasame-LFB (DNA having a base sequence represented by base numbers 1 to 1200 of SEQ ID NO: 9) was produced by a PCR reaction using Tks Gflex DNA polymerase. As a template for the PCR reaction, a mixture of DNA fragment 9 and DNA fragment 10 was used. Furthermore, as primers for the PCR reaction, Primer 15 (SEQ ID NO: 36) and Primer 18 (SEQ ID NO: 39) were used. Subsequently, the same operation as that employed in "(1) Production of LFB expression vector" in <Reference Example 6> was carried out. In this manner, an expression vector for a polypeptide having the 6×His tag on the C-terminal side of the Murasame-LFB sequence excluding the signal sequence of the N-terminal (Murasame-LFB/pCA7) was obtained.

(2) Production of Murasame-LFB

A *Limulus polyphemus* factor B variant (Murasame-LFB) was produced by a mammalian cell expression system according to the following procedure. Cell culture was carried out under the conditions of 37° C. and 5% $CO_2$.

The same operation as that employed in "(2) Production of LFB" in <Reference Example 6> was carried out using the expression vector for Murasame-LFB (Murasame-LFB/pCA7) obtained in the section (1) was used instead of the expression vector for LFB (LFB/pCA7). The Murasame-LFB thus obtained was used in the subsequent test.

<Reference Example 7> Measurement of Protease Activity (Specific Activity) of LFB A solution of 160 nM LFC, 3.2 μM LPS, 20 mM Tris-HCl (pH 8.0), and 150 mM NaCl was produced, and the solution was left to stand for 20 minutes at 37° C. Thus, LFC was activated. Hereinafter, the activated LFC will be referred to as "α-LFC".

20 μL of a solution of 50 nM LEE, 2 nM α-LFC, 20 mM Tris-HCl (pH 8.0), 150 mM NaCl, and 100 μg/mL BSA was produced, and the solution was left to stand for one hour at 37° C. To this solution, 5 μL of 2 mM Boc-Leu-Thr-Arg-MCA dissolved in 20% DMF was added, and the mixture was left to stand for 5 minutes at 37° C. 0.6 M Acetic acid (75 μL) was added thereto to terminate the enzyme reaction, and then the amount of MCA released from the peptide (properly proportional to the protease activity (total activity) of activated LFB) was measured with a fluorescence detector. The detection was carried out under the conditions of an excitation wavelength of 380 nm and a fluorescence wavelength of 440 nm.

As a result of the above-described detection, the protease activity (specific activity) of LFB was 44.67±0.61 units/μmol.

<Example 5> Measurement of Protease Activity (Specific Activity) of Murasame-LFB The same operation as that employed in <Reference Example 7> was carried out using Murasame-LFB instead of LFB, and the protease activity of the Murasame-LFB was measured.

As a result of the above-described test, the protease activity (specific activity) of Murasame-LFB was 320.80±9.56 units/μmol.

As a result of the above-described test, it was found that, similarly to Murasame-TFB, Murasame-LFB has higher protease activity (specific activity) than the polypeptide before modification (LFB).

<Reference Example 8> Evaluation of Thermal Stability of LFB

10 μL of a solution of 100 nM LFB, 20 mM Tris-HCl (pH 8.0), 150 mM NaCl, and 100 μg/mL BSA was produced, and the solution was left to stand for 2 minutes at a predetermined temperature (40° C., 50° C., 60° C., 70° C., 80° C., or 90° C.). Subsequently, to this solution, 10 μL of a solution of 4 nM α-LFC, 20 mM Tris-HCl (pH 8.0), 150 mM NaCl, and 100 μg/mL BSA was added, and the mixture was left to stand for one hour at 37° C. Subsequently, the same operation as that employed in <Reference Example 7> was carried out, and the protease activity of LFB was measured. The results of the above-described test are presented in Table 3.

TABLE 3

| Temperature | Relative activity |
| --- | --- |
| 40° C. | 90.20% |
| 50° C. | 69.19% |
| 60° C. | 0.0% |
| 70° C. | 0.0% |
| 80° C. | 0.0% |
| 90° C. | 0.0% |

The "relative activity" in Table 3 is a numerical value (%) expressing, in percentage, a value obtained by dividing the protease activity (specific activity) of LFB that had been left to stand for 2 minutes at each of the various temperatures, by the protease activity (specific activity) of LFB shown in <Reference Example 7>.

<Example 6> Evaluation of Thermal Stability of Murasame-LFB

The same operation as that employed in <Reference Example 8> was carried out using Murasame-LFB instead of LFB, and the thermal stability of Murasame-LFB was evaluated. The results of the above-described test are presented in Table 4.

TABLE 4

| Temperature | Relative activity |
| --- | --- |
| 40° C. | 90.96% |
| 50° C. | 84.37% |
| 60° C. | 70.43% |
| 70° C. | 50.00% |

TABLE 4-continued

| Temperature | Relative activity |
| --- | --- |
| 80° C. | 33.80% |
| 90° C. | 26.41% |

The relative activity in Table 4 is a numerical value (%) expressing, in percentage, a value obtained by dividing the protease activity (specific activity) of Murasame-LFB that had been left to stand for 2 minutes at each of the various temperatures, by the protease activity (specific activity) of Murasame-LFB shown in <Example 5>.

From the results of the above-described test, it was found that similarly to Murasame-TFB, Murasame-LFB has higher thermal stability than the polypeptide before modification (LFB).

INDUSTRIAL APPLICABILITY

According to the present invention, a polypeptide having a protease activity superior to that of naturally occurring horseshoe crab factor B can be produced. Therefore, the polypeptide provided by the present invention is expected to be a horseshoe crab factor B variant that can enhance the sensitivity of endotoxin measurement, compared to naturally occurring horseshoe crab factor B. Furthermore, according to the present invention, a polypeptide having a thermal stability superior to that of naturally occurring horseshoe crab factor B can be produced. Therefore, the polypeptide provided by the present invention is expected to be a horseshoe crab factor B variant having excellent storage stability as a reagent, compared to naturally occurring horseshoe crab factor B.

EXPLANATION OF SEQUENCE LISTING

SEQ ID NO: 1: Base sequence of cDNA of *Tachypleus tridentatus* factor B
SEQ ID NO: 2: Amino acid sequence of *Tachypleus tridentatus* factor B
SEQ ID NO: 3: Base sequence of cDNA of *Limulus polyphemus* factor B
SEQ ID NO: 4: Amino acid sequence of *Limulus polyphemus* factor B
SEQ ID NO: 5: Base sequence (1) of cDNA of *Tachypleus tridentatus* factor B variant
SEQ ID NO: 6: Base sequence (2) of cDNA of *Tachypleus tridentatus* factor B variant
SEQ ID NO: 7: Amino acid sequence of *Tachypleus tridentatus* factor B variant
SEQ ID NO: 8: Base sequence (1) of cDNA of *Limulus polyphemus* factor B variant
SEQ ID NO: 9: Base sequence (2) of cDNA of *Limulus polyphemus* factor B variant
SEQ ID NO: 10: Amino acid sequence of *Limulus polyphemus* factor B variant
SEQ ID NO: 11: Base sequence of cDNA of *Tachypleus tridentatus* factor C
SEQ ID NO: 12: Amino acid sequence of *Tachypleus tridentatus* factor C
SEQ ID NO: 13: Base sequence of cDNA of *Limulus polyphemus* factor C
SEQ ID NO: 14: Amino acid sequence of *Limulus polyphemus* factor C
SEQ ID NO: 15: Base sequence of cDNA of *Carcinoscorpius rotundicauda* factor C
SEQ ID NO: 16: Amino acid sequence of *Carcinoscorpius rotundicauda* factor C
SEQ ID NO: 17: Base sequence of cDNA of *Tachypleus tridentatus* proclotting enzyme
SEQ ID NO: 18: Amino acid sequence of *Tachypleus tridentatus* proclotting enzyme
SEQ ID NO: 19: Base sequence of cDNA of *Limulus polyphemus* proclotting enzyme
SEQ ID NO: 20: Amino acid sequence of cDNA of *Limulus polyphemus* proclotting enzyme
SEQ ID NO: 21 to SEQ ID NO: 42: Primers

The invention claimed is:

1. A polypeptide represented by any one of the following (A) to (C):
    (A) a polypeptide having an amino acid sequence represented by the following (A1) or (A2):
        (A1) an amino acid sequence represented by amino acid numbers 1 to 400 of SEQ ID NO: 10; and
        (A2) an amino acid sequence represented by amino acid numbers 24 to 400 of SEQ ID NO: 10,
    (B) a polypeptide having an amino acid sequence including substitution, deletion, insertion, and/or addition of one amino acid residue or a plurality of amino acid residues in the amino acid sequence of the polypeptide represented by the item (A), provided that the cysteine (Cys) residue at the 193-position is neither substituted nor deleted, and having an identity of at least 90% to at least one of the amino acid sequences of the polypeptides represented by item (A), and the polypeptide having the function of horseshoe crab factor B, and
    (C) a fusion polypeptide in which a peptide tag is added to the polypeptide represented by any one of the items (A) to (B), the polypeptide having the function of horseshoe crab factor B,
    wherein the function of horseshoe crab factor B is to be activated in contact with an activated horseshoe crab factor C, and cleaving a horseshoe crab proclotting enzyme.

2. A nucleic acid encoding the polypeptide according to claim 1.

3. A DNA encoding the polypeptide of claim 1, said DNA represented by any one of the following (a) to (b):
    (a) a DNA having a base sequence represented by any one of the following (a1) to (a4):
        (a1) the base sequence represented by base numbers 1 to 1200 of SEQ ID NO: 8;
        (a2) the base sequence represented by base numbers 70 to 1200 of SEQ ID NO: 8;
        (a3) the base sequence represented by base numbers 1 to 1200 of SEQ ID NO: 9; and
        (a4) the base sequence represented by base numbers 70 to 1200 of SEQ ID NO: 9,
    (b) a DNA having the base sequence of a fusion DNA in which a peptide tag-encoding DNA is added to the DNA represented by any one of the items (a), the DNA encoding a polypeptide having the function of horseshoe crab factor B.

4. A vector retaining the nucleic acid according to claim 2.

5. A cell retaining the nucleic acid according to claim 1.

6. A method for producing a polypeptide, the method comprising a step of producing a polypeptide having the function of horseshoe crab factor B using the cell according to claim 5.

7. A method for measuring an endotoxin, the method comprising steps of the following (1) and (2):
    (1) a step of mixing the polypeptide according to claim 1 with horseshoe crab factor C and a test sample; and
    (2) a step of measuring protease activity of the polypeptide.

8. A reagent for endotoxin measurement, the reagent comprising the polypeptide according to claim 1 as a constituent component.

9. A kit for endotoxin measurement, the kit comprising the polypeptide according to claim 1, as a component part.

* * * * *

SEQUENCE LISTING

```
<160> NUMBER OF SEQ ID NOS: 42

<210> SEQ ID NO 1
<211> LENGTH: 1203
<212> TYPE: DNA
<213> ORGANISM: Tachypleus tridentatus
<220> FEATURE:
<223> OTHER INFORMATION: Tachypleus tridentatus factor B

<400> SEQUENCE: 1
atgacgtgga tatgtgtgat aacgttgttt gctctggctt ctgctacgtt gggtaacaaa      60
gttagtagag tgggggtcct cttccccaag acacggaacg acaatgagtg tacagcaaga     120
gggggattga aaggatcctg caaatccctc atagactgtc ctagtgtctt ggctacgttg     180
aaggacagtt ttcctgtcgt ttgctcttgg aatggtcgat ttcagcctat tgtctgctgt     240
cctgatgcaa tagcaccacc acctgtaacc acaacagctg taactgtaat atctacaaaa     300
gaaccaaagc ttccaagatt acatatatca ggttgtggaa aaagaaaagt caaaatagat     360
attacaactg ttggacgctc tggatcacca atacttcctc cgatatctac tcctcaaaat     420
tcaacaggtg ggagaggaat tattgctgga ggcgtagaag ccaaaattgg cgcgtggcct     480
tggatggcag ctgttttgt gaaaaacttt ggcattggca gattccactg tgctggtagc     540
```

-continued

```
ataatcagta acaagtacat tttgtcagct gcccacgcct tccttatcgg aggtcgaaag      600
ttgaccccaa ctcgcttagc tgtccgtgtg ggaggccact acataaagag gggtcaagag      660
tatccagtga agacgtgat tatccatcct cattatgtag aaaaggagaa ctacaatgat       720
atagccataa tcgagttaaa agaggaactg aactttacgg acttggtcaa tcctatatgt     780
ctccctgatc cagagacagt aacggatcca ttaaaagaca gaattgtgac tgcagcggga    840
tggggcgatc tggatttctc cggtccacgg agccaagttc tacgtgaggt aagcatccca    900
gttgttccag ttgataaatg tgatcaagcc tatgagaaac tcaacacccc ttcactaaaa    960
aatgggataa cgaataactt cctttgcgct ggattggaag aaggagggaa agacgcttgc   1020
caaggcgatt ctggtggacc gttgatgcta gtgaacaaca ctaggtggat agtagtagga   1080
gttgtgtcgt tcgggcacaa gtgtgccgag gaaggatatc ctggtgtgta ctcgcgcgta   1140
gcgagttacc tagactggat cgcgaaagtt acgaactcgt tagatcatgc cgtcactaac   1200
tga                                                                  1203
```

<210> SEQ ID NO 2
<211> LENGTH: 400
<212> TYPE: PRT
<213> ORGANISM: Tachypleus tridentatus
<220> FEATURE:
<223> OTHER INFORMATION: Tachypleus tridentatus factor B

<400> SEQUENCE: 2

```
Met Thr Trp Ile Cys Val Ile Thr Leu Phe Ala Leu Ala Ser Ala Thr
1               5                   10                  15

Leu Gly Asn Lys Val Ser Arg Val Gly Val Leu Phe Pro Lys Thr Arg
            20                  25                  30

Asn Asp Asn Glu Cys Thr Ala Arg Gly Gly Leu Lys Gly Ser Cys Lys
        35                  40                  45

Ser Leu Ile Asp Cys Pro Ser Val Leu Ala Thr Leu Lys Asp Ser Phe
    50                  55                  60

Pro Val Val Cys Ser Trp Asn Gly Arg Phe Gln Pro Ile Val Cys Cys
65                  70                  75                  80

Pro Asp Ala Ile Ala Pro Pro Val Thr Thr Thr Ala Val Thr Val
                85                  90                  95

Ile Ser Thr Lys Glu Pro Lys Leu Pro Arg Leu His Ile Ser Gly Cys
            100                 105                 110

Gly Lys Arg Lys Val Lys Ile Asp Ile Thr Thr Val Gly Arg Ser Gly
        115                 120                 125

Ser Pro Ile Leu Pro Pro Ile Ser Thr Pro Gln Asn Ser Thr Gly Gly
    130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Asn Lys Tyr Ile Leu Ser Ala Ala His
            180                 185                 190

Ala Phe Leu Ile Gly Gly Arg Lys Leu Thr Pro Thr Arg Leu Ala Val
        195                 200                 205

Arg Val Gly Gly His Tyr Ile Lys Arg Gly Gln Glu Tyr Pro Val Lys
    210                 215                 220

Asp Val Ile Ile His Pro His Tyr Val Glu Lys Glu Asn Tyr Asn Asp
225                 230                 235                 240
```

```
Ile Ala Ile Ile Glu Leu Lys Glu Glu Leu Asn Phe Thr Asp Leu Val
                245                 250                 255

Asn Pro Ile Cys Leu Pro Asp Pro Glu Thr Val Thr Asp Pro Leu Lys
            260                 265                 270

Asp Arg Ile Val Thr Ala Ala Gly Trp Gly Asp Leu Asp Phe Ser Gly
        275                 280                 285

Pro Arg Ser Gln Val Leu Arg Glu Val Ser Ile Pro Val Val Pro Val
    290                 295                 300

Asp Lys Cys Asp Gln Ala Tyr Glu Lys Leu Asn Thr Pro Ser Leu Lys
305                 310                 315                 320

Asn Gly Ile Thr Asn Asn Phe Leu Cys Ala Gly Leu Glu Gly Gly
                325                 330                 335

Lys Asp Ala Cys Gln Gly Asp Ser Gly Gly Pro Leu Met Leu Val Asn
            340                 345                 350

Asn Thr Arg Trp Ile Val Val Gly Val Val Ser Phe Gly His Lys Cys
        355                 360                 365

Ala Glu Glu Gly Tyr Pro Gly Val Tyr Ser Arg Val Ala Ser Tyr Leu
    370                 375                 380

Asp Trp Ile Ala Lys Val Thr Asn Ser Leu Asp His Ala Val Thr Asn
385                 390                 395                 400
```

<210> SEQ ID NO 3
<211> LENGTH: 1203
<212> TYPE: DNA
<213> ORGANISM: Limulus polyphemus
<220> FEATURE:
<223> OTHER INFORMATION: Limulus polyphemus factor B

<400> SEQUENCE: 3

```
atggcgtgga tttgtgtgat aacgttgttt gctttggctt ctagtacgtt gagtaataaa    60
gttagtagag tggggatcat cttcctaag acacagaacg ataataaaca gtgtacagca   120
aaaggtggat taaagggtc ctgcaagtcc ctcacagact gtcctgctgt cttggctacg   180
ttgaaggata gtttccctgt cgtttgctct tggaatggtc ggtttcagcc tattgtatgt   240
tgtcctgatg cagcagcacc aagtgtaacc acaacagtta caactattgt ccctacaaaa   300
gaaacaaaga ttccaagatt acatatacca ggttgtggaa aagaaaagt aaatgtagat   360
attacaacta ttggacgttc ggggtcacca atacttcctc ccatatctac ttctcaagat   420
ttgaagggtg ggagaggaat cattgctgga ggtgtagaag ctaaaattgg cgcctggcct   480
tggatggcag ctgttttgt gaaaaatttt ggcattggca gattccattg tgctggtagc   540
ataatcagta gcaagtacat tttgtctgct gcccacgctt tcctcattgg aggtcgaaag   600
ctgaccccaa ctcgcttagc tgtccgcgta ggaggccact acgtaaagat gggtcaagaa   660
tatcatgtgg aagatgtgat tatccatcct gactacgtag aaagggagaa ttacaatgat   720
attgctatca ttgtgttaaa agaggaactg aattttactg atttggtccg tccaatctgt   780
ctccctgacc cagaggcagt aacagattca ttaaaaggca aagggtgac agtagctgga   840
tggggtgatc tggatttcgc cggtccacga agtcaagttc tgcgcgaggt tagtatcccc   900
gttgttccaa tcggtgactg taacaaagcc atcagaagc tcaacaccct tgctcttaaa   960
aatgggataa cgaaaaagtt tatttgtgct ggattggaag aaggtgggaa agatgcttgt  1020
caaggcgatt ctggtggacc gttgatgcta gtgaacaata tgagttggat agtgacggga  1080
gtggtgtcgt tcggacacaa gtgtgccgaa gagggatttc ctggtgtgta cacgcgtgta  1140
gtgagttacc tagagtggat cgcgaaggtt acgaactcgt tagaccagac agtcactaac  1200
```

```
tga                                                      1203
```

<210> SEQ ID NO 4
<211> LENGTH: 400
<212> TYPE: PRT
<213> ORGANISM: Limulus polyphemus
<220> FEATURE:
<223> OTHER INFORMATION: Limulus polyphemus factor B
<400> SEQUENCE: 4

| Met | Ala | Trp | Ile | Cys | Val | Ile | Thr | Leu | Phe | Ala | Leu | Ala | Ser | Ser | Thr |
|---|---|---|---|---|---|---|---|---|---|---|---|---|---|---|---|
| 1 | | | | 5 | | | | | 10 | | | | | 15 | |

| Leu | Ser | Asn | Lys | Val | Ser | Arg | Val | Gly | Ile | Ile | Phe | Pro | Lys | Thr | Gln |
|---|---|---|---|---|---|---|---|---|---|---|---|---|---|---|---|
| | | | 20 | | | | | 25 | | | | | 30 | | |

| Asn | Asp | Asn | Lys | Gln | Cys | Thr | Ala | Lys | Gly | Gly | Leu | Lys | Gly | Ser | Cys |
|---|---|---|---|---|---|---|---|---|---|---|---|---|---|---|---|
| | | 35 | | | | | 40 | | | | | 45 | | | |

| Lys | Ser | Leu | Thr | Asp | Cys | Pro | Ala | Val | Leu | Ala | Thr | Leu | Lys | Asp | Ser |
|---|---|---|---|---|---|---|---|---|---|---|---|---|---|---|---|
| | 50 | | | | | 55 | | | | | 60 | | | | |

| Phe | Pro | Val | Val | Cys | Ser | Trp | Asn | Gly | Arg | Phe | Gln | Pro | Ile | Val | Cys |
|---|---|---|---|---|---|---|---|---|---|---|---|---|---|---|---|
| 65 | | | | | 70 | | | | | 75 | | | | | 80 |

| Cys | Pro | Asp | Ala | Ala | Pro | Ser | Val | Thr | Thr | Thr | Val | Thr | Thr | Thr | Ile |
|---|---|---|---|---|---|---|---|---|---|---|---|---|---|---|---|
| | | | | 85 | | | | | 90 | | | | | 95 | |

| Val | Pro | Thr | Lys | Glu | Thr | Lys | Ile | Pro | Arg | Leu | His | Ile | Pro | Gly | Cys |
|---|---|---|---|---|---|---|---|---|---|---|---|---|---|---|---|
| | | | 100 | | | | | 105 | | | | | 110 | | |

| Gly | Lys | Arg | Lys | Val | Asn | Val | Asp | Ile | Thr | Thr | Ile | Gly | Arg | Ser | Gly |
|---|---|---|---|---|---|---|---|---|---|---|---|---|---|---|---|
| | | 115 | | | | | 120 | | | | | 125 | | | |

| Ser | Pro | Ile | Leu | Pro | Pro | Ile | Ser | Thr | Ser | Gln | Asp | Leu | Lys | Gly | Gly |
|---|---|---|---|---|---|---|---|---|---|---|---|---|---|---|---|
| | 130 | | | | | 135 | | | | | 140 | | | | |

| Arg | Gly | Ile | Ile | Ala | Gly | Gly | Val | Glu | Ala | Lys | Ile | Gly | Ala | Trp | Pro |
|---|---|---|---|---|---|---|---|---|---|---|---|---|---|---|---|
| 145 | | | | | 150 | | | | | 155 | | | | | 160 |

| Trp | Met | Ala | Ala | Val | Phe | Val | Lys | Asn | Phe | Gly | Ile | Gly | Arg | Phe | His |
|---|---|---|---|---|---|---|---|---|---|---|---|---|---|---|---|
| | | | | 165 | | | | | 170 | | | | | 175 | |

| Cys | Ala | Gly | Ser | Ile | Ile | Ser | Ser | Lys | Tyr | Ile | Leu | Ser | Ala | Ala | His |
|---|---|---|---|---|---|---|---|---|---|---|---|---|---|---|---|
| | | | 180 | | | | | 185 | | | | | 190 | | |

| Ala | Phe | Leu | Ile | Gly | Gly | Arg | Lys | Leu | Thr | Pro | Thr | Arg | Leu | Ala | Val |
|---|---|---|---|---|---|---|---|---|---|---|---|---|---|---|---|
| | | 195 | | | | | 200 | | | | | 205 | | | |

| Arg | Val | Gly | Gly | His | Tyr | Val | Lys | Met | Gly | Gln | Glu | Tyr | His | Val | Glu |
|---|---|---|---|---|---|---|---|---|---|---|---|---|---|---|---|
| | 210 | | | | | 215 | | | | | 220 | | | | |

| Asp | Val | Ile | Ile | His | Pro | Asp | Tyr | Val | Glu | Arg | Glu | Asn | Tyr | Asn | Asp |
|---|---|---|---|---|---|---|---|---|---|---|---|---|---|---|---|
| 225 | | | | | 230 | | | | | 235 | | | | | 240 |

| Ile | Ala | Ile | Ile | Val | Leu | Lys | Glu | Glu | Leu | Asn | Phe | Thr | Asp | Leu | Val |
|---|---|---|---|---|---|---|---|---|---|---|---|---|---|---|---|
| | | | | 245 | | | | | 250 | | | | | 255 | |

| Arg | Pro | Ile | Cys | Leu | Pro | Asp | Pro | Glu | Ala | Val | Thr | Asp | Ser | Leu | Lys |
|---|---|---|---|---|---|---|---|---|---|---|---|---|---|---|---|
| | | | 260 | | | | | 265 | | | | | 270 | | |

| Gly | Arg | Arg | Val | Thr | Val | Ala | Gly | Trp | Gly | Asp | Leu | Asp | Phe | Ala | Gly |
|---|---|---|---|---|---|---|---|---|---|---|---|---|---|---|---|
| | | 275 | | | | | 280 | | | | | 285 | | | |

| Pro | Arg | Ser | Gln | Val | Leu | Arg | Glu | Val | Ser | Ile | Pro | Val | Val | Pro | Ile |
|---|---|---|---|---|---|---|---|---|---|---|---|---|---|---|---|
| | 290 | | | | | 295 | | | | | 300 | | | | |

| Gly | Asp | Cys | Asn | Lys | Ala | Tyr | Gln | Lys | Leu | Asn | Thr | Leu | Ala | Leu | Lys |
|---|---|---|---|---|---|---|---|---|---|---|---|---|---|---|---|
| 305 | | | | | 310 | | | | | 315 | | | | | 320 |

| Asn | Gly | Ile | Thr | Lys | Lys | Phe | Ile | Cys | Ala | Gly | Leu | Glu | Glu | Gly | Gly |
|---|---|---|---|---|---|---|---|---|---|---|---|---|---|---|---|
| | | | | 325 | | | | | 330 | | | | | 335 | |

| Lys | Asp | Ala | Cys | Gln | Gly | Asp | Ser | Gly | Gly | Pro | Leu | Met | Leu | Val | Asn |
|---|---|---|---|---|---|---|---|---|---|---|---|---|---|---|---|
| | | | 340 | | | | | 345 | | | | | 350 | | |

Asn Ser Ser Trp Ile Val Thr Gly Val Val Ser Phe Gly His Lys Cys
            355                 360                 365

Ala Glu Glu Gly Phe Pro Gly Val Tyr Thr Arg Val Val Ser Tyr Leu
    370                 375                 380

Glu Trp Ile Ala Lys Val Thr Asn Ser Leu Asp Gln Thr Val Thr Asn
385                 390                 395                 400

<210> SEQ ID NO 5
<211> LENGTH: 1203
<212> TYPE: DNA
<213> ORGANISM: Artificial Sequence
<220> FEATURE:
<223> OTHER INFORMATION: Tachypleus tridentatus factor B variant

<400> SEQUENCE: 5

| | | | | |
|---|---|---|---|---|
| atgacgtgga | tatgtgtgat | aacgttgttt | gctctggctt | ctgctacgtt | gggtaacaaa | 60 |
| gttagtagag | tgggggtcct | cttccccaag | acacggaacg | acaatgagtg | tacagcaaga | 120 |
| ggggattga | aaggatcctg | caaatccctc | atagactgtc | ctagtgtctt | ggctacgttg | 180 |
| aaggacagtt | ttcctgtcgt | ttgctcttgg | aatggtcgat | ttcagcctat | tgtctgctgt | 240 |
| cctgatgcaa | tagcaccacc | acctgtaacc | acaacagctg | taactgtaat | atctacaaaa | 300 |
| gaaccaaagc | ttccaagatt | acatatatca | ggttgtggaa | aaagaaaagt | caaaatagat | 360 |
| attacaactg | ttgacgctc | tggatcacca | atacttcctc | cgatatctac | tcctcaaaat | 420 |
| tcaacaggtg | ggagaggaat | tattgctgga | ggcgtagaag | ccaaaattgg | cgcgtggcct | 480 |
| tggatggcag | ctgtttttgt | gaaaaacttt | ggcattggca | gattccactg | tgctggtagc | 540 |
| ataatcagta | acaagtacat | tttgtcagct | gcccactgtt | tccttatcgg | aggtcgaaag | 600 |
| ttgaccccaa | ctcgcttagc | tgtccgtgtg | ggaggccact | acataaagag | gggtcaagag | 660 |
| tatccagtga | aagacgtgat | tatccatcct | cattatgtag | aaaaggagaa | ctacaatgat | 720 |
| atagccataa | tcgagttaaa | agaggaactg | aactttacgg | acttggtcaa | tcctatatgt | 780 |
| ctccctgatc | cagagacagt | aacggatcca | ttaaaagaca | gaattgtgac | tgcagcggga | 840 |
| tggggcgatc | tggatttctc | cggtccacgg | agccaagttc | tacgtgaggt | aagcatccca | 900 |
| gttgttccag | ttgataaatg | tgatcaagcc | tatgagaaac | tcaacacccc | ttcactaaaa | 960 |
| aatgggataa | cgaataactt | cctttgcgct | ggattggaag | aaggagggaa | agacgcttgc | 1020 |
| caaggcgatt | ctggtggacc | gttgatgcta | gtgaacaaca | ctaggtggat | agtagtagga | 1080 |
| gttgtgtcgt | tcgggcacaa | gtgtgccgag | gaaggatatc | ctggtgtgta | ctcgcgcgta | 1140 |
| gcgagttacc | tagactggat | cgcgaaagtt | acgaactcgt | tagatcatgc | cgtcactaac | 1200 |
| tga | | | | | 1203 |

<210> SEQ ID NO 6
<211> LENGTH: 1203
<212> TYPE: DNA
<213> ORGANISM: Artificial Sequence
<220> FEATURE:
<223> OTHER INFORMATION: Tachypleus tridentatus factor B variant

<400> SEQUENCE: 6

| | | | | |
|---|---|---|---|---|
| atgacgtgga | tatgtgtgat | aacgttgttt | gctctggctt | ctgctacgtt | gggtaacaaa | 60 |
| gttagtagag | tgggggtcct | cttccccaag | acacggaacg | acaatgagtg | tacagcaaga | 120 |
| ggggattga | aaggatcctg | caaatccctc | atagactgtc | ctagtgtctt | ggctacgttg | 180 |
| aaggacagtt | ttcctgtcgt | ttgctcttgg | aatggtcgat | ttcagcctat | tgtctgctgt | 240 |

```
cctgatgcaa tagcaccacc acctgtaacc acaacagctg taactgtaat atctacaaaa      300
gaaccaaagc ttccaagatt acatatatca ggttgtggaa aaagaaaagt caaaatagat      360
attacaactg ttggacgctc tggatcacca atacttcctc cgatatctac tcctcaaaat      420
tcaacaggtg ggagaggaat tattgctgga ggcgtagaag ccaaaattgg cgcgtggcct      480
tggatggcag ctgtttttgt gaaaaacttt ggcattggca gattccactg tgctggtagc      540
ataatcagta acaagtacat tttgtcagct gcccactgct tccttatcgg aggtcgaaag      600
ttgaccccaa ctcgcttagc tgtccgtgtg ggaggccact acataaagag gggtcaagag      660
tatccagtga agacgtgat tatccatcct cattatgtag aaaaggagaa ctacaatgat      720
atagccataa tcgagttaaa agaggaactg aactttacgg acttggtcaa tcctatatgt      780
ctccctgatc cagagacagt aacggatcca ttaaaagaca gaattgtgac tgcagcggga      840
tggggcgatc tggatttctc cggtccacgg agccaagttc tacgtgaggt aagcatccca      900
gttgttccag ttgataaatg tgatcaagcc tatgagaaac tcaacacccc ttcactaaaa      960
aatgggataa cgaataactt cctttgcgct ggattggaag aaggagggaa agacgcttgc     1020
caaggcgatt ctggtggacc gttgatgcta gtgaacaaca ctaggtggat agtagtagga     1080
gttgtgtcgt tcgggcacaa gtgtgccgag gaaggatatc ctggtgtgta ctcgcgcgta     1140
gcgagttacc tagactggat cgcgaaagtt acgaactcgt tagatcatgc cgtcactaac     1200
tga                                                                   1203

<210> SEQ ID NO 7
<211> LENGTH: 400
<212> TYPE: PRT
<213> ORGANISM: Artificial Sequence
<220> FEATURE:
<223> OTHER INFORMATION: Tachypleus tridentatus factor B variant

<400> SEQUENCE: 7

Met Thr Trp Ile Cys Val Ile Thr Leu Phe Ala Leu Ala Ser Ala Thr
1               5                   10                  15

Leu Gly Asn Lys Val Ser Arg Val Gly Val Leu Phe Pro Lys Thr Arg
            20                  25                  30

Asn Asp Asn Glu Cys Thr Ala Arg Gly Gly Leu Lys Gly Ser Cys Lys
        35                  40                  45

Ser Leu Ile Asp Cys Pro Ser Val Leu Ala Thr Leu Lys Asp Ser Phe
    50                  55                  60

Pro Val Val Cys Ser Trp Asn Gly Arg Phe Gln Pro Ile Val Cys Cys
65                  70                  75                  80

Pro Asp Ala Ile Ala Pro Pro Val Thr Thr Thr Ala Val Thr Val
                85                  90                  95

Ile Ser Thr Lys Glu Pro Lys Leu Pro Arg Leu His Ile Ser Gly Cys
                100                 105                 110

Gly Lys Arg Lys Val Lys Ile Asp Ile Thr Thr Val Gly Arg Ser Gly
            115                 120                 125

Ser Pro Ile Leu Pro Pro Ile Ser Thr Pro Gln Asn Ser Thr Gly Gly
        130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Asn Lys Tyr Ile Leu Ser Ala Ala His
                180                 185                 190
```

Cys Phe Leu Ile Gly Gly Arg Lys Leu Thr Pro Thr Arg Leu Ala Val
            195                 200                 205

Arg Val Gly Gly His Tyr Ile Lys Arg Gly Gln Glu Tyr Pro Val Lys
        210                 215                 220

Asp Val Ile Ile His Pro His Tyr Val Glu Lys Glu Asn Tyr Asn Asp
225                 230                 235                 240

Ile Ala Ile Ile Glu Leu Lys Glu Leu Asn Phe Thr Asp Leu Val
                245                 250                 255

Asn Pro Ile Cys Leu Pro Asp Pro Glu Thr Val Thr Asp Pro Leu Lys
            260                 265                 270

Asp Arg Ile Val Thr Ala Ala Gly Trp Gly Asp Leu Asp Phe Ser Gly
            275                 280                 285

Pro Arg Ser Gln Val Leu Arg Glu Val Ser Ile Pro Val Pro Val
    290                 295                 300

Asp Lys Cys Asp Gln Ala Tyr Glu Lys Leu Asn Thr Pro Ser Leu Lys
305                 310                 315                 320

Asn Gly Ile Thr Asn Asn Phe Leu Cys Ala Gly Leu Glu Glu Gly Gly
                325                 330                 335

Lys Asp Ala Cys Gln Gly Asp Ser Gly Gly Pro Leu Met Leu Val Asn
            340                 345                 350

Asn Thr Arg Trp Ile Val Val Gly Val Ser Phe Gly His Lys Cys
            355                 360                 365

Ala Glu Glu Gly Tyr Pro Gly Val Tyr Ser Arg Val Ala Ser Tyr Leu
        370                 375                 380

Asp Trp Ile Ala Lys Val Thr Asn Ser Leu Asp His Ala Val Thr Asn
385                 390                 395                 400

<210> SEQ ID NO 8
<211> LENGTH: 1203
<212> TYPE: DNA
<213> ORGANISM: Artificial Sequence
<220> FEATURE:
<223> OTHER INFORMATION: Limulus polyphemus factor B variant

<400> SEQUENCE: 8
atggcgtgga tttgtgtgat aacgttgttt gctttggctt ctagtacgtt gagtaataaa      60
gttagtagag tggggatcat cttttcctaag cacagaacg ataataaaca gtgtacagca     120
aaaggtggat taaagggtc ctgcaagtcc ctcacagact gtcctgctgt cttggctacg     180
ttgaaggata gtttccctgt cgtttgctct tggaatggtc ggtttcagcc tattgtatgt     240
tgtcctgatg cagcagcacc aagtgtaacc acaacagtta caactattgt ccctacaaaa     300
gaaacaaaga ttccaagatt acatatacca ggttgtggaa aaagaaaagt aaatgtagat     360
attacaacta ttggacgttc ggggtcacca atacttcctc ccatatctac ttctcaagat     420
ttgaagggtg ggagaggaat cattgctgga ggtgtagaag ctaaaattgg cgcctggcct     480
tggatggcag ctgttttgt gaaaaatttt ggcattggca gattccattg tgctggtagc     540
ataatcagta gcaagtacat tttgtctgct gcccactgtt tcctcattgg aggtcgaaag     600
ctgaccccaa ctcgcttagc tgtccgcgta ggaggccact acgtaaagat gggtcaagaa     660
tatcatgtgg aagatgtgat tatccatcct gactacgtag aaagggagaa ttacaatgat     720
attgctatca ttgtgttaaa agaggaactg aattttactg atttggtccg tccaatctgt     780
ctccctgacc cagaggcagt aacagattca ttaaaaggca aagggtgac agtagctgga     840 tggggtgatc tggatttcgc cggtccacga agtcaagttc tgcgcgaggt tagtatcccc     900

```
gttgttccaa tcggtgactg taacaaagcc tatcagaagc tcaacaccct tgctcttaaa      960
aatgggataa cgaaaaagtt tatttgtgct ggattggaag aaggtgggaa agatgcttgt     1020
caaggcgatt ctggtggacc gttgatgcta gtgaacaata gtagttggat agtgacggga     1080
gtggtgtcgt tcggacacaa gtgtgccgaa gagggatttc ctggtgtgta cacgcgtgta     1140
gtgagttacc tagagtggat cgcgaaggtt acgaactcgt tagaccagac agtcactaac     1200
tga                                                                   1203
```

<210> SEQ ID NO 9
<211> LENGTH: 1203
<212> TYPE: DNA
<213> ORGANISM: Artificial Sequence
<220> FEATURE:
<223> OTHER INFORMATION: Limulus polyphemus factor B variant

<400> SEQUENCE: 9

```
atggcgtgga tttgtgtgat aacgttgttt gctttggctt ctagtacgtt gagtaataaa       60
gttagtagag tggggatcat ctttcctaag acacagaacg ataataaaca gtgtacagca      120
aaaggtggat aaaagggtc ctgcaagtcc ctcacagact gtcctgctgt cttggctacg       180
ttgaaggata gtttccctgt cgtttgctct tggaatggtc ggtttcagcc tattgtatgt     240
tgtcctgatg cagcagcacc aagtgtaacc acaacagtta caactattgt ccctacaaaa    300
gaaacaaaga ttccaagatt acatatacca ggttgtggaa aaagaaaagt aaatgtagat     360
attacaacta ttggacgttc ggggtcacca atacttcctc ccatatctac ttctcaagat     420
ttgaagggtg ggagaggaat cattgctgga ggtgtagaag ctaaaattgg cgcctggcct     480
tggatggcag ctgttttgt gaaaaatttt ggcattggca gattccattg tgctggtagc     540
ataatcagta gcaagtacat tttgtctgct gcccactgct cctcattgg aggtcgaaag     600
ctgaccccaa ctcgcttagc tgtccgcgta ggaggccact acgtaaagat gggtcaagaa     660
tatcatgtgg aagatgtgat tatccatcct gactacgtag aaagggagaa ttacaatgat     720
attgctatca ttgtgttaaa agaggaactg aatttttactg atttggtccg tccaatctgt     780
ctccctgacc cagaggcagt aacagattca ttaaaaggca aagggtgac agtagctgga     840
tggggtgatc tggatttcgc cggtccacga agtcaagttc tgcgcgaggt tagtatcccc     900
gttgttccaa tcggtgactg taacaaagcc tatcagaagc tcaacaccct tgctcttaaa     960
aatgggataa cgaaaaagtt tatttgtgct ggattggaag aaggtgggaa agatgcttgt    1020
caaggcgatt ctggtggacc gttgatgcta gtgaacaata gtagttggat agtgacggga    1080
gtggtgtcgt tcggacacaa gtgtgccgaa gagggatttc ctggtgtgta cacgcgtgta    1140
gtgagttacc tagagtggat cgcgaaggtt acgaactcgt tagaccagac agtcactaac    1200
tga                                                                  1203
```

<210> SEQ ID NO 10
<211> LENGTH: 400
<212> TYPE: PRT
<213> ORGANISM: Artificial Sequence
<220> FEATURE:
<223> OTHER INFORMATION: Limulus polyphemus factor B variant

<400> SEQUENCE: 10

```
Met Ala Trp Ile Cys Val Ile Thr Leu Phe Ala Leu Ala Ser Ser Thr
1               5                   10                  15

Leu Ser Asn Lys Val Ser Arg Val Gly Ile Ile Phe Pro Lys Thr Gln
```

```
                    20                  25                  30
Asn Asp Asn Lys Gln Cys Thr Ala Lys Gly Gly Leu Lys Gly Ser Cys
                35                  40                  45

Lys Ser Leu Thr Asp Cys Pro Ala Val Leu Ala Thr Leu Lys Asp Ser
            50                  55                  60

Phe Pro Val Val Cys Ser Trp Asn Gly Arg Phe Gln Pro Ile Val Cys
 65                 70                  75                  80

Cys Pro Asp Ala Ala Pro Ser Val Thr Thr Val Thr Thr Ile
                85                  90                  95

Val Pro Thr Lys Glu Thr Lys Ile Pro Arg Leu His Ile Pro Gly Cys
            100                 105                 110

Gly Lys Arg Lys Val Asn Val Asp Ile Thr Thr Ile Gly Arg Ser Gly
            115                 120                 125

Ser Pro Ile Leu Pro Ile Ser Thr Ser Gln Asp Leu Lys Gly Gly
            130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Ser Lys Tyr Ile Leu Ser Ala Ala His
                180                 185                 190

Cys Phe Leu Ile Gly Gly Arg Lys Leu Thr Pro Thr Arg Leu Ala Val
                195                 200                 205

Arg Val Gly Gly His Tyr Val Lys Met Gly Gln Glu Tyr His Val Glu
            210                 215                 220

Asp Val Ile Ile His Pro Asp Tyr Val Glu Arg Glu Asn Tyr Asn Asp
225                 230                 235                 240

Ile Ala Ile Ile Val Leu Lys Glu Glu Leu Asn Phe Thr Asp Leu Val
                245                 250                 255

Arg Pro Ile Cys Leu Pro Asp Pro Glu Ala Val Thr Asp Ser Leu Lys
                260                 265                 270

Gly Arg Arg Val Thr Val Ala Gly Trp Gly Asp Leu Asp Phe Ala Gly
            275                 280                 285

Pro Arg Ser Gln Val Leu Arg Glu Val Ser Ile Pro Val Val Pro Ile
            290                 295                 300

Gly Asp Cys Asn Lys Ala Tyr Gln Lys Leu Asn Thr Leu Ala Leu Lys
305                 310                 315                 320

Asn Gly Ile Thr Lys Lys Phe Ile Cys Ala Gly Leu Glu Glu Gly Gly
                325                 330                 335

Lys Asp Ala Cys Gln Gly Asp Ser Gly Gly Pro Leu Met Leu Val Asn
                340                 345                 350

Asn Ser Ser Trp Ile Val Thr Gly Val Val Ser Phe Gly His Lys Cys
                355                 360                 365

Ala Glu Glu Gly Phe Pro Gly Val Tyr Thr Arg Val Val Ser Tyr Leu
                370                 375                 380

Glu Trp Ile Ala Lys Val Thr Asn Ser Leu Asp Gln Thr Val Thr Asn
385                 390                 395                 400

<210> SEQ ID NO 11
<211> LENGTH: 3060
<212> TYPE: DNA
<213> ORGANISM: Tachypleus tridentatus
<220> FEATURE:
<223> OTHER INFORMATION: Tachypleus tridentatus factor C
```

```
<400> SEQUENCE: 11
atggtcttag cgtcgttttt ggtgtctggt ttagttctag ggatactagc ccaacaaatg      60
cgtccagttc agtccagagg agtagatctg ggcttgtgtg atgaaacgag gttcgagtgt     120
aagtgtggag atccaggcta tgtgttcaac gtccctatga acaatgcac gtacttctat      180 cgatggaggc cttattgtaa accatgtgat gacctggagg ctaaggacat tgtccaaag     240 tacaaacgat gtcaagagtg taaggctggt cttgatagtt gtgttacttg tccacctaac     300
aaatatggta cttggtgtag cggtgaatgt caatgtaaga atggaggtat ctgtgaccag     360
aggacaggag cttgtacctg tcgtgacaga tatgaaggag cgcactgtga aattctcaaa     420
ggttgtcctc ttcttccatc ggattctcaa gttcaggaag tcagaaaccc accagataat     480
ccccaaacta ttgactacag ctgttcacca gggttcaagc ttaaaggcgt ggcacgaatt     540
agctgtctcc caaatggaca gtggagtagc tttccaccca atgtattccg agaatgtgcc     600
aaggtttcat ctccagaaca cgggaaagtg aatgctccta gtggcaatat gatagaaggg     660
gctactttac ggttctcatg tgatagtccc tactacttga ttggtcaaga acattaacc      720 tgccagggta atggtcagtg gagtggacaa ataccacaat gtaagaagtt ggtcttctgt     780
cctgaccttg atcctgtaaa ccatgctgaa caccaggtta aaattggtgt ggaacaaaaa     840
tatggtcagt ttcctcaagg cactgaagtg acctatcgt gttcgggtaa ctacttcttg      900
atgggtttta acaccttaaa atgtaaccct gatgggtcct ggtcaggatc acagccatcc     960
tgtgttaaag tggcagacag agaggtcgac tgtgacagta agctgtaga cttcttggat     1020 gatgttggta aacctgtcag gatccactgt cctgctggct gttctttgac agctggtact     1080
gtgtggggta cagccatata ccacgaactt cctcagtgt gtcgtgcagc catccatgct      1140
ggcaagcttc caaactctgg aggggcggtg catgtagtga acaatggccc ctactcggac     1200
tttctgggta gtgacctgaa tgggataaaa tcggaagagt tgaagtctct tgcccgcagt     1260
tttcgatttg attatgtcag ttcatccaca gcaggtagta caggatgtcc tgatggatgg     1320
tttgaggtag aagagaactg tgtgtacgtt acatcaaaac agagagcctg ggaaagagct     1380
caaggtgtgt gtaccaatat ggctgctcgt cttgctgtgc tagacaaaga tctaattccg     1440
agttccttga ctgagactct acgagggaaa gggttaacaa ccacatggat aggattgcac     1500
agactagatg ctgagaagcc ctttgtttgg gagctaatgg atcgtagtaa tgtggttctg     1560
aatgataacc taacattctg ggcctctggc gaacctggaa atgaaactaa ctgtgtatat     1620
ctggacatcc gagatcagct gcagcctgtg tggaaaacca agtcatgttt tcagccctca     1680
agctttgctt gcatgatgga tttgtcagac agaaataaag ccaaatgcga tgaccctgga     1740
ccactggaaa atggacacgc cacacttcat ggacaaagta ttgatgggtt ctatgctggt     1800
tcttctataa ggtacagctg tgaggttctc cactacctca gtggaactga gaccgtaact     1860
tgtacaacaa atggcacatg gagtgctcct aaacctcgat gtatcaaagt catcacctgc     1920
caaaaccctc ctgtaccatc atatggttct gtggaaatca aaccccaag tcggacaaac     1980 tcgatcagtc gtgttgggtc acctttcttg aggttgccac ggttacccct cccattagcc     2040
agagcagcca aacctcctcc aaaacctaga tcctcacaac cctctactgt ggacttggct     2100
tctaaagtta aactacctga aggtcattac cgggtagggt ctcgagccat ttacacgtgc     2160
gagtcgagat actacgaact acttggatct caaggcagaa gatgtgactc taatggaaac     2220
tggagtggtc ggcccgctag ctgtattcca gtttgtggac ggtcagactc tcctcgttct     2280
cctttcatct ggaatgggaa ttctacagaa ataggtcagt ggccgtggca ggcaggaatc     2340
```

-continued

```
tctcgatggc ttgcagacca caatatgtgg tttctccagt gtggaggatc cctattgaat    2400
gagaaatgga tcgtcactgc tgcccactgt gtcacctact ctgctactgc tgagataatt    2460
gatcccagtc agtttaaaat ctatctgggc aagtactacc gtgatgacag tagagacgat    2520
gactacgtac aagtaagaga ggctctcgag atccacgtaa atcctaacta cgaccccggc    2580
aatctcaact ttgacatagc cctaattcaa ctgaaaactc ctgttacttt gacaacacga    2640
gtccaaccaa tctgtctgcc tactgacatc acaacaagag aacacttgaa ggagggaaca    2700
ttagcagtgg tgacaggttg gggtttgaat gaaaacaaca catattcaga gatgattcaa    2760
caagctgtgc tacctgttgt tgcagcaagc acctgtgaag aggggtacaa ggaagcagac    2820
ttaccactga cagtaacaga gaacatgttc tgtgcaggtt acaagaaggg acgttatgat    2880
gcctgcagtg gggacagtgg aggaccatta gtgtttgctg atgattcccg taccgaaagg    2940
cggtgggtct tggaagggat tgtcagctgg ggcagtccca gtggatgtgg caaggctaac    3000
cagtatgggg gcttcactaa agttaacgtt tttctatcat ggattaggca gttcatttga    3060
```

<210> SEQ ID NO 12
<211> LENGTH: 1019
<212> TYPE: PRT
<213> ORGANISM: Tachypleus tridentatus
<220> FEATURE:
<223> OTHER INFORMATION: Tachypleus tridentatus factor C

<400> SEQUENCE: 12

```
Met Val Leu Ala Ser Phe Leu Val Ser Gly Leu Val Leu Gly Ile Leu
1               5                   10                  15

Ala Gln Gln Met Arg Pro Val Gln Ser Arg Gly Val Asp Leu Gly Leu
            20                  25                  30

Cys Asp Glu Thr Arg Phe Glu Cys Lys Cys Gly Asp Pro Gly Tyr Val
        35                  40                  45

Phe Asn Val Pro Met Lys Gln Cys Thr Tyr Phe Tyr Arg Trp Arg Pro
    50                  55                  60

Tyr Cys Lys Pro Cys Asp Asp Leu Glu Ala Lys Asp Ile Cys Pro Lys
65                  70                  75                  80

Tyr Lys Arg Cys Gln Glu Cys Lys Ala Gly Leu Asp Ser Cys Val Thr
                85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Thr Cys Arg
        115                 120                 125

Asp Arg Tyr Glu Gly Ala His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Val Ala Arg Ile Ser Cys Leu Pro Asn Gly Gln Trp Ser Ser Phe Pro
            180                 185                 190

Pro Lys Cys Ile Arg Glu Cys Ala Lys Val Ser Ser Pro Glu His Gly
        195                 200                 205

Lys Val Asn Ala Pro Ser Gly Asn Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240
```

```
Cys Gln Gly Asn Gly Gln Trp Ser Gly Gln Ile Pro Gln Cys Lys Lys
                245                 250                 255

Leu Val Phe Cys Pro Asp Leu Asp Pro Val Asn His Ala Glu His Gln
                260                 265                 270

Val Lys Ile Gly Val Glu Gln Lys Tyr Gly Gln Phe Pro Gln Gly Thr
                275                 280                 285

Glu Val Thr Tyr Thr Cys Ser Gly Asn Tyr Phe Leu Met Gly Phe Asn
                290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
                340                 345                 350

Gly Cys Ser Leu Thr Ala Gly Thr Val Trp Gly Thr Ala Ile Tyr His
                355                 360                 365

Glu Leu Ser Ser Val Cys Arg Ala Ala Ile His Ala Gly Lys Leu Pro
                370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                405                 410                 415

Leu Ala Arg Ser Phe Arg Phe Asp Tyr Val Ser Ser Ser Thr Ala Gly
                420                 425                 430

Arg Ser Gly Cys Pro Asp Gly Trp Phe Glu Val Glu Asn Cys Val
                435                 440                 445

Tyr Val Thr Ser Lys Gln Arg Ala Trp Glu Arg Ala Gln Gly Val Cys
                450                 455                 460

Thr Asn Met Ala Ala Arg Leu Ala Val Leu Asp Lys Asp Leu Ile Pro
465                 470                 475                 480

Ser Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Val Trp Glu Leu
                500                 505                 510

Met Asp Arg Ser Asn Val Val Leu Asn Asp Asn Leu Thr Phe Trp Ala
                515                 520                 525

Ser Gly Glu Pro Gly Asn Glu Thr Asn Cys Val Tyr Leu Asp Ile Arg
                530                 535                 540

Asp Gln Leu Gln Pro Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Pro Leu Glu Asn Gly His Ala Thr Leu His Gly Gln
                580                 585                 590

Ser Ile Asp Gly Phe Tyr Ala Gly Ser Ser Ile Arg Tyr Ser Cys Glu
                595                 600                 605

Val Leu His Tyr Leu Ser Gly Thr Glu Thr Val Thr Cys Thr Thr Asn
                610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655
```

```
Ser Arg Thr Asn Ser Ile Ser Arg Val Gly Ser Pro Phe Leu Arg Leu
            660                 665                 670

Pro Arg Leu Pro Leu Pro Leu Ala Arg Ala Ala Lys Pro Pro Lys
        675                 680                 685

Pro Arg Ser Ser Gln Pro Ser Thr Val Asp Leu Ala Ser Lys Val Lys
        690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
            740                 745                 750

Gly Arg Ser Asp Ser Pro Arg Ser Pro Phe Ile Trp Asn Gly Asn Ser
        755                 760                 765

Thr Glu Ile Gly Gln Trp Pro Trp Gln Ala Gly Ile Ser Arg Trp Leu
770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Ser Gln Phe Lys Ile Tyr Leu Gly Lys Tyr
            820                 825                 830

Tyr Arg Asp Asp Ser Arg Asp Asp Tyr Val Gln Val Arg Glu Ala
        835                 840                 845

Leu Glu Ile His Val Asn Pro Asn Tyr Asp Pro Gly Asn Leu Asn Phe
850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu
                885                 890                 895

Lys Glu Gly Thr Leu Ala Val Val Thr Gly Trp Gly Leu Asn Glu Asn
            900                 905                 910

Asn Thr Tyr Ser Glu Met Ile Gln Gln Ala Val Leu Pro Val Val Ala
        915                 920                 925

Ala Ser Thr Cys Glu Glu Gly Tyr Lys Glu Ala Asp Leu Pro Leu Thr
        930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
            980                 985                 990

Pro Ser Gly Cys Gly Lys Ala Asn  Gln Tyr Gly Gly Phe  Thr Lys Val
        995                 1000                1005

Asn Val  Phe Leu Ser Trp Ile  Arg Gln Phe Ile
    1010                    1015

<210> SEQ ID NO 13
<211> LENGTH: 3063
<212> TYPE: DNA
<213> ORGANISM: Limulus polyphemus
<220> FEATURE:
<223> OTHER INFORMATION: Limulus polyphemus factor C

<400> SEQUENCE: 13
```

-continued

```
atggtactag cgtcgttctt ggtgtctggt ttagttctag ggctattagc ccaacaaatg     60
cacccagttc agtccagagg agtagatctg ggcttgtgtg atgacacgag gtttgagtgt    120
aagtgtggag atccaggata cgtgttcaac gtccccgcga agcaatgtac gtacttctat    180
cgatggaggc cttattgtaa accatgtgac aaactggagg ctaaagatgt gtgtcccaag    240
tacaaacgat gtcaagagtg tagggctggt ctcgacagtt gtgtgagttg tccacctaac    300
aaatatggaa cttggtgtag cggtgagtgt cagtgtaaga atgggggtat ttgtgatcag    360
aggacaggag cttgtacatg tcgtgacaga tatgaaggtg tgcattgtga aatccttcaa    420
ggttgtcctc ttcttcaatc ggatccccag gttcaggaag taaaaaatcc accaaatgat    480
ccacaaacta ttgactacag ctgttcacca ggcttcaagc ttaaaggcgt ggcacgtatc    540
acctgtcttc caaatgggca gtggagtagc tttccaccca atgtattcg agaatgttcc     600
atggtttcat ctctagaaca tggcaaagta aactctccta gtgccgatct gatagaagga    660
gctactttaa ggttctcatg tgatagtccc tactacttga ttggtcaaga acattaacc     720
tgccagggca acggtcagtg gagtgggcag ataccacagt gtcagaaatt ggtcttctgc    780
cctgaccttg accctgtaag ccatgctgaa caccaggtta aaattggcct agaacaaaaa    840
tatggtcaat ttcctcaagg cactgaagta acctatcgt gtactggtaa ttacttcttg      900
atgggtttgg acaccttaaa atgtaaccct gatgggtcct ggtcgggaac acagccgtcc    960
tgtgttaaag tggcagacag agaggtcaac tgtgacagta aagctgtgga cttcttggat   1020
gatgttggcg aacctgtcag gatccactgt cctgctggct gttccttaac tgctggtact   1080
gtatggggta cagccatata tcacgaactt tcctcagtat gtcgtgcagc tattcatgct   1140
ggcaaggttc caaactctgg aggtgcagtg catgtagtga acaacggtcc gtactcagac   1200
tttctggcta gtgatctgaa tgggataaaa tcagacgagt tgaagtctct tgctcagagt   1260
ttccgattcg attatgtcag ttcatcaaca gcagggagaa agtcaggatg tcctgatgga   1320
tggttcgaga ttgaggagaa ctgtgtgtac gttacatcga aacagagagc ctgggaaaga   1380
gctcaaggtg tatgtaccaa tatggccgct cgtcttgctg tgttagacaa agatgtaatt   1440
ccaagttcct tgactgagac tctacgaggg aaagggttag caacgacgtg gattggacta   1500
cacagattag atgctgataa tcactttatt tgggagctaa tggatcgcag tagtgttgct   1560
ttgaatgaca gcctaacatt ctgggctcct ggagaacctg ggaatgaaac taactgtgta   1620
tatctggata tccaagatca gctacagcca gtgtggaaaa ccaagtcttg ttttcaaccc   1680
tcaagttttg tttgtatgat ggatttgtca gacaagaaca aagccaaatg caaagaccct   1740
ggaccttggg aaaacggaca cgccaagctt catggtcaaa gtattgatgg attttatgct   1800
gggtcttctg taagatacag ctgcgaggtc ctccactacc tcagtggaac tgagacagta   1860
tcttgtacat caaatggcac gtggagtgcc cctaaacctc gatgtattaa agtcatcacc   1920
tgccaaaccc ctcctgtacc atcctatggt tctgtggaca tcaaaccccc aagtagaaca   1980
aactcaatca gtcgtgttgg gtcgccattc ttgaggttgc cacggttacc cctccctta   2040
gccagagcag ccggacctcc tccaaaacct agatccgcac caccctctac tgtggacctg   2100
tcttccaagg tcaaactgcc tgaaggtcat taccgggtgg ggtctcaagc catttacacg   2160
tgcgagtcaa gatactacga actgcttgga tctcaaggta agatgcgca ctctaatgga    2220
aagtggagtg tcgaccagc aagctgtata ccagtttgtg acggtcaga ctctccccgt      2280
tctccttca tcgtcaatgg aaattccacc gaaataggtc agtggccgtg gcaggcagga   2340
atctccagat ggcttgcaga tcataatatg tggtttcttc agtgtggagg agctctactg   2400
```

-continued

```
aatgagaaat ggatcattac tgcagcccac tgtgtcacct actctgctac tgccgagatc    2460
attgacccaa gtcagtttaa attctacctg gcaaatact atcgagatga cagtaaggat    2520
gatgactacg tacaagtaag agaggctatc gagatccatg tgaatcctaa ctacgatcct    2580
ggaaatctca actttgacat agccctgatt caactgaaga cttctgttgc tctgaccaca    2640
cgagtgcaac caatatgtct gcctactgat ctcactacaa gagaaaacct gaaagaggga    2700
gcgttagcgg tggtgacagg atggggtttg aatgaaaaca acacatattc agagatgatt    2760
cagcaagccg ttctgcctgt tgttgcagca agcacctgtg aacaaggata tcaggactcg    2820
ggcttgccac tgacagtgac agagaacatg ttctgtgcag gttacaagca ggggcgctat    2880
gatgcctgca gtggagacag tggaggacca ttagtgtttg ctgatgattc ccgcaccgat    2940
aggcggtggg tcctggaagg gatcgtcagc tggggcagcc ccaatggatg tggcaagtct    3000
aaccagtatg ggggcttcac taaagttaac gttttctat cgtggattcg gcagttcatt    3060
tga                                                                  3063
```

<210> SEQ ID NO 14
<211> LENGTH: 1020
<212> TYPE: PRT
<213> ORGANISM: Limulus polyphemus
<220> FEATURE:
<223> OTHER INFORMATION: Limulus polyphemus factor C

<400> SEQUENCE: 14

```
Met Val Leu Ala Ser Phe Leu Val Ser Gly Leu Val Leu Gly Leu Leu
1               5                   10                  15

Ala Gln Gln Met His Pro Val Gln Ser Arg Gly Val Asp Leu Gly Leu
            20                  25                  30

Cys Asp Asp Thr Arg Phe Glu Cys Lys Cys Gly Asp Pro Gly Tyr Val
        35                  40                  45

Phe Asn Val Pro Ala Lys Gln Cys Thr Tyr Phe Tyr Arg Trp Arg Pro
    50                  55                  60

Tyr Cys Lys Pro Cys Asp Lys Leu Glu Ala Lys Asp Val Cys Pro Lys
65                  70                  75                  80

Tyr Lys Arg Cys Gln Glu Cys Arg Ala Gly Leu Asp Ser Cys Val Ser
                85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Thr Cys Arg
        115                 120                 125

Asp Arg Tyr Glu Gly Val His Cys Glu Ile Leu Gln Gly Cys Pro Leu
    130                 135                 140

Leu Gln Ser Asp Pro Gln Val Gln Glu Val Lys Asn Pro Pro Asn Asp
145                 150                 155                 160

Pro Gln Thr Ile Asp Tyr Ser Cys Ser Pro Gly Phe Lys Leu Lys Gly
                165                 170                 175

Val Ala Arg Ile Thr Cys Leu Pro Asn Gly Gln Trp Ser Ser Phe Pro
            180                 185                 190

Pro Lys Cys Ile Arg Glu Cys Ser Met Val Ser Ser Leu Glu His Gly
        195                 200                 205

Lys Val Asn Ser Pro Ser Ala Asp Leu Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240
```

```
Cys Gln Gly Asn Gly Gln Trp Ser Gly Gln Ile Pro Gln Cys Gln Lys
                    245                 250                 255

Leu Val Phe Cys Pro Asp Leu Asp Pro Val Ser His Ala Glu His Gln
            260                 265                 270

Val Lys Ile Gly Leu Glu Gln Lys Tyr Gly Gln Phe Pro Gln Gly Thr
        275                 280                 285

Glu Val Thr Tyr Thr Cys Thr Gly Asn Tyr Phe Leu Met Gly Leu Asp
    290                 295                 300

Thr Leu Lys Cys Asn Pro Asp Gly Ser Trp Ser Gly Thr Gln Pro Ser
305                 310                 315                 320

Cys Val Lys Val Ala Asp Arg Glu Val Asn Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Val Pro
    370                 375                 380

Asn Ser Gly Gly Ala Val His Val Val Asn Asn Gly Pro Tyr Ser Asp
385                 390                 395                 400

Phe Leu Ala Ser Asp Leu Asn Gly Ile Lys Ser Asp Glu Leu Lys Ser
                405                 410                 415

Leu Ala Gln Ser Phe Arg Phe Asp Tyr Val Ser Ser Thr Ala Gly
            420                 425                 430

Arg Lys Ser Gly Cys Pro Asp Gly Trp Phe Glu Ile Glu Glu Asn Cys
        435                 440                 445

Val Tyr Val Thr Ser Lys Gln Arg Ala Trp Glu Arg Ala Gln Gly Val
    450                 455                 460

Cys Thr Asn Met Ala Ala Arg Leu Ala Val Leu Asp Lys Asp Val Ile
465                 470                 475                 480

Pro Ser Ser Leu Thr Glu Thr Leu Arg Gly Lys Gly Leu Ala Thr Thr
                485                 490                 495

Trp Ile Gly Leu His Arg Leu Asp Ala Asp Asn His Phe Ile Trp Glu
            500                 505                 510

Leu Met Asp Arg Ser Ser Val Ala Leu Asn Asp Ser Leu Thr Phe Trp
        515                 520                 525

Ala Pro Gly Glu Pro Gly Asn Glu Thr Asn Cys Val Tyr Leu Asp Ile
    530                 535                 540

Gln Asp Gln Leu Gln Pro Val Trp Lys Thr Lys Ser Cys Phe Gln Pro
545                 550                 555                 560

Ser Ser Phe Val Cys Met Met Asp Leu Ser Asp Lys Asn Lys Ala Lys
                565                 570                 575

Cys Lys Asp Pro Gly Pro Leu Glu Asn Gly His Ala Lys Leu His Gly
            580                 585                 590

Gln Ser Ile Asp Gly Phe Tyr Ala Gly Ser Ser Val Arg Tyr Ser Cys
        595                 600                 605

Glu Val Leu His Tyr Leu Ser Gly Thr Glu Thr Val Ser Cys Thr Ser
    610                 615                 620

Asn Gly Thr Trp Ser Ala Pro Lys Pro Arg Cys Ile Lys Val Ile Thr
625                 630                 635                 640

Cys Gln Thr Pro Pro Val Pro Ser Tyr Gly Ser Val Asp Ile Lys Pro
                645                 650                 655
```

```
Pro Ser Arg Thr Asn Ser Ile Ser Arg Val Gly Ser Pro Phe Leu Arg
            660                 665                 670

Leu Pro Arg Leu Pro Leu Pro Leu Ala Arg Ala Ala Gly Pro Pro
        675                 680                 685

Lys Pro Arg Ser Ala Pro Pro Ser Thr Val Asp Leu Ser Ser Lys Val
        690                 695                 700

Lys Leu Pro Glu Gly His Tyr Arg Val Gly Ser Gln Ala Ile Tyr Thr
705                 710                 715                 720

Cys Glu Ser Arg Tyr Tyr Glu Leu Leu Gly Ser Gln Gly Arg Arg Cys
                725                 730                 735

Asp Ser Asn Gly Lys Trp Ser Gly Arg Pro Ala Ser Cys Ile Pro Val
            740                 745                 750

Cys Gly Arg Ser Asp Ser Pro Arg Ser Pro Phe Ile Val Asn Gly Asn
        755                 760                 765

Ser Thr Glu Ile Gly Gln Trp Pro Trp Gln Ala Gly Ile Ser Arg Trp
        770                 775                 780

Leu Ala Asp His Asn Met Trp Phe Leu Gln Cys Gly Gly Ala Leu Leu
785                 790                 795                 800

Asn Glu Lys Trp Ile Ile Thr Ala Ala His Cys Val Thr Tyr Ser Ala
                805                 810                 815

Thr Ala Glu Ile Ile Asp Pro Ser Gln Phe Lys Phe Tyr Leu Gly Lys
            820                 825                 830

Tyr Tyr Arg Asp Asp Ser Lys Asp Asp Tyr Val Gln Val Arg Glu
        835                 840                 845

Ala Ile Glu Ile His Val Asn Pro Asn Tyr Asp Pro Gly Asn Leu Asn
850                 855                 860

Phe Asp Ile Ala Leu Ile Gln Leu Lys Thr Ser Val Ala Leu Thr Thr
865                 870                 875                 880

Arg Val Gln Pro Ile Cys Leu Pro Thr Asp Leu Thr Thr Arg Glu Asn
                885                 890                 895

Leu Lys Glu Gly Ala Leu Ala Val Val Thr Gly Trp Gly Leu Asn Glu
            900                 905                 910

Asn Asn Thr Tyr Ser Glu Met Ile Gln Gln Ala Val Leu Pro Val Val
        915                 920                 925

Ala Ala Ser Thr Cys Glu Gln Gly Tyr Gln Asp Ser Gly Leu Pro Leu
        930                 935                 940

Thr Val Thr Glu Asn Met Phe Cys Ala Gly Tyr Lys Gln Gly Arg Tyr
945                 950                 955                 960

Asp Ala Cys Ser Gly Asp Ser Gly Gly Pro Leu Val Phe Ala Asp Asp
                965                 970                 975

Ser Arg Thr Asp Arg Arg Trp Val Leu Glu Gly Ile Val Ser Trp Gly
            980                 985                 990

Ser Pro Asn Gly Cys Gly Lys Ser  Asn Gln Tyr Gly Gly Phe Thr Lys
        995                 1000                1005

Val Asn Val Phe Leu Ser Trp  Ile Arg Gln Phe Ile
    1010                1015                1020

<210> SEQ ID NO 15
<211> LENGTH: 3060
<212> TYPE: DNA
<213> ORGANISM: Carcinoscorpius rotundicauda
<220> FEATURE:
<223> OTHER INFORMATION: Carcinoscorpius rotundicauda factor C

<400> SEQUENCE: 15
```

-continued

```
atggtcttag cgtcgttttt ggtgtctggt ttagttctag ggctactagc ccaaaaaatg    60
cgcccagttc agtccaaagg agtagatcta ggcttgtgtg atgaaacgag gttcgagtgt   120
aagtgtggcg atccaggcta tgtgttcaac attccagtga aacaatgtac atacttttat   180
cgatggaggc cgtattgtaa accatgtgat gacctggagg ctaaggatat ttgtccaaag   240
tacaaacgat gtcaagagtg taaggctggt cttgatagtt gtgttacttg tccacctaac   300
aaatatggta cttggtgtag cggtgaatgt cagtgtaaga atggaggtat ctgtgaccag   360
aggacaggag cttgtgcatg tcgtgacaga tatgaagggg tgcactgtga aattctcaaa   420
ggttgtcctc ttcttccatc ggattctcag gttcaggaag tcagaaatcc accagataat   480
ccccaaacta ttgactacag ctgttcacca gggttcaagc ttaagggtat ggcacgaatt   540
agctgtctcc caaatggaca gtggagtaac tttccaccca atgtattcg agaatgtgcc    600 atggtttcat ctccagaaca tgggaaagtg aatgctctta gtggtgatat gatagaaggg   660
gctactttac ggttctcatg tgatagtccc tactacttga ttggtcaaga acattaacc    720 tgtcaggta atggtcagtg gaatggacag ataccacaat gtaagaactt ggtcttctgt    780
cctgacctgg atcctgtaaa ccatgctgaa cacaaggtta aaattggtgt ggaacaaaaa   840
tatggtcagt ttcctcaagg cactgaagtg acctatacgt gttcgggtaa ctacttcttg   900
atggggtttg acaccttaaa atgtaaccct gatgggtctt ggtcaggatc acagccatcc   960
tgtgttaaag tggcagacag agaggtcgac tgtgacagta aagctgtaga cttcttggat  1020
gatgttggtg aacctgtcag gatccactgt cctgctggct gttctttgac agctggtact  1080 gtgtgggta cagccatata ccatgaactt tcctcagtgt gtcgtgcagc catccatgct   1140
ggcaagcttc caaactctgg aggagcggtg catgttgtga acaatggccc ctactcggac  1200
tttctgggta gtgacctgaa tgggataaaa tcggaagagt gaagtctct tgcccggagt   1260 ttccgattcg attatgtccg ttcctccaca gcaggtaaat caggatgtcc tgatggatgg  1320
tttgaggtag acgagaactg tgtgtacgtt acatcaaaac agagagcctg ggaaagagct  1380
caaggtgtgt gtaccaatat ggctgctcgt cttgctgtgc tggacaaaga tgtaattcca  1440
aattcgttga ctgagactct acgagggaaa gggttaacaa ccacgtggat aggattgcac  1500
agactagatg ctgagaagcc cttttatttgg gagttaatgg atcgtagtaa tgtggttctg  1560
aatgataacc taacattctg ggcctctggc gaacctggaa atgaaactaa ctgtgtatat  1620
atggacatcc aagatcagtt gcagtctgtg tggaaaacca agtcatgttt tcagccctca  1680
agttttgctt gcatgatgga tctgtcagac agaaatgaag ccaaatgcga tgatcctgga  1740
tcactggaaa atggacacgc cacacttcat ggacaaagta ttgatgggtt ctatgctggt  1800
tcttctataa ggtacagctg tgaggttctc cactacctca gtggaactga accgtaact   1860 tgtacaacaa atggcacatg gagtgctcct aaacctcgat gtatcaaagt catcacctgc  1920
caaaaccccc ctgtaccatc atatggttct gtggaaatca acccccaag tcggacaaac  1980 tcgataagtc gtgttgggtc acctttcttg aggttgccac ggttacccct cccattagct  2040
agagcagcca aacctcctcc aaaacctaga tcctcacaac cctctactgt ggacttggct  2100
tctaaagtta aactacctga aggtcattac cgggtagggt ctcgagccat ctacacgtgc  2160
gagtcgagat actacgaact acttggatct caaggcagaa gatgtgactc taatggaaac  2220
tggagtggtc ggccagcgag ctgtattcca gtttgtggac ggtcagactc tcctcgttct  2280 cctttttatct ggaatgggaa ttctacagaa ataggtcagt ggccgtggca ggcaggaatc  2340
tctagatggc ttgcagacca caatatgtgg tttctccagt gtggaggatc tctattgaat  2400
```

```
gagaaatgga tcgtcactgc tgcccactgt gtcacctact ctgctactgc tgagattatt   2460
gaccccaatc agtttaaaat gtatctgggc aagtactacc gtgatgacag tagagacgat   2520
gactatgtac aagtaagaga ggctcttgag atccacgtga atcctaacta cgaccccggc   2580
aatctcaact ttgacatagc cctaattcaa ctgaaaactc tgttactttt gacaacacga   2640
gtccaaccaa tctgtctgcc tactgacatc acaacaagag aacacttgaa ggagggaaca   2700
ttagcagtgg tgacaggttg gggtttgaat gaaaacaaca cctattcaga gacgattcaa   2760
caagctgtgc tacctgttgt tgcagccagc acctgtgaag aggggtacaa ggaagcagac   2820
ttaccactga cagtaacaga gaacatgttc tgtgcaggtt acaagaaggg acgttatgat   2880
gcctgcagtg gggacagtgg aggaccttta gtgtttgctg atgattcccg taccgaaagg   2940
cggtgggtct tggaagggat tgtcagctgg ggcagtccca gtggatgtgg caaggcgaac   3000
cagtacgggg gcttcactaa agttaacgtt ttcctgtcat ggattaggca gttcatttga   3060
```

<210> SEQ ID NO 16  
<211> LENGTH: 1019  
<212> TYPE: PRT  
<213> ORGANISM: Carcinoscorpius rotundicauda  
<220> FEATURE:  
<223> OTHER INFORMATION: Carcinoscorpius rotundicauda factor C

<400> SEQUENCE: 16

```
Met Val Leu Ala Ser Phe Leu Val Ser Gly Leu Val Leu Gly Leu Leu
1               5                   10                  15

Ala Gln Lys Met Arg Pro Val Gln Ser Lys Gly Val Asp Leu Gly Leu
            20                  25                  30

Cys Asp Glu Thr Arg Phe Glu Cys Lys Cys Gly Asp Pro Gly Tyr Val
        35                  40                  45

Phe Asn Ile Pro Val Lys Gln Cys Thr Tyr Phe Tyr Arg Trp Arg Pro
    50                  55                  60

Tyr Cys Lys Pro Cys Asp Asp Leu Glu Ala Lys Asp Ile Cys Pro Lys
65                  70                  75                  80

Tyr Lys Arg Cys Gln Glu Cys Lys Ala Gly Leu Asp Ser Cys Val Thr
                85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Ala Cys Arg
        115                 120                 125

Asp Arg Tyr Glu Gly Val His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Met Ala Arg Ile Ser Cys Leu Pro Asn Gly Gln Trp Ser Asn Phe Pro
            180                 185                 190

Pro Lys Cys Ile Arg Glu Cys Ala Met Val Ser Ser Pro Glu His Gly
        195                 200                 205

Lys Val Asn Ala Leu Ser Gly Asp Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Asn Gly Gln Ile Pro Gln Cys Lys Asn
```

245                 250                 255
Leu Val Phe Cys Pro Asp Leu Asp Pro Val Asn His Ala Glu His Lys
                260                 265                 270

Val Lys Ile Gly Val Glu Gln Lys Tyr Gly Gln Phe Pro Gln Gly Thr
            275                 280                 285

Glu Val Thr Tyr Thr Cys Ser Gly Asn Tyr Phe Leu Met Gly Phe Asp
        290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
            340                 345                 350

Gly Cys Ser Leu Thr Ala Gly Thr Val Trp Gly Thr Ala Ile Tyr His
        355                 360                 365

Glu Leu Ser Ser Val Cys Arg Ala Ala Ile His Ala Gly Lys Leu Pro
    370                 375                 380

Asn Ser Gly Gly Ala Val His Val Val Asn Asn Gly Pro Tyr Ser Asp
385                 390                 395                 400

Phe Leu Gly Ser Asp Leu Asn Gly Ile Lys Ser Glu Glu Leu Lys Ser
                405                 410                 415

Leu Ala Arg Ser Phe Arg Phe Asp Tyr Val Arg Ser Ser Thr Ala Gly
            420                 425                 430

Lys Ser Gly Cys Pro Asp Gly Trp Phe Glu Val Asp Glu Asn Cys Val
        435                 440                 445

Tyr Val Thr Ser Lys Gln Arg Ala Trp Glu Arg Ala Gln Gly Val Cys
    450                 455                 460

Thr Asn Met Ala Ala Arg Leu Ala Val Leu Asp Lys Asp Val Ile Pro
465                 470                 475                 480

Asn Ser Leu Thr Glu Thr Leu Arg Gly Lys Gly Leu Thr Thr Thr Trp
                485                 490                 495

Ile Gly Leu His Arg Leu Asp Ala Glu Lys Pro Phe Ile Trp Glu Leu
            500                 505                 510

Met Asp Arg Ser Asn Val Val Leu Asn Asp Asn Leu Thr Phe Trp Ala
        515                 520                 525

Ser Gly Glu Pro Gly Asn Glu Thr Asn Cys Val Tyr Met Asp Ile Gln
    530                 535                 540

Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
                565                 570                 575

Asp Asp Pro Gly Ser Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
        595                 600                 605

Val Leu His Tyr Leu Ser Gly Thr Glu Thr Val Thr Cys Thr Thr Asn
    610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
                645                 650                 655

Ser Arg Thr Asn Ser Ile Ser Arg Val Gly Ser Pro Phe Leu Arg Leu
            660                 665                 670

```
Pro Arg Leu Pro Leu Pro Leu Ala Arg Ala Ala Lys Pro Pro Lys
        675                 680                 685

Pro Arg Ser Ser Gln Pro Ser Thr Val Asp Leu Ala Ser Lys Val Lys
690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
                725                 730                 735

Ser Asn Gly Asn Trp Ser Gly Arg Pro Ala Ser Cys Ile Pro Val Cys
            740                 745                 750

Gly Arg Ser Asp Ser Pro Arg Ser Pro Phe Ile Trp Asn Gly Asn Ser
        755                 760                 765

Thr Glu Ile Gly Gln Trp Pro Trp Gln Ala Gly Ile Ser Arg Trp Leu
770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
                805                 810                 815

Ala Glu Ile Ile Asp Pro Asn Gln Phe Lys Met Tyr Leu Gly Lys Tyr
            820                 825                 830

Tyr Arg Asp Asp Ser Arg Asp Asp Tyr Val Gln Val Arg Glu Ala
        835                 840                 845

Leu Glu Ile His Val Asn Pro Asn Tyr Asp Pro Gly Asn Leu Asn Phe
850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu
                885                 890                 895

Lys Glu Gly Thr Leu Ala Val Val Thr Gly Trp Gly Leu Asn Glu Asn
            900                 905                 910

Asn Thr Tyr Ser Glu Thr Ile Gln Gln Ala Val Leu Pro Val Val Ala
        915                 920                 925

Ala Ser Thr Cys Glu Glu Gly Tyr Lys Glu Ala Asp Leu Pro Leu Thr
930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
            980                 985                 990

Pro Ser Gly Cys Gly Lys Ala Asn Gln Tyr Gly Gly Phe Thr Lys Val
        995                 1000                1005

Asn Val Phe Leu Ser Trp Ile Arg Gln Phe Ile
    1010                1015
```

<210> SEQ ID NO 17
<211> LENGTH: 1128
<212> TYPE: DNA
<213> ORGANISM: Tachypleus tridentatus
<220> FEATURE:
<223> OTHER INFORMATION: Tachypleus tridentatus pro-clotting enzyme

<400> SEQUENCE: 17
atgttggtga ataacgtgtt ttcactactg tgtttcccac tcttgatgtc tgtggttaga     60

```
tgcagtactc tcagcagaca gcgtagacag tttgttttcc ctgacgagga agaactttgc    120
tcaaaccgat ttactgaaga aggaacatgc aaaaatgtct tggattgtag aatactttta    180
caaaaaaatg attataattt actcaaagaa tcaatatgcg gctttgaagg cataacaccc    240
aaagtttgtt gtccgaaatc aagccatgta atttcaagta cacaggcacc tccagaaacc    300
actacgactg aacgcccacc aaaacagata ccacccaatc ttcctgaagt gtgtggaatt    360
cacaatacta caactaccag gattattgga ggtcgggaag cacctattgg agcctggccg    420
tggatgactg ctgtctacat aaaacaagga ggaatcagaa gtgttcagtg tggtggcgca    480
cttgtcacta acaggcacgt gattacagct tcgcactgtg ttgtaaacag tgcaggaaca    540
gatgtgatgc cagctgatgt attctcggtt cgtctgggtg aacacaattt atacagtacc    600
gatgacgatt cgaatccaat agattttgca gttacgtcgg tgaaacatca cgaacacttt    660
gtactcgcga cgtatttgaa tgacatcgca attctaacgt taaatgacac agttacgttt    720
acagacagaa ttcgacccat ttgtctacct tatcgtaagt tgagatacga tgatctagca    780
atgagaaaac cgtttatcac tggatgggga acaacagcat ttaacggccc atctagtgca    840
gtgttgagag aagtacagtt accaatatgg gaacacgagg cctgtagaca ggcctacgag    900
aaggatttaa atattacaaa cgtgtatatg tgtgctggct ttgcagatgg cgggaaggat    960
gcttgccagg gtgattctgg aggtccaatg atgttgcctg ttaaaaccgg agagttttat    1020
ctcattggaa ttgtgtcttt cggaaagaaa tgcgcattgc ctggatttcc tggggtttac    1080
acaaaagtga cagagttttt agattggatt gcagaacata tggtgtag                 1128
```

<210> SEQ ID NO 18
<211> LENGTH: 375
<212> TYPE: PRT
<213> ORGANISM: Tachypleus tridentatus
<220> FEATURE:
<223> OTHER INFORMATION: Tachypleus tridentatus pro-clotting enzyme

<400> SEQUENCE: 18

```
Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Gln Phe Val
            20                  25                  30

Phe Pro Asp Glu Glu Leu Cys Ser Asn Arg Phe Thr Glu Glu Gly
        35                  40                  45

Thr Cys Lys Asn Val Leu Asp Cys Arg Ile Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Ser Ser His Val Ile Ser Ser Thr Gln Ala
                85                  90                  95

Pro Pro Glu Thr Thr Thr Thr Glu Arg Pro Pro Lys Gln Ile Pro Pro
            100                 105                 110

Asn Leu Pro Glu Val Cys Gly Ile His Asn Thr Thr Thr Thr Arg Ile
        115                 120                 125

Ile Gly Gly Arg Glu Ala Pro Ile Gly Ala Trp Pro Trp Met Thr Ala
    130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175
```

```
Ser Ala Gly Thr Asp Val Met Pro Ala Asp Val Phe Ser Val Arg Leu
            180                 185                 190

Gly Glu His Asn Leu Tyr Ser Thr Asp Asp Ser Asn Pro Ile Asp
        195                 200                 205

Phe Ala Val Thr Ser Val Lys His His Glu His Phe Val Leu Ala Thr
    210                 215                 220

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
                245                 250                 255

Asp Asp Leu Ala Met Arg Lys Pro Phe Ile Thr Gly Trp Gly Thr Thr
            260                 265                 270

Ala Phe Asn Gly Pro Ser Ser Ala Val Leu Arg Glu Val Gln Leu Pro
        275                 280                 285

Ile Trp Glu His Glu Ala Cys Arg Gln Ala Tyr Glu Lys Asp Leu Asn
    290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
                325                 330                 335

Gly Glu Phe Tyr Leu Ile Gly Ile Val Ser Phe Gly Lys Lys Cys Ala
            340                 345                 350

Leu Pro Gly Phe Pro Gly Val Tyr Thr Lys Val Thr Glu Phe Leu Asp
        355                 360                 365

Trp Ile Ala Glu His Met Val
    370                 375

<210> SEQ ID NO 19
<211> LENGTH: 1128
<212> TYPE: DNA
<213> ORGANISM: Limulus polyphemus
<220> FEATURE:
<223> OTHER INFORMATION: Limulus polyphemus pro-clotting enzyme

<400> SEQUENCE: 19
atgttggtga ataacatgtt ttcattgctg tgtttcccac tcctgatgtc tatgtttagc    60
tgcagtagtc tcggcagaca gcgtagacag tttgttttcc ccgatgatga agaatcatgc   120
tcaaaccgat ttactaacga tggaatatgt aaagatgttt tgaattgtag agatcttta   180 caaaaaatg attataattt actgaaagaa tcaatatgcg gttttgaagg cataacaccc   240
aaagtttgtt gtccgaaaca aagtattgta atccaataa cagaagcacc tccaaaaacc   300
actacaactg aacgaccgcc aatacggata ccatccaatc ttcctaaaca gtgtggaaat   360
cgtaatatta caactaccag gattattgga gggcaggaag caacacctgg agcctggccc   420
tggatggctg ctgtctatat caaacaagga ggaatcagaa gtgttcagtg tggaggtgcg   480
cttgtcacca acaggcacgt gattacagca tcgcactgtg ttgtaaacag tttaggaaca   540
gatgtgatgc gagctgacgt attctcggtt cgcctaggtg aacacaattt atatagcacc   600
aatgacagtt cagatccaat tgattttgca gttacgtcag tgaaacatca tgaaaacttt   660
gtgctcgcga cgtatttgaa tgatatcgca attctgaagt taacgacac tgttacgttt   720 acgcacaaaa ttaaccaat ttgtctacct tatgaaagct taggtatga ggatctagca   780 atgagaaacc catttgtcgc cggatgggga acaacagcat taatggccc atctagtgca   840 gtattacgag aagtgcagtt accaatatgg ggacacgagc cctgcaggca ggcctacgag   900
```

```
aaggatttaa atattacaaa cgtgtatatg tgtgctgggt atgcagatgg cggtaaagat    960
gcttgccagg gtgattctgg aggtccaatg atgttgcctg ataaaagcgg gaacttttat   1020
ctcgttggaa ttgtgtcttt cggaaagaaa tgcgcgttgc ctggatttcc tggggtttac   1080
acaaaagtga ccgaattttt agattggatt gcagtaaata tggtgtag               1128
```

<210> SEQ ID NO 20
<211> LENGTH: 375
<212> TYPE: PRT
<213> ORGANISM: Limulus polyphemus
<220> FEATURE:
<223> OTHER INFORMATION: Limulus polyphemus pro-clotting enzyme

<400> SEQUENCE: 20

```
Met Leu Val Asn Asn Met Phe Ser Leu Leu Cys Phe Pro Leu Leu Met
1               5                   10                  15

Ser Met Phe Ser Cys Ser Ser Leu Gly Arg Gln Arg Arg Gln Phe Val
            20                  25                  30

Phe Pro Asp Asp Glu Glu Ser Cys Ser Asn Arg Phe Thr Asn Asp Gly
        35                  40                  45

Ile Cys Lys Asp Val Leu Asn Cys Arg Asp Leu Leu Gln Lys Asn Asp
    50                  55                  60

Tyr Asn Leu Leu Lys Glu Ser Ile Cys Gly Phe Glu Gly Ile Thr Pro
65                  70                  75                  80

Lys Val Cys Cys Pro Lys Gln Ser Ile Val Asn Pro Ile Thr Glu Ala
                85                  90                  95

Pro Pro Lys Thr Thr Thr Thr Glu Arg Pro Pro Ile Arg Ile Pro Ser
            100                 105                 110

Asn Leu Pro Lys Gln Cys Gly Asn Arg Asn Ile Thr Thr Thr Arg Ile
        115                 120                 125

Ile Gly Gly Gln Glu Ala Thr Pro Gly Ala Trp Pro Trp Met Ala Ala
    130                 135                 140

Val Tyr Ile Lys Gln Gly Gly Ile Arg Ser Val Gln Cys Gly Gly Ala
145                 150                 155                 160

Leu Val Thr Asn Arg His Val Ile Thr Ala Ser His Cys Val Val Asn
                165                 170                 175

Ser Leu Gly Thr Asp Val Met Arg Ala Asp Val Phe Ser Val Arg Leu
            180                 185                 190

Gly Glu His Asn Leu Tyr Ser Thr Asn Asp Ser Ser Asp Pro Ile Asp
        195                 200                 205

Phe Ala Val Thr Ser Val Lys His His Glu Asn Phe Val Leu Ala Thr
    210                 215                 220

Tyr Leu Asn Asp Ile Ala Ile Leu Lys Leu Asn Asp Thr Val Thr Phe
225                 230                 235                 240

Thr His Lys Ile Lys Pro Ile Cys Leu Pro Tyr Glu Ser Leu Arg Tyr
                245                 250                 255

Glu Asp Leu Ala Met Arg Asn Pro Phe Val Ala Gly Trp Gly Thr Thr
            260                 265                 270

Ala Phe Asn Gly Pro Ser Ser Ala Val Leu Arg Glu Val Gln Leu Pro
        275                 280                 285

Ile Trp Gly His Glu Pro Cys Arg Gln Ala Tyr Glu Lys Asp Leu Asn
    290                 295                 300

Ile Thr Asn Val Tyr Met Cys Ala Gly Tyr Ala Asp Gly Gly Lys Asp
305                 310                 315                 320

Ala Cys Gln Gly Asp Ser Gly Gly Pro Met Met Leu Pro Asp Lys Ser
```

```
            325                 330                 335
Gly Asn Phe Tyr Leu Val Gly Ile Val Ser Phe Gly Lys Lys Cys Ala
            340                 345                 350

Leu Pro Gly Phe Pro Gly Val Tyr Thr Lys Val Thr Glu Phe Leu Asp
            355                 360                 365

Trp Ile Ala Val Asn Met Val
        370                 375
```

<210> SEQ ID NO 21
<211> LENGTH: 27
<212> TYPE: DNA
<213> ORGANISM: Artificial Sequence
<220> FEATURE:
<223> OTHER INFORMATION: designed primer (primer 1)

<400> SEQUENCE: 21
gggaccggta gaggagtaga tctgggc                                        27

<210> SEQ ID NO 22
<211> LENGTH: 30
<212> TYPE: DNA
<213> ORGANISM: Artificial Sequence
<220> FEATURE:
<223> OTHER INFORMATION: designed primer (primer 2)

<400> SEQUENCE: 22
gggctcgagt cattaaatga actgcctaat                                     30

<210> SEQ ID NO 23
<211> LENGTH: 39
<212> TYPE: DNA
<213> ORGANISM: Artificial Sequence
<220> FEATURE:
<223> OTHER INFORMATION: designed primer (primer 3)

<400> SEQUENCE: 23
ggggaattca agcttgccac catggtctta gcgtcgttt                           39

<210> SEQ ID NO 24
<211> LENGTH: 49
<212> TYPE: DNA
<213> ORGANISM: Artificial Sequence
<220> FEATURE:
<223> OTHER INFORMATION: designed primer (primer 4)

<400> SEQUENCE: 24
gccctcgatg tgatggtgat ggtggtggga ctgaactgga cgcatttgt                49

<210> SEQ ID NO 25
<211> LENGTH: 28
<212> TYPE: DNA
<213> ORGANISM: Artificial Sequence
<220> FEATURE:
<223> OTHER INFORMATION: designed primer (primer 5)

<400> SEQUENCE: 25
agaagaggag tagatctggg cttgtgtg                                       28

<210> SEQ ID NO 26
<211> LENGTH: 30
<212> TYPE: DNA
<213> ORGANISM: Artificial Sequence
<220> FEATURE:
<223> OTHER INFORMATION: designed primer (primer 6)

<400> SEQUENCE: 26
gggaccggtc accaccatca ccatcacatc                              30

<210> SEQ ID NO 27
<211> LENGTH: 30
<212> TYPE: DNA
<213> ORGANISM: Artificial Sequence
<220> FEATURE:
<223> OTHER INFORMATION: designed primer (primer 7)

<400> SEQUENCE: 27
tctagattat caaatgaact gcctaatcca                              30

<210> SEQ ID NO 28
<211> LENGTH: 18
<212> TYPE: DNA
<213> ORGANISM: Artificial Sequence
<220> FEATURE:
<223> OTHER INFORMATION: BGH reverse primer

<400> SEQUENCE: 28
tagaaggcac agtcgagg                                           18

<210> SEQ ID NO 29
<211> LENGTH: 24
<212> TYPE: DNA
<213> ORGANISM: Artificial Sequence
<220> FEATURE:
<223> OTHER INFORMATION: designed primer (primer 8)

<400> SEQUENCE: 29
agcctctgct aaccatgttc atgc                                    24

<210> SEQ ID NO 30
<211> LENGTH: 27
<212> TYPE: DNA
<213> ORGANISM: Artificial Sequence
<220> FEATURE:
<223> OTHER INFORMATION: designed primer (primer 9)

<400> SEQUENCE: 30
gggaccggtg tggggtcct cttcccc                                  27

<210> SEQ ID NO 31
<211> LENGTH: 30
<212> TYPE: DNA
<213> ORGANISM: Artificial Sequence
<220> FEATURE:
<223> OTHER INFORMATION: designed primer (primer 10)

<400> SEQUENCE: 31
gggctcgagt tagttagtga cggcatgatc                              30

<210> SEQ ID NO 32
<211> LENGTH: 35
<212> TYPE: DNA
<213> ORGANISM: Artificial Sequence
<220> FEATURE:
<223> OTHER INFORMATION: designed primer (primer 11)

<400> SEQUENCE: 32
cttccttatc ggaggtcgaa agttgacccc aactc                        35

<210> SEQ ID NO 33
<211> LENGTH: 35

```
<212> TYPE: DNA
<213> ORGANISM: Artificial Sequence
<220> FEATURE:
<223> OTHER INFORMATION: designed primer (primer 12)

<400> SEQUENCE: 33
cagtgggcag ctgacaaaat gtacttgtta ctgat                              35

<210> SEQ ID NO 34
<211> LENGTH: 57
<212> TYPE: DNA
<213> ORGANISM: Artificial Sequence
<220> FEATURE:
<223> OTHER INFORMATION: designed primer (primer 13)

<400> SEQUENCE: 34
gggaccggtc accaccatca ccatcacatc gagggcagaa gaggagtaga tctgggc      57

<210> SEQ ID NO 35
<211> LENGTH: 35
<212> TYPE: DNA
<213> ORGANISM: Artificial Sequence
<220> FEATURE:
<223> OTHER INFORMATION: designed primer (primer 14)

<400> SEQUENCE: 35
gggctcgagt caaatgaact gccgaatcca cgata                              35

<210> SEQ ID NO 36
<211> LENGTH: 39
<212> TYPE: DNA
<213> ORGANISM: Artificial Sequence
<220> FEATURE:
<223> OTHER INFORMATION: designed primer (primer 15)

<400> SEQUENCE: 36
ggggaattca agcttgccac catggcgtgg atttgtgtg                          39

<210> SEQ ID NO 37
<211> LENGTH: 33
<212> TYPE: DNA
<213> ORGANISM: Artificial Sequence
<220> FEATURE:
<223> OTHER INFORMATION: designed primer (primer 16)

<400> SEQUENCE: 37
acctccaatg aggaagcagt gggcagcaga caa                                33

<210> SEQ ID NO 38
<211> LENGTH: 33
<212> TYPE: DNA
<213> ORGANISM: Artificial Sequence
<220> FEATURE:
<223> OTHER INFORMATION: designed primer (primer 17)

<400> SEQUENCE: 38
ttgtctgctg cccactgctt cctcattgga ggt                                33

<210> SEQ ID NO 39
<211> LENGTH: 35
<212> TYPE: DNA
<213> ORGANISM: Artificial Sequence
<220> FEATURE:
<223> OTHER INFORMATION: designed primer (primer 18)

<400> SEQUENCE: 39
```

```
gggctcgagt cagttagtga ctgcctggtc taacg                           35

<210> SEQ ID NO 40
<211> LENGTH: 48
<212> TYPE: DNA
<213> ORGANISM: Artificial Sequence
<220> FEATURE:
<223> OTHER INFORMATION: designed primer (primer 19)

<400> SEQUENCE: 40
gggctcgagt cagtgatggt gatggtggtg gttagtgact gcctggtc             48

<210> SEQ ID NO 41
<211> LENGTH: 35
<212> TYPE: DNA
<213> ORGANISM: Artificial Sequence
<220> FEATURE:
<223> OTHER INFORMATION: designed primer (primer 20)

<400> SEQUENCE: 41
gggaccggtg tggggatcat ctttcctaag acaca                           35

<210> SEQ ID NO 42
<211> LENGTH: 23
<212> TYPE: DNA
<213> ORGANISM: Artificial Sequence
<220> FEATURE:
<223> OTHER INFORMATION: designed primer (primer 21)

<400> SEQUENCE: 42
caccagccac caccttctga tag                                        23
```

UNITED STATES PATENT AND TRADEMARK OFFICE
CERTIFICATE OF CORRECTION

PATENT NO. : 11,499,177 B2
APPLICATION NO. : 16/490100
DATED : November 15, 2022
INVENTOR(S) : Yuki Kobayashi et al.

It is certified that error appears in the above-identified patent and that said Letters Patent is hereby corrected as shown below:

On the Title Page

Item (56) References Cited, OTHER PUBLICATIONS (Column 1, Line 6), "C191-0220" should read -- C191-C220 --.

Item (56) References Cited, OTHER PUBLICATIONS (Column 1, Line 10), "Engmeering ." should read -- Engineering. --.

Item (56) References Cited, OTHER PUBLICATIONS (Column 1, Line 11), "Kalshi," should read -- Kaishi, --.

Item (56) References Cited, OTHER PUBLICATIONS (Column 2, Line 3), "lle-lle" should read -- Ile-Ile --.

Item (56) References Cited, OTHER PUBLICATIONS (Column 2, Line 3), "Chm" should read -- Chem --.

Item (56) References Cited, OTHER PUBLICATIONS (Column 2, Line 13), "Sol vent Stabuility"," should read -- Solvent Stability", --.

Item (56) References Cited, OTHER PUBLICATIONS (Column 2, Line 16), "Substilisin"," should read -- Subtilisin --.

In the Specification

Column 8, Line 61, "units/µµmol" should read -- units/µmol --.

Column 8, Line 62, "units/µµmol" should read -- units/µmol --.

Column 10, Line 3, "XP 013783518.1)" should read -- XP_013783518.1) --.

Signed and Sealed this
Seventh Day of February, 2023

Katherine Kelly Vidal
*Director of the United States Patent and Trademark Office*

CERTIFICATE OF CORRECTION (continued)
U.S. Pat. No. 11,499,177 B2

Column 15, Line 35, "5'-terminal-side" should read -- 5'-terminal side --.

Column 20, Line 48, "Carcinoscopius" should read -- Carcinoscorpius --.

Column 34, Line 56, "LFC") in" should read -- LFC" in --.

Column 35, Line 55, "LEE," should read -- LFB, --.

In the Claims

Column 92, Line 50 (Claim 5, Line 1), "claim 1." should read -- claim 2. --.